US012708119B2

(12) United States Patent
Shannon et al.

(10) Patent No.: US 12,708,119 B2
(45) Date of Patent: Aug. 18, 2026

(54) METHODS OF REDUCING OR PREVENTING CLOSTRIDIOIDES DIFFICILE COLONIZATION

(71) Applicant: LIV PROCESS, INC., Ardmore, PA (US)

(72) Inventors: Ronald J. Shannon, Ardmore, PA (US); Michael McIntyre, Ardmore, PA (US); Stefania Fabbri, Daresbury (GB); Samantha Westgate, Daresbury (GB)

(73) Assignee: LIV PROCESS, INC., Ardmore, PA (US)

( * ) Notice: Subject to any disclaimer, the term of this patent is extended or adjusted under 35 U.S.C. 154(b) by 840 days.

(21) Appl. No.: 17/996,394

(22) PCT Filed: Apr. 16, 2021

(86) PCT No.: PCT/US2021/027601

§ 371 (c)(1),
(2) Date: Oct. 17, 2022

(87) PCT Pub. No.: WO2021/211921

PCT Pub. Date: Oct. 21, 2021

(65) Prior Publication Data

US 2023/0200397 A1 Jun. 29, 2023

Related U.S. Application Data

(60) Provisional application No. 63/011,850, filed on Apr. 17, 2020.

(51) Int. Cl.
*A01N 63/60* (2020.01)
*A01N 37/16* (2006.01)
*C12N 15/115* (2010.01)

(52) U.S. Cl.
CPC ............. *A01N 63/60* (2020.01); *A01N 37/16* (2013.01); *C12N 15/115* (2013.01); *C12N 2310/16* (2013.01)

(58) Field of Classification Search
None
See application file for complete search history.

(56) References Cited

U.S. PATENT DOCUMENTS 8,592,202 B2 11/2013 Heyduk
8,697,374 B2 4/2014 Rajagopal et al.
8,895,241 B2 11/2014 Ochsner et al.
9,081,010 B2 7/2015 Ochsner
9,139,625 B2 * 9/2015 Cutting ................... A61P 31/04
10,145,844 B2 12/2018 Cameron
11,001,847 B2 * 5/2021 Shannon ................ C12Q 1/689
11,104,905 B2 * 8/2021 Shannon .............. C12N 15/115
11,898,146 B2 * 2/2024 Shannon ............ G01N 33/5308
12,338,442 B2 * 6/2025 Shannon ................ C12Q 1/689
2004/0023266 A1 2/2004 Vivekananda et al.
2008/0020939 A1 1/2008 Stanton et al.
2009/0304683 A1 12/2009 Dimitrov et al.
2010/0196505 A1 * 8/2010 Kaiser .................. C11D 3/3947 510/110
2010/0291100 A1 * 11/2010 Macinga .................. C11D 3/38 530/389.5
2011/0287557 A1 11/2011 Zhang et al.
2012/0231467 A1 9/2012 Ochsner
2012/0308569 A1 12/2012 Chan et al.
2014/0230087 A1 8/2014 Hartig et al.
2015/0056627 A1 2/2015 Karkkainen
2015/0346199 A1 12/2015 Li et al.
2016/0003835 A1 1/2016 Halbert
2016/0143274 A1 5/2016 Bingham et al.
2016/0257959 A1 9/2016 Alsager et al.
2016/0330971 A1 11/2016 Joseph
2017/0265463 A1 * 9/2017 Donskey ................ A01N 31/02
2017/0362307 A1 12/2017 Ingber et al.
2018/0003712 A1 1/2018 Haam et al.
2018/0271423 A1 9/2018 Agarwal
2019/0069836 A1 3/2019 Hettrick
2019/0071714 A1 * 3/2019 Li ........................ C12Q 1/6816
2020/0332296 A1 10/2020 Kang
2020/0385730 A1 12/2020 Shannon (Continued)

FOREIGN PATENT DOCUMENTS

CN 109517823 A 3/2019
CN 110938632 A 3/2020

(Continued)

OTHER PUBLICATIONS

Jang, Sung Key, "A '15-minute' quick diagnostic testing for newly emerging viruses introduced." Pohang University of Science and Technology, pp. 1-3, Mar. 23, 2020.
Peng, C et al., EST9000-ylzaca0_0119_C08.ab1 six cone snails venom ducts mixed library Conus betulinus cDNA, mRNA sequence. Genbank entry (online). National Center for Biotechnology Information. Apr. 18, 2016 [retrieved on Sep. 4, 2021]. Retrieved from the Internet: [URL: https://www.ncbi.nlm.nih.gov/nucleotide/JZ914656.1J; pp. 1-2.
International Search Report and Written Opinion in PCT International Application No. PCT/US2021/027601 mailed Oct. 1, 2021 (23 pages).
Liu et al., "In Vitro Selection of Circular DNA Aptamers for Biosensing Applications," Angewandte Chemie International Edition, 2019, vol. 58, pp. 8013-8017.
Wang et al., "Screenng of DNA Aptamers against Myoglobin Using a Positive and Negative Selection Units Integrated Microfluidic Chip and Its Biosensing Application," Analytical Chemistry, vol. 86, pp. 6572-6659, Jun. 10, 2014.

(Continued)

*Primary Examiner* — Brian Whiteman

(74) *Attorney, Agent, or Firm* — Greenberg Traurig, LLP; Chinh Pham; Natalie Salem

(57) ABSTRACT

Embodiments of the present disclosure relate to a method of preventing and/or reducing *C. difficile* colonization of a surface. In certain embodiments, the aptamer can be used to kill and/or deactivate a *C. difficile* spore. In certain embodiments, the aptamer can be used to increase the sporicidal activity of a sporicidal agent. Embodiments of the present disclosure relate to the use of aptamers which specifically bind to *C. difficile* surface proteins, for example proteins located on the surface of a *C. difficile* spore.

35 Claims, No Drawings

Specification includes a Sequence Listing.

(56) References Cited

U.S. PATENT DOCUMENTS

| | | | |
|---|---|---|---|
| 2020/0385731 | A1 | 12/2020 | Shannon |
| 2021/0332362 | A1 | 10/2021 | Shannon |
| 2022/0177886 | A1 | 6/2022 | Shannon |
| 2022/0307029 | A1 | 9/2022 | Shannon |
| 2023/0228751 | A1 | 7/2023 | Tolley et al. |
| 2025/0130226 | A1 | 4/2025 | Shannon et al. |

FOREIGN PATENT DOCUMENTS

| | | | |
|---|---|---|---|
| CN | 111849994 | A | 10/2020 |
| CN | 112557349 | A | 3/2021 |
| GB | 2491117 | A | 11/2012 |
| WO | 2004058146 | A2 | 7/2004 |
| WO | 2004058146 | A3 | 9/2004 |
| WO | 2010126670 | A2 | 11/2010 |
| WO | 2010126670 | A3 | 3/2011 |
| WO | 2014169344 | A1 | 10/2014 |
| WO | 2016073562 | A1 | 5/2016 |
| WO | 2018106945 | A1 | 6/2018 |
| WO | 2020247755 | A1 | 12/2020 |
| WO | 2021202440 | A1 | 10/2021 |
| WO | 2021211921 | A2 | 10/2021 |
| WO | 2022120004 | A1 | 6/2022 |
| WO | 2023141386 | A1 | 7/2023 |

OTHER PUBLICATIONS

Extended European Search Report dated Jan. 25, 2024 in corresponding European Patent Application No. 20817721.2 (9 pages).

Katilius et al., "Exploring the Sequence Space of a dna Aptamer Using Microarrays", Nucleic Acids Res., vol. 35, No. 22, pp. 7626-7635, 2007.

Mascini et al., "Nucleic Acid and Peptide Aptamers: Fundamentals and Bioanalytical Aspects", Angew Chem. Int. Ed. Engl., vol. 51, No. 6, pp. 1316-1332, Feb. 6, 2012.

Tkhawkho et al., "Destruction of Clostridium Difficile Spores Colitis Using Acidic Electrolyzed Water", Am. J. Infect. Control, vol. 45, No. 9, pp. 1053, Sep. 1, 2017.

Hypothetical protein CD630_ 16130 [Clostridioides difficile 630], record removed, Old YP 001088114.1, accessed and retrieved from ncbi.nlm.nih.gov on Nov. 6, 2023. (Year: 2023).

CotA family spore coat protein [Clostridioides difficile], NCBI Reference Sequence: WP 003436448.1, accessed and retrieved from ncbi.nlm.nih.gov on Nov. 6, 2023. (Year: 2023).

Omidbakhsh, "Evaluation of Sporicidal Activities of Selected Environmental Surface Disinfectants: Carrier Tests with the Sores of Clostridium Difficile and Its Surrogates", American Journal of Infection Control, vol. 38, No. 9, pp. 718-722, Nov. 1, 2010.

Dong et al., "Graphene/aptamer probes for small molecule detection: fromtest toimaging", Microchimica Acta, vol. 187, No. 3, pp. 179, Feb. 19, 2020 (Abstract only).

Gao et al., "Graphene Oxide Quantum Dots Assisted Construction of Fluorescent Aptasensor for Rapid Detection of seudomonas Aeruginosa in Food Samples", Journal of Agricultural and Food Chemistry, vol. 66, No. 41, pp. 10898-10905, Sep. 24, 2018 (Abstract only).

Hui et al., "A Paper Sensor Printed with Multifunctional Bio/Nano Materials", Angewandte Chemie, vol. 57, No. 17, pp. 4549-4553, Mar. 15, 2018 (Abstract only).

Lardoux et al., "Test method for boom suspension influence on spray distribution. Part II: Validation and use of a spray distribution model.", Bioprocess and Biosystems Engineering, vol. 96, No. 2, pp. 161-168, 2007.

Liu et al., "Aptamer-based detection of *Salmonella enteritidis*using double signal amplification by Klenow fragment and dual fluorescence", Microchimica Acta, vol. 183, No. 2, pp. 643-649, Dec. 10, 2015 (Abstract only).

Wu et al.,"A Simple Aptamer Biosensor for *Salmonellae enteritidis* based on Fluorescence-Switch Signaling Graphene Oxide", RSC Advances, vol. 4, No. 42, pp. 22009-22012, Jan. 1, 2014.

Zhang et al., "Fluorescent biosensors enabled by graphene and graphene oxide", Biosensors and Bioelectronics, vol. 89, pp. 96-106, Jul. 9, 2016 (Abstract only).

Ausubel et al., "Current protocols in molecular biology," John Wiley and Sons, 1990, N.Y. (Textbook).

Calderon-Romero et al., "Clostridium difficile exosporium cysteine-rich proteins are essential for the morphogenesis of the exosporium layer, spore resistance, and affect C. difficile pathogenesis," PLOS Pathogens, Aug. 8, 2018, vol. 14, No. 8, e1007199, pp. 1-33.

Chan et al., "Antisense Oligonucleotides: From Design to Therapeutic Application," Clinical and Experimental Pharmacology Physiology, 2006, vol. 33, No. 5-6, pp. 533-540.

Chemgene HLD4H RTU Spray, <URL = https://www.starlabgroup.com/GB-en/product/chemgene-hld4h-rtu-spray-blue-eucalyptus-110-750ml-case-xtm302-c.html>, online resource, Feb. 17, 2023.

Diaz-Gonzalez et al., "Protein Composition of the Outermost Exosporium-like Layer of Clostridium difficile 630 Spores," Journal of Proteomics, Jun. 18, 2015, vol. 123, pp. 1-13.

Didenko, Vladimir V., Fluorescent Energy Transfer Nucleic Acid Probes: Designs and Protocols, 2008 (Textbook).

GenBank Accession No. LN034564.1, Create Date Oct. 7, 2014.

Hong et al., "The Spore Coat Protein CotE Facilitates Host Colonization by Clostridium Difficile," The Journal of Infectious Diseases, Dec. 12, 2017, vol. 216, No. 11, pp. 1452-1459.

Ikanovic et al., "Fluorescence Assay Based on Aptamer-Quantum Dot Binding to Bacillus thuringiensis Spores," Journal of Fluorescence, Jan. 31, 2007, vol. 17, pp. 193-199.

Johansson, "Choosing Reporter-Quencher Pairs for Efficient Quenching Through Formation of Intramolecular Dimers," Fluorescent Energy Transfer Nucleic Acid Probes: Designs and Protocols, 2006, pp. 17-29.

Marras et al., "Efficiencies of Fluorescence Resonance Energy Transfer and Contact-mediated Quenching in Oligonucleotide Probes," Nucleic Acids Research, Nov. 2002, vol. 30, No. 21, p. e122.

* cited by examiner

SEQUENCE LISTING

<160> NUMBER OF SEQ ID NOS: 55

<210> SEQ ID NO 1
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ccagtgtaga ctactcaatg ctcttacgat cctcacctgc tagcacaccc atatcccatg 60
cgtactatcc acaggtcaac c 81

<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
ccagtgtaga ctactcaatg cgggttgcga catggtggta agagctcagc ccgttcccat 60
agtactatcc acaggtcaac c 81

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ccagtgtaga ctactcaatg cacggcctgt tcgtaagacc cttacagact agtttttccc 60
tgtactatcc acaggtcaac c 81

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
ccagtgtaga ctactcaatg ccctattagc tgtatcgatc cgtttagtcg ctcctccgat 60
agtactatcc acaggtcaac c 81

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
ccagtgtaga ctactcaatg cctggtaaat cgatgaccgc tgcctcgcct gagtaatcat 60
cgtactatcc acaggtcaac c 81

<210> SEQ ID NO 6
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
ccagtgtaga ctactcaatg ccgtggactg gtcgggtttg gattcggcag atgaatcagt 60
agtactatcc acaggtcaac c 81

<210> SEQ ID NO 7
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
ccagtgtaga ctactcaatg ccttgtaaga agaacaatcg ccgcttcgcc tgaataggtt 60
cgtactatcc acaggtcaac c 81

<210> SEQ ID NO 8
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ccagtgtaga ctactcaatg cggaccgttg cctcgcccga gtaatccgcc atcgcctttc 60
cgtactatcc acaggtcaac c 81

<210> SEQ ID NO 9
<211> LENGTH: 81

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
ccagtgtaga ctactcaatg cttaagttct ggggacacgt gatgaacgca tttaatgggg 60
cgtactatcc acaggtcaac c 81

<210> SEQ ID NO 10
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
ccagtgtaga ctactcaatg ccgtggactg gtcgggtttg gattcggcag atgaatcact 60
agtactatcc acaggtcaac c 81

<210> SEQ ID NO 11
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ccagtgtaga ctactcaatg cggctgtgtg acttgacctt tggaatgggt gggagggatg 60
ggtactatcc acaggtcaac c 81

<210> SEQ ID NO 12
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
ccagtgtaga ctactcaatg cggtgtggtg accttgacct atggaacctg gttgtagtac 60
tatccacagg tcaacc 76

<210> SEQ ID NO 13
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
ccagtgtaga ctactcaatg ctcgacattt ccgccccgac ggccctccta gtgatgggga 60
gagtactatc cacaggtcaa cc 82

<210> SEQ ID NO 14
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
ccagtgtaga ctactcaatg ccttccattc acctaccgag ctaagcgttc gacttaggtc 60
tgtactatcc acaggtcaac c 81

<210> SEQ ID NO 15
<211> LENGTH: 305
<212> TYPE: PRT
<213> ORGANISM: Clostridium difficile

<400> SEQUENCE: 15

```
Met Glu Asn Asn Lys Cys Arg Glu Asp Phe Arg Phe Thr Gln Glu Tyr
1               5                   10                  15

Glu Glu Asp Tyr Pro Asn Thr Asn Glu Arg Tyr Tyr Glu Asn Tyr Gln
            20                  25                  30

Val Ala Asp Arg Tyr Tyr Asn Tyr Pro Asn Lys Tyr Lys Glu Pro Lys
        35                  40                  45

Ile Lys Gln Cys Cys Cys Lys Lys Ser Met Arg Glu Ala Leu Glu Leu
    50                  55                  60

Leu Arg Tyr Asp Ala Leu Arg Pro Phe Val Asn Phe Asn Gln Phe Ala
65                  70                  75                  80

Phe Ile Ser Asp Phe Phe Ile Val Gly Ala Asn Leu Val Gly Ile Asp
                85                  90                  95

Leu Ser Ala Pro Pro Lys Asp Asn Leu Ser Gly Leu Asp Gly Thr Phe
            100                 105                 110

Glu Arg Phe Ser Ala Cys Asn Cys Asp Leu Ile Asp Ile Ala Gly Arg
        115                 120                 125

Val Ser Tyr Pro Ile Pro Val Pro Leu Thr Leu Glu Gly Leu Ile Asn
    130                 135                 140

Thr Ile Gly Thr Ile Pro Gly Val Ala Glu Leu Ile Ala Leu Ile Asp
145                 150                 155                 160

Ala Val Ile Pro Pro Thr Ile Asp Leu Gly Ala Ile Leu Asp Ala Ile
                165                 170                 175

Leu Ala Ala Ile Ile Asp Phe Ile Leu Ala Ala Ser Thr Pro Leu Ala
            180                 185                 190

Asn Val Asp Leu Ala Ser Leu Cys Asn Leu Lys Ala Val Ala Phe Asp
        195                 200                 205

Ile Thr Pro Ala Asp Tyr Glu Asp Phe Ile Ala Ser Leu Gly Tyr Tyr
    210                 215                 220

Leu Asp Lys Lys His Tyr Lys Glu Cys Asn Cys Asn Cys Asp Cys Asp
225                 230                 235                 240

Asp Cys Cys Cys Asn Lys Gly Ile Leu Asp Asn Leu Tyr Met Ser Asn
                245                 250                 255

Ile Asn Asn Gln Val Thr Val Val Ala Gly Ser Leu Val Leu Thr Gly
            260                 265                 270

Val Glu Val Leu Gly Lys Lys Asn Asp Val Ile Val Leu Gly Asn Ser
        275                 280                 285

Asn Asp Ser Arg Ile Tyr Phe Val Cys Val Asp Ser Ile Asp Tyr Ile
    290                 295                 300

Ala
305
```

<210> SEQ ID NO 16
<211> LENGTH: 712

```
<212> TYPE: PRT
<213> ORGANISM: Clostridium difficile

<400> SEQUENCE: 16

Met Ile Tyr Met Pro Asn Leu Pro Ser Leu Gly Ser Lys Ala Pro Asp
1               5                   10                  15

Phe Lys Ala Asn Thr Thr Asn Gly Pro Ile Arg Leu Ser Asp Tyr Lys
            20                  25                  30

Gly Asn Trp Ile Val Leu Phe Ser His Pro Gly Asp Phe Thr Pro Val
        35                  40                  45

Cys Thr Thr Glu Phe Leu Cys Phe Ala Lys Tyr Tyr Asp Glu Phe Lys
    50                  55                  60

Lys Arg Asn Thr Glu Leu Ile Gly Leu Ser Val Asp Ser Asn Ser Ser
65                  70                  75                  80

His Leu Ala Trp Met Tyr Asn Ile Ser Leu Leu Thr Gly Val Glu Ile
                85                  90                  95

Pro Phe Pro Ile Ile Glu Asp Arg Asp Met Arg Ile Ala Lys Leu Tyr
            100                 105                 110

Gly Met Ile Ser Lys Pro Met Ser Asp Thr Ser Thr Val Arg Ser Val
        115                 120                 125

Phe Ile Ile Asp Asn Asn Gln Ile Leu Arg Thr Ile Leu Tyr Tyr Pro
    130                 135                 140

Leu Thr Thr Gly Arg Asn Ile Pro Glu Ile Leu Arg Ile Val Asp Ala
145                 150                 155                 160

Leu Gln Thr Ser Asp Arg Asp Asn Ile Val Thr Pro Ala Asn Trp Phe
                165                 170                 175

Pro Gly Met Pro Val Ile Leu Pro Tyr Pro Lys Asn Tyr Lys Glu Leu
            180                 185                 190

Lys Asn Arg Val Asn Ser Cys Asn Lys Lys Tyr Ser Cys Met Asp Trp
        195                 200                 205

Tyr Leu Cys Phe Val Pro Asp Asn Tyr Asn Asp Glu Glu Val Ser Lys
    210                 215                 220

Lys Ile Asp Asn Thr Cys Ser Trp Lys Lys Glu His Thr Lys Asn Ile
225                 230                 235                 240

Glu Asn Glu Cys Asn Cys Glu His Glu His His Asp Tyr Leu Asn Lys
                245                 250                 255

Ala Leu Asp Cys Lys Gln Glu His Lys Thr Asp Ile Lys Asp Asp Cys
            260                 265                 270

Asn His Glu Lys Lys His Thr Lys Asn Thr Asn Lys Val His Asn Ser
        275                 280                 285

Lys Gln Asp Lys Phe Lys Asp Lys Ser Cys Asp Glu Met Asn Phe Asn
    290                 295                 300

Tyr Asp Lys Asp Glu Ser Cys Asp Lys Ile Asn Ser Ser Tyr Asn Lys
305                 310                 315                 320

Glu Asp Ser Ser Tyr Glu Asp Phe Tyr Lys His Asn Tyr Lys Asn Tyr
                325                 330                 335

Asp Tyr Thr Ser Glu Lys Asn Thr Lys Lys Ile Ala Met Lys Thr Leu
            340                 345                 350

Lys Asp Ser Lys Lys Leu Val Arg Pro Gln Ile Thr Asp Pro Tyr Asn
        355                 360                 365

Pro Ile Val Glu Asn Ala Asn Cys Pro Asp Ile Asn Pro Ile Val Ala
    370                 375                 380

Glu Tyr Val Leu Gly Asn Pro Thr Asn Val Asp Ala Gln Leu Leu Asp
385                 390                 395                 400
```

Ala Val Ile Phe Ala Phe Ala Glu Ile Asp Gln Ser Gly Asn Leu Phe
405 410 415

Ile Pro Tyr Pro Arg Phe Leu Asn Gln Leu Leu Ala Leu Lys Gly Glu
420 425 430

Lys Pro Ser Leu Lys Val Ile Val Ala Ile Gly Gly Trp Gly Ala Glu
435 440 445

Gly Phe Ser Asp Ala Ala Leu Thr Pro Thr Ser Arg Tyr Asn Phe Ala
450 455 460

Arg Gln Val Asn Gln Met Ile Asn Glu Tyr Ala Leu Asp Gly Ile Asp
465 470 475 480

Ile Asp Trp Glu Tyr Pro Gly Ser Ser Ala Ser Gly Ile Thr Ser Arg
485 490 495

Pro Gln Asp Arg Glu Asn Phe Thr Leu Leu Leu Thr Ala Ile Arg Asp
500 505 510

Val Ile Gly Asp Asp Lys Trp Leu Ser Val Ala Gly Thr Gly Asp Arg
515 520 525

Gly Tyr Ile Asn Ser Ser Ala Glu Ile Asp Lys Ile Ala Pro Ile Ile
530 535 540

Asp Tyr Phe Asn Leu Met Ser Tyr Asp Phe Thr Ala Gly Glu Thr Gly
545 550 555 560

Pro Asn Gly Arg Lys His Gln Ala Asn Leu Phe Asp Ser Asp Leu Ser
565 570 575

Leu Pro Gly Tyr Ser Val Asp Ala Met Val Arg Asn Leu Glu Asn Ala
580 585 590

Gly Met Pro Ser Glu Lys Ile Leu Leu Gly Ile Pro Phe Tyr Gly Arg
595 600 605

Leu Gly Ala Thr Ile Thr Arg Thr Tyr Asp Glu Leu Arg Arg Asp Tyr
610 615 620

Ile Asn Lys Asn Gly Tyr Glu Tyr Arg Phe Asp Asn Thr Ala Gln Val
625 630 635 640

Pro Tyr Leu Val Lys Asp Gly Asp Phe Ala Met Ser Tyr Asp Asp Ala
645 650 655

Leu Ser Ile Phe Leu Lys Thr Gln Tyr Val Leu Arg Asn Cys Leu Gly
660 665 670

Gly Val Phe Ser Trp Thr Ser Thr Tyr Asp Gln Ala Asn Ile Leu Ala
675 680 685

Arg Thr Met Ser Ile Gly Ile Asn Asp Pro Glu Val Leu Lys Glu Glu
690 695 700

Leu Glu Gly Ile Tyr Gly Gln Phe
705 710

<210> SEQ ID NO 17
<211> LENGTH: 332
<212> TYPE: PRT
<213> ORGANISM: Clostridium difficile

<400> SEQUENCE: 17

Pro Ile Val Ala Glu Tyr Val Leu Gly Asn Pro Thr Asn Val Asp Ala
1 5 10 15

Gln Leu Leu Asp Ala Val Ile Phe Ala Phe Ala Glu Ile Asp Gln Ser
20 25 30

Gly Asn Leu Phe Ile Pro Tyr Pro Arg Phe Leu Asn Gln Leu Leu Ala
35 40 45

Leu Lys Gly Glu Lys Pro Ser Leu Lys Val Ile Val Ala Ile Gly Gly

```
    50                  55                  60

Trp Gly Ala Glu Gly Phe Ser Asp Ala Ala Leu Thr Pro Thr Ser Arg
65                  70                  75                  80

Tyr Asn Phe Ala Arg Gln Val Asn Gln Met Ile Asn Glu Tyr Ala Leu
                85                  90                  95

Asp Gly Ile Asp Ile Asp Trp Glu Tyr Pro Gly Ser Ser Ala Ser Gly
            100                 105                 110

Ile Thr Ser Arg Pro Gln Asp Arg Glu Asn Phe Thr Leu Leu Leu Thr
        115                 120                 125

Ala Ile Arg Asp Val Ile Gly Asp Asp Lys Trp Leu Ser Val Ala Gly
    130                 135                 140

Thr Gly Asp Arg Gly Tyr Ile Asn Ser Ser Ala Glu Ile Asp Lys Ile
145                 150                 155                 160

Ala Pro Ile Ile Asp Tyr Phe Asn Leu Met Ser Tyr Asp Phe Thr Ala
                165                 170                 175

Gly Glu Thr Gly Pro Asn Gly Arg Lys His Gln Ala Asn Leu Phe Asp
            180                 185                 190

Ser Asp Leu Ser Leu Pro Gly Tyr Ser Val Asp Ala Met Val Arg Asn
        195                 200                 205

Leu Glu Asn Ala Gly Met Pro Ser Glu Lys Ile Leu Leu Gly Ile Pro
    210                 215                 220

Phe Tyr Gly Arg Leu Gly Ala Thr Ile Thr Arg Thr Tyr Asp Glu Leu
225                 230                 235                 240

Arg Arg Asp Tyr Ile Asn Lys Asn Gly Tyr Glu Tyr Arg Phe Asp Asn
                245                 250                 255

Thr Ala Gln Val Pro Tyr Leu Val Lys Asp Gly Asp Phe Ala Met Ser
            260                 265                 270

Tyr Asp Asp Ala Leu Ser Ile Phe Leu Lys Thr Gln Tyr Val Leu Arg
        275                 280                 285

Asn Cys Leu Gly Gly Val Phe Ser Trp Thr Ser Thr Tyr Asp Gln Ala
    290                 295                 300

Asn Ile Leu Ala Arg Thr Met Ser Ile Gly Ile Asn Asp Pro Glu Val
305                 310                 315                 320

Leu Lys Glu Glu Leu Glu Gly Ile Tyr Gly Gln Phe
                325                 330


<210> SEQ ID NO 18
<211> LENGTH: 405
<212> TYPE: PRT
<213> ORGANISM: Clostridium difficile

<400> SEQUENCE: 18

Met Gln Asp Tyr Lys Lys Asn Lys Arg Arg Met Met Asn Gln Pro Met
1               5                   10                  15

Ser Thr Met Asn Glu Glu Glu Val Tyr Thr Asp Glu Ile Asn Ser Glu
            20                  25                  30

Asp Met Arg Gly Phe Lys Lys Ser His His His Asn Gly Cys Asn Thr
        35                  40                  45

Asp Asn Lys Cys Glu Cys His Asp Asp Cys Asn Pro Cys Asn Pro Cys
    50                  55                  60

Asn Pro Cys Lys Pro Asn Pro Cys Asn Pro Cys Lys Pro Asn Pro Cys
65                  70                  75                  80

Asp Asp Asn Cys Gly Cys His Asp Asn Cys Lys Cys Asp Cys Glu Pro
                85                  90                  95
```

```
Cys Glu Met Asp Ser Asp Glu Cys Phe Glu Asn Lys Cys Gly Pro Glu
            100                 105                 110

Cys Cys Asn Pro Ile Ser Pro Arg Asn Phe Ser Val Ser Asn Ala Val
        115                 120                 125

Pro Phe Ala Ile Glu Ala Asn Arg Ile Phe Asp Thr Met Gln Phe Gln
    130                 135                 140

Thr Phe Thr Asp Ala Thr Gly Pro Asn Gly Glu Pro Leu Thr Phe Glu
145                 150                 155                 160

Thr Glu Val Val Glu Val Phe Gly Ser Val Pro Ser Ala Gly Gln Ala
                165                 170                 175

Ser Val Thr Ile Glu Lys Ile Cys Leu Ser Asn Asp Gly Ile Val Ile
            180                 185                 190

Asp Thr Gly Met Thr Thr Leu Glu Asp Phe Asp Leu Asp Pro Leu Gly
        195                 200                 205

Asp Ile Val Gly Arg Asn Cys Glu Thr Thr Phe Glu Phe Ala Val Cys
    210                 215                 220

Gly Glu Arg Asn Ser Glu Cys Cys Arg Gln Gly Lys Gly Lys Ser Val
225                 230                 235                 240

Ala Tyr Lys Gln Arg Gly Leu Thr Val Ala Val Arg Asn Leu Val Leu
                245                 250                 255

Glu Leu Arg Gly Arg Cys Gly Cys Thr Glu Phe Val Ala Leu Ala Phe
            260                 265                 270

Pro Ala Val Arg Ala Gly Gly Gly Cys Lys Arg Arg Val Asp Tyr Val
        275                 280                 285

Glu Phe Thr Phe Asn Thr Leu Ser Ala Pro Ile Cys Leu Pro Ala Asp
    290                 295                 300

Gly Arg Ala Val Thr Leu Arg Gln Glu Tyr Gln Thr Asn Leu Thr Val
305                 310                 315                 320

Asp Cys Ile Gly Lys Ser Ile Leu Lys Leu Glu Cys Asn Glu Cys Cys
                325                 330                 335

Glu Pro Phe Tyr Glu Leu Ile Ile Pro Asn Asp Ile Asp Leu Val Leu
            340                 345                 350

Cys Leu Gln Glu Thr Val Ser Thr Leu Ile Ser Glu Gln Ile Val Val
        355                 360                 365

Leu Ala Ser Pro Asn Pro Ile Gln Pro Arg Leu Val Asp Thr Phe Ser
    370                 375                 380

Lys Val Cys Asp Phe Ser Gln Cys Gly Pro Asn His Gly Ser Gly Lys
385                 390                 395                 400

Pro Ser Cys His Arg
                405


<210> SEQ ID NO 19
<211> LENGTH: 157
<212> TYPE: PRT
<213> ORGANISM: Clostridium difficile

<400> SEQUENCE: 19

Met Glu Asn Lys Lys Cys Tyr Ser Glu Asp Trp Tyr Glu Arg Gly Glu
1               5                   10                  15

Ser Thr Ala Lys Trp Phe Gln Asn Asp Arg Glu Glu Tyr Glu Arg Glu
            20                  25                  30

Ala Tyr Asp Glu Asp Arg Glu Arg Arg Gly Ser Asn Cys Gly Cys Ser
        35                  40                  45

Asp Ser Gly Glu Asn Arg Pro Arg Asn Cys Glu Arg Phe Arg Arg Glu
    50                  55                  60
```

```
Ala Glu Ile Arg Glu Arg Glu Ala Arg Glu Ala Phe Cys Glu Ser Ser
65                  70                  75                  80

Glu Lys Lys Lys Glu Ala Leu Ala Tyr Glu Cys Glu Ala Arg Lys Leu
                85                  90                  95

Trp Glu Glu Ala Glu Lys Tyr Trp Asp Glu Tyr Ser Lys Tyr Asn Tyr
            100                 105                 110

Lys Gly Ile Glu Tyr Leu Ala Glu Ala Ala Arg Leu Phe Asp Glu Gly
        115                 120                 125

Met Glu Cys Glu Ala Arg Arg Asn Gly Asn Asn Gly Gly Asn Asn Asn
    130                 135                 140

Asn Cys Cys His Lys Cys Asn Cys Asn Cys Cys Arg Lys
145                 150                 155


<210> SEQ ID NO 20
<211> LENGTH: 432
<212> TYPE: PRT
<213> ORGANISM: Clostridium difficile

<400> SEQUENCE: 20

Asn Thr Asn Lys Val His Asn Ser Lys Gln Asp Lys Phe Lys Asp Lys
1               5                   10                  15

Ser Cys Asp Glu Met Asn Phe Asn Tyr Asp Lys Asp Glu Ser Cys Asp
            20                  25                  30

Lys Ile Asn Ser Ser Tyr Asn Lys Glu Asp Ser Ser Tyr Glu Asp Phe
        35                  40                  45

Tyr Lys His Asn Tyr Lys Asn Tyr Asp Tyr Thr Ser Glu Lys Asn Thr
    50                  55                  60

Lys Lys Ile Ala Met Lys Thr Leu Lys Asp Ser Lys Lys Leu Val Arg
65                  70                  75                  80

Pro Gln Ile Thr Asp Pro Tyr Asn Pro Ile Val Glu Asn Ala Asn Cys
                85                  90                  95

Pro Asp Ile Asn Pro Ile Val Ala Glu Tyr Val Leu Gly Asn Pro Thr
            100                 105                 110

Asn Val Asp Ala Gln Leu Leu Asp Ala Val Ile Phe Ala Phe Ala Glu
        115                 120                 125

Ile Asp Gln Ser Gly Asn Leu Phe Ile Pro Tyr Pro Arg Phe Leu Asn
    130                 135                 140

Gln Leu Leu Ala Leu Lys Gly Glu Lys Pro Ser Leu Lys Val Ile Val
145                 150                 155                 160

Ala Ile Gly Gly Trp Gly Ala Glu Gly Phe Ser Asp Ala Ala Leu Thr
                165                 170                 175

Pro Thr Ser Arg Tyr Asn Phe Ala Arg Gln Val Asn Gln Met Ile Asn
            180                 185                 190

Glu Tyr Ala Leu Asp Gly Ile Asp Ile Asp Trp Glu Tyr Pro Gly Ser
        195                 200                 205

Ser Ala Ser Gly Ile Thr Ser Arg Pro Gln Asp Arg Glu Asn Phe Thr
    210                 215                 220

Leu Leu Leu Thr Ala Ile Arg Asp Val Ile Gly Asp Asp Lys Trp Leu
225                 230                 235                 240

Ser Val Ala Gly Thr Gly Asp Arg Gly Tyr Ile Asn Ser Ser Ala Glu
                245                 250                 255

Ile Asp Lys Ile Ala Pro Ile Ile Asp Tyr Phe Asn Leu Met Ser Tyr
            260                 265                 270

Asp Phe Thr Ala Gly Glu Thr Gly Pro Asn Gly Arg Lys His Gln Ala
```

```
        275                 280                 285

Asn Leu Phe Asp Ser Asp Leu Ser Leu Pro Gly Tyr Ser Val Asp Ala
    290                 295                 300

Met Val Arg Asn Leu Glu Asn Ala Gly Met Pro Ser Glu Lys Ile Leu
305                 310                 315                 320

Leu Gly Ile Pro Phe Tyr Gly Arg Leu Gly Ala Thr Ile Thr Arg Thr
                325                 330                 335

Tyr Asp Glu Leu Arg Arg Asp Tyr Ile Asn Lys Asn Gly Tyr Glu Tyr
            340                 345                 350

Arg Phe Asp Asn Thr Ala Gln Val Pro Tyr Leu Val Lys Asp Gly Asp
        355                 360                 365

Phe Ala Met Ser Tyr Asp Asp Ala Leu Ser Ile Phe Leu Lys Thr Gln
    370                 375                 380

Tyr Val Leu Arg Asn Cys Leu Gly Gly Val Phe Ser Trp Thr Ser Thr
385                 390                 395                 400

Tyr Asp Gln Ala Asn Ile Leu Ala Arg Thr Met Ser Ile Gly Ile Asn
                405                 410                 415

Asp Pro Glu Val Leu Lys Glu Glu Leu Glu Gly Ile Tyr Gly Gln Phe
            420                 425                 430


<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

ccagtgtaga ctactcaatg c                                              21


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

gtactatcca caggtcaacc                                                20


<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

atcgatgacc gctgcctcgc ctgagtaatc atcgta                              36


<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
```

ccatactcaa tgctcttacg atcctcatca acc 33

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
ccagtgtaga ctactcaatg ctcttacgat cctcatcaac c 41

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
agtgtagact actcaatgcg gctggccaca ggtcaacc 38

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
cttgaccttt ggaatgggtg ggagggatgg gtactatcca caggtcaacc 50

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
aatgggtggg agggatgggt acta 24

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
cttgaccttt ggaatgggta gggagggagg gatactatcc acaggtcaac c 51

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
cttgaccttt ggaatgggtg ggagggaggg tatccacagg tcaacc 46

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
actactcaat gctcgacatt tccgccccga cggccctcct agtgagggga gagtaga 57

<210> SEQ ID NO 32
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
actactcaat gctcgacatt tccgccccga cggccctcct agtgatgggg agagtaga 58

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
actcaaggcc gtggactggt cgggtttgga ttcggcagat gaatcact 48

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
actcaaggcc gtggactggt cgggtttgga t 31

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
acccgtggga ctgggtcggg tcggg 25

<210> SEQ ID NO 36
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
aactgcctgg taaatcgatg accgctgcct cgcctgagta atcatcgtac tatccacagg 60
tc 62

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
gtaaatcgat gaccgctgcc tcgcctgagt aatcatcgta c 41

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
actactcaaa cccgtggact ggtcgggttt ggattcggca gatgaatcag tagaaa 56

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
actactcaat gccgtggact ggtcgggttt ggaatcggca gatgaatcag tagtaaa 57

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
cattccaaag gtcaag 16

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
cacacattcc aaaaggtcaa g 21

<210> SEQ ID NO 42
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ctcaatgcct tccattcacc taccgagcta agcgttcgac ttaggtctgt act 53

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
cctaccgagc taagcgttcg acttaggtct gtact 35

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ctcacctgct agcacaccca tatcccatgg gtacaatcca caggtcaa 48

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
ctcacctgct agcacaccca catcccgtgc gtgctatcca caggtgaa 48

<210> SEQ ID NO 46
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
agtgcagact actcaatgca cggccggttc ggaagaccct tccagactag tttttccctg 60
tactagtcca ccggcta 77

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
agtgcagact actcaatgca cggcctggtt cgtaagaccc ttaccagact 50

<210> SEQ ID NO 48
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
cggttgcgac atggtggtaa gagctcagcc cgttcccata gtactatcca caggtcaacc 60
t 61

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
cggttgcgac atggtggtaa gagctcagcc cgttcccata gtactatcca caggtcgcaa 60
cct 63

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
cccgtgtaga ctactcaatg cgggctgcga catggtggta agagctcagc ccgttcccat 60
agtactatcc acgggt 76

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
cccgtgtaga ctattttagt actatccacg gg 32

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
tgcgggctgc gacatggtgg taagagctca gcccgtt 37

<210> SEQ ID NO 53
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
acccaggtgt aggacgactc aatgccctat tagctgtatc gatccgttta gtcgctcctc 60
cgatagtacc ctatccacca ggga 84

<210> SEQ ID NO 54
<211> LENGTH: 81
<212> TYPE: DNA

-continued

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: variation
<222> LOCATION: (72)..(72)

<400> SEQUENCE: 54

accaggtggt agacctactc acatgcccta ttagcgtgta tcgatccggt ttagtccgct     60

tcgatagtag ucccaccagg a                                               81


<210> SEQ ID NO 55
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

ctcaatgcct tccattcacc taccgagcta agcgttcgac ttaggtctgt act           53
```

METHODS OF REDUCING OR PREVENTING CLOSTRIDIOIDES DIFFICILE COLONIZATION

RELATED APPLICATIONS

This application is a U.S. national phase application under 35 U.S.C. 371 of PCT International Application No. PCT/US2021/027601, filed Apr. 16, 2021, which claims the benefit of and the priority to U.S. Provisional application Ser. No. 63/011,850, filed Apr. 17, 2020, the entire disclosure of each of which is incorporated herein by reference in their entireties.

SEQUENCE LISTING

The instant application contains a Sequence Listing, submitted herewith which includes the file 193519-010108_ST25.txt having the following size 33,824 bytes, which was created on Apr. 16, 2021, the contents of which are hereby incorporated by reference herein.

FIELD

Embodiments of the present disclosure relate to a method of preventing and/or reducing *C. difficile* colonization of a surface. Embodiments of the present disclosure relate to the use of aptamers which specifically bind to *C. difficile* surface proteins e.g. proteins located on the surface of a *C. difficile* spore. In certain embodiments, the aptamer may be used to kill and/or deactivate a *C. difficile* spore. In certain embodiments, the aptamer may be used to increase the sporicidal activity of a sporicidal agent e.g. a sporicidal solution.

BACKGROUND

*Clostridioides difficile* (also referred to as *C. difficile* and previously referred to as *Clostridium difficile*) is a Gram-positive, anaerobic spore former and is an important nosocomial and community-acquired pathogenic bacterium. *C. difficile* infections (CDI) are a leading cause of infections worldwide with elevated rates of morbidity. Despite the fact that two major virulence factors, the enterotoxin TcdA and the cytotoxin TcdB, are essential in the development of CDI, *C. difficile* spores are the main vehicle of infection, and persistence and transmission of CDI and are thought to play an essential role in episodes of CDI recurrence and horizontal transmission.

SUMMARY

Aspects of the present disclosure relates to a method for reducing and/or preventing *Clostridioides difficile* (*C. difficile*) contamination and products and kits for use in the method. In some embodiments, a method of killing and/or inactivating *C. difficile* spores comprising contacting the spores with an aptamer capable of specifically binding to *C. difficile*, and an agent selected from the group consisting of a sporicidal agent and a sporostatic agent, is provided. In some embodiments, a method of enhancing the sporicidal activity against *C. difficile* spores of a sporicidal agent comprising contacting the spores with an aptamer capable of specifically binding to *C. difficile*, and an agent selected from the group consisting of a sporicidal agent and a sporostatic agent, is provided. In some embodiments, the agent is a sporicidal agent.

In some embodiments, kits for killing and/or inactivating *C. difficile* spores are provided. In some embodiments, the kit comprises an aptamer capable of specifically binding to *C. difficile*, and an agent selected from the group consisting of a sporicidal agent and a sporostatic agent. In some embodiments, kits for enhancing the sporicidal activity against *C. difficile* spores are provided. In some embodiments, the kit comprises an aptamer capable of specifically binding to *C. difficile*, and a sporicidal agent and a sporostatic agent. In some embodiments, the kit comprises a light source and viewing goggles for determining the presence, absence and/or concentration of *C. difficile* at the location prior to contacting the location with the sporicidal agent and/or sporistatic agent.

Embodiments of the disclosure relate to a method of killing and/or inactivating *C. difficile* spores located on a surface. The surface may be a surface located in a hospital or other healthcare facility such as a care home. The surface may be for example a sheet, a hospital surgical gown, flooring, walls, an operating table, furniture or the like. Embodiments of the present disclosure relate to methods of enhancing the sporicidal activity of one or more sporicidal agents comprising the use of aptamers described herein. Embodiments of the disclosure relate to the reduction or prevention of colonization of a location e.g. a surface by *C. difficile*.

In some embodiments, 99.9% of the spores are not capable of transforming into vegetative cells. In an embodiment, 99.99% or 99.999% of the spores are not capable of transforming into vegetative cells. In some embodiments, at least 85% of the spores are not capable of transforming into vegetative cells.

In certain embodiments, the disclosure relates to the use of one or more aptamers, e.g. one, two, three or more aptamers capable of binding to a *C. difficile* spore to facilitate the kill and/or deactivate a *C. difficile* spore. The aptamer(s) may be for use in isolation and/or in combination with a sporicidal agent. Embodiments of the disclosure may comprise the use of one or more aptamers as described herein to increase the sporicidal activity of a sporicidal agent. Further details of sporicidal fluids for use according to embodiments of the disclosure are provided herein.

The *C. difficile* colonization may be comprised of a single strain or may be a mixture of strains.

In an aspect of the present disclosure there is provided a method for killing or inactivating *C. difficile* spores, comprising contacting the spores with an agent selected from the group consisting of a sporicidal agent and a sporostatic agent and one or more aptamers capable of specifically binding to *C. difficile*.

In an aspect of the present disclosure there is provided a method for (i) detecting the presence of *C. difficile* at a location and (ii) killing or inactivating *C. difficile* spores, comprising contacting the spores with an agent selected from the group consisting of a sporicidal agent and a sporostatic agent and one or more aptamers capable of specifically binding to *C. difficile*. In embodiments, one or more aptamers comprises a detection molecule as described herein.

In an aspect of the present disclosure there is provided a method for killing or inactivating *C. difficile* spores, comprising contacting the spores with an agent selected from the group consisting of a sporicidal agent and a sporostatic agent and one or more aptamers capable of specifically binding to *C. difficile*. In embodiments, one or more aptamers comprises a detection molecule as described herein.

In an aspect of the present disclosure there is provided a method for enhancing a sporicidal effect against *C. difficile* of a sporicidal agent, the method comprising contacting *C. difficile* spores with one or more aptamer capable of specifically binding to *C. difficile* and an agent selected from the group consisting of a sporicidal agent and a sporostatic agent.

In an aspect of the present disclosure there is provided a method for (i) detecting the presence of *C. difficile* at a location and (ii) enhancing a sporicidal and/or sporostatic effect against *C. difficile* of a sporicidal agent or sporostatic agent, the method comprising contacting *C. difficile* spores with one or more aptamers capable of specifically binding to *C. difficile* and an agent selected from the group consisting of a sporicidal agent and a sporostatic agent. In embodiments, the one or more aptamers comprises a detection molecule as described herein.

In embodiments, the agent is a sporicidal agent.

In embodiments, the method comprises locating the one or more aptamers and the sporicidal agent at a location suspected of comprising *C. difficile* spores.

In embodiments, the location comprises a surface and the method comprises contacting the surface with the sporicidal agent prior to, at essentially the same time, or subsequent to the one or more aptamers.

In embodiments, the method comprises the steps of contacting the surface with the one or more aptamers for a predetermined period of time configured to enable the one or more aptamers to bind to the *C. difficile* spores to form one or more aptamer-spore complexes, and contacting the surface comprising the one or more aptamer-spore complexes with the sporicidal agent.

In embodiments, the method comprises determining the one or more aptamers bound to the *C. difficile* spore prior to contacting the surface with the sporicidal agent. In embodiments, the method further comprises a step of contacting the surface with a GH neutraliser.

In embodiments, the surface is a surface located on an object e.g. a hospital bed, an operating table, clothing, general-premise surfaces (e.g. floors, walls, ceilings, exterior of furniture), specific-equipment surfaces (e.g. hard surfaces, manufacturing equipment, processing equipment, etc.), textiles (e.g. cottons, wools, silks, synthetic fabrics such as polyesters, polyolefins, and acrylics, fiber blends such as cotton polyester, etc.), wood and cellulose-based systems (e.g. paper), soil, animal carcasses (e.g. hide, meat, hair, feathers, etc.). In some embodiments, the object can be foodstuffs (e.g. fruits, vegetables, nuts, meats, etc.).

In embodiments, the method comprises the steps of contacting a media with the one or more aptamers for a predetermined period of time configured to enable the one or more aptamers to bind to the *C. difficile* spores to form an aptamer-spore complex, and contacting the media comprising the aptamer-spore complex with the sporicidal agent. In some embodiments the media is water.

In embodiments, the method comprises submerging the spores with a composition comprising the one or more aptamers and/or submerging the spores in the agent.

In embodiments, the method comprises spraying the *C. difficile* spores with a composition comprising the aptamer and/or spraying the *C. difficile* spores with the agent.

In embodiments, the method comprises applying a composition comprising the aptamer by means of a cloth and/or applying the agent by means of a cloth and/or a wipe.

In embodiments, the method is performed at a temperature of between about 5° C. to about 90° C. e.g. 5° C., 10° C., 15° C., 20° C., 25° C., 30° C., 35° C., 40° C., 45° C., 50° C., 55° C., 60° C., 65° C., 70° C., 75° C., 80° C. or 90° C. In embodiments, the method may be performed at a temperature in the range of about 5° C. to about 90° C. In embodiments, the method may be performed at a temperature in the range of about 5° C. to 10° C., 10° C. to 15° C., 15° C. to 20° C., 20° C. to 25° C., 25° C. to 30° C., 30° C. to 35° C., 35° C. to 40° C., 40 to 45° C., 45° C. to 50° C., 50° C. to 55° C., 55° C. to 60° C., 60° C. to 65° C., 65° C. to 70° C., 70° C. to 75° C., 75° C. to 80° C., 80° C. to 85° C., 85° C. to 90° C., or any interval between any of these temperature ranges. In an embodiment, the heating temperatures are selected from 1° C. increments selected from the range of 5° C. to 90° C.

In embodiments, the *C. difficile* spores comprise a protein, wherein the protein is a spore coat surface protein or an exosporium layer protein.

In embodiments, the *C. difficile* protein selected from CdeC, CdeM, CotA, CotE and CotE Chitinase.

In embodiments, the *C. difficile* protein is a CdeC protein having an amino acid sequence as set forth in SEQ. ID. NO 18.

In embodiments, the *C. difficile* protein is a CdeM protein having an amino acid sequence as set forth in SEQ. ID. NO. 19.

In embodiments, the *C. difficile* protein is a CotA, protein having an amino acid sequence as set forth in SEQ. ID. NO. 15.

In embodiments, the *C. difficile* protein is a CotE, protein having an amino acid sequence as set forth in SEQ. ID. NO. 16.

In embodiments, the *C. difficile* protein is a CotE Chitinase protein having an amino acid sequence as set forth in SEQ. ID. NO. 17.

In embodiments, the *C. difficile* protein is rCotE protein having an amino acid sequence as set forth in SEQ. ID. NO. 20.

In embodiments, the aptamer is a single stranded DNA aptamer.

In embodiments, the aptamer comprises, consists essentially of, or consists of:

(a) a nucleic acid sequence selected from any one of the nucleic acid sequences as set forth in any of SEQ ID NOs: 1 to 14, 23 to 39 or 43-55;

(b) a nucleic acid sequence having at least 85% identity for example 90%, 95%, 96%, 97%, 98% or 99% sequence identity with any one of the nucleic acid sequences as set forth in any of SEQ ID NOs: 1 to 14, 23 to 39 or 43-55;

(c) a nucleic acid sequence having at least about 20 consecutive nucleotides of any one the nucleic acid sequences as set forth in any of SEQ ID NOs: 1 to 14, 23 to 39 or 43-55; or (d) a nucleic acid sequence having at least about 20 consecutive nucleotides of a sequence having at least 85% identity with any one of SEQ ID NOs 1 to 14, 23 to 39 or 43-55.

In embodiments, the method comprises contacting the location with a plurality of aptamers, wherein each aptamer is capable of specifically binding to a *C. difficile* spore. In embodiments, the plurality of aptamers comprises at least two aptamers capable of specifically binding to the same epitope of a *C. difficile* spore. In embodiments, the plurality of aptamers comprises at least two aptamers, each aptamer being capable of specifically binding to a different epitope of a *C. difficile* spore.

In embodiments, the plurality of aptamers comprises at least two aptamers selected from the group consisting of an aptamer comprising, consisting essentially of, or consisting of:

(a) a nucleic acid sequence selected from any one of the nucleic acid sequences as set forth in any of SEQ ID NOs: 1 to 14, 23 to 39 or 43-55;
(b) a nucleic acid sequence having at least 85% identity for example 90%, 95%, 96%, 97%, 98% or 99% sequence identity with any one of the nucleic acid sequences as set forth in any of SEQ ID NOs: 1 to 14, 23 to 39 or 43-55;
(c) a nucleic acid sequence having at least about 20 consecutive nucleotides of any one the nucleic acid sequences as set forth in any of SEQ ID NOs: 1 to 14, 23 to 39 or 43-55;
(d) a nucleic acid sequence having at least about 20 consecutive nucleotides of a sequence having at least 85% identity with any one of SEQ ID NOs: 1 to 14, 23 to 39 or 43-55, or
(e) a combination of any of (a) to (d).

In embodiments, the plurality of aptamers comprises at least two aptamers selected from the group consisting of:

a) an aptamer which specifically binds to a CdeC;
b) an aptamer which specifically binds to CdeM,
c) an aptamer which specifically binds to CotA,
d) an aptamer which specifically binds to CotE; and
e) an aptamer which specifically binds to CotE Chitinase;
f) a combination of any of (a) to (e).

In embodiments, the plurality of aptamers comprises an aptamer comprising, consisting essentially of, or consisting of a nucleic acid sequence as set forth in SEQ. ID. NO. 1; an aptamer comprising, consisting essentially of, or consisting of a nucleic acid sequence as set forth in SEQ. ID. NO. 5; and an aptamer comprising, consisting essentially of, or consisting of a nucleic acid sequence as set forth in SEQ. ID. NO. 6.

In embodiments, the aptamer comprises a detectable molecule. In embodiments, the detectable molecule is a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, or a liposome.

In certain embodiments, the aptamer comprises one or both molecules of a FRET pair.

In embodiments, the agent is a sporicidal solution which comprises chlorhexidine gluconate and optionally isopropyl alcohol.

In embodiments, the agent is a sporicidal agent which comprises peracetic acid.

In embodiments, the agent is a peracetic acid generating agent, and wherein the method further comprises wetting a wipe comprising sodium percarbonate with an aqueous solution prior to contacting the location.

In embodiments, the sporicidal solution comprises hydrogen peroxide and optionally comprises a silver stabilised hydrogen peroxide.

In embodiments, the sporicidal solution comprises chlorhexidine gluconate and about 70% isopropyl alcohol complex.

In an aspect of the present disclosure, there is provided a combination of an aptamer capable of specifically binding to *C. difficile* and a sporicidal agent and/or a sporistatic agent. The combination may be for use in the killing and/or inactivation of *C. difficile*.

In embodiments, the combination comprises a plurality of aptamers, the plurality of aptamers comprising two or more aptamers as defined herein.

In embodiments, the plurality of aptamers comprises an aptamer comprising or consisting essentially of a nucleic acid sequence as set forth in SEQ. ID. NO. 1; an aptamer comprising or consisting essentially of a nucleic acid sequence as set forth in SEQ. ID. NO. 5 and an aptamer comprising or consisting essentially of a nucleic acid sequence as set forth in SEQ. ID. NO. 6.

In embodiments, the combination comprises a sporicidal agent which comprises peracetic acid and/or an agent capable of generating peracetic acid.

In an aspect of the disclosure, there is provided a composition comprising one or more aptamers as defined herein and a sporicidal agent and/or a sporostatic agent.

In embodiments, the composition comprises an aptamer being capable of specifically binding to *C. difficile*. In embodiments, the composition comprises a plurality of aptamers, each aptamer being capable of specifically binding to the same epitope of a *C. difficile* spore. In embodiments, the plurality of aptamers comprises aptamers capable of binding to different epitopes of a *C. difficile* spore.

In embodiments, the plurality of aptamers comprises an aptamer comprising, consisting essentially of, or consisting of a nucleic acid sequence as set forth in SEQ. ID. NO. 1; an aptamer comprising, consisting essentially of, or consisting of a nucleic acid sequence as set forth in SEQ. ID. NO. 5; and an aptamer comprising, consisting essentially of, or consisting of a nucleic acid sequence as set forth in SEQ. ID. NO. 6.

In embodiments, the sporicidal agent comprises peracetic acid and/or agent capable of generating peracetic acid.

DETAILED DESCRIPTION

Further features of certain embodiments of the present disclosure are described below. The practice of embodiments of the present disclosure will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, 2nd ed., 2002, CRC Press; The Dictionary of Cell and Molecular Biology, 3rd ed., Academic Press; and the Oxford University Press, provide a person skilled in the art with a general dictionary of many of the terms used in this disclosure.

Units, prefixes and symbols are denoted in their Système International de Unitese (SI) accepted form. Numeric ranges are inclusive of the numbers defining the range. Unless otherwise indicated, amino acid sequences are written left to right in amino to carboxy orientation and nucleic acid sequences are written left to right in 5' to 3' orientation.

As used herein, the articles "a" and "an" refer to one or more than one, e.g., to at least one, of the grammatical object of the article. The use of the words "a" or "an" when used in conjunction with the term "comprising" herein may mean "one," "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, kits and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

*Clostridium difficile* bacteria are found throughout the environment e.g. in soil, air, water, food products and human and animal faeces. A small number of people carry *C. difficile* in their intestinal tract without showing any symptoms. However, in other subjects, infection from *C. difficile* can cause symptoms ranging from diarrhea to life-threatening inflammation of the colon. Complications of *C. difficile* infection can include dehydration, kidney failure, toxic megacolon, perforation of the bowel and even death if the infection is not controlled quickly.

It commonly affects older adults in hospitals or long-term care facilities and subjects who have taken antibiotics and those with a compromised immune system are at greater risk of contracting *C. difficile* as are those who have undergone abdominal or gastrointestinal surgery. For example, the mortality rate of *C. difficile* infection can be up to 25% in frail, elderly people in hospitals. It has been postulated that the antibiotic therapy disrupts normal gut microbiota, allowing *C. difficile* colonization and growth because it is naturally resistant to many drugs used to treat other infections, thereby enabling its toxin production.

An increase of *C. difficile* infections in subjects previously considered to be low-risk such as younger and otherwise healthy individuals without exposure to health care facilities has been also been seen in recent years. A new strain of *C. difficile*, Type 027, has recently been identified. Type 027 is a strain that produces more toxins than most other types of *C. difficile* and it causes a greater proportion of severe disease and appears to have a higher mortality.

Metronidazole (400 mg or 500 mg, 3 times daily for 10-14 days) is considered in the UK to be the first-line for treating first episodes of mild to moderate *C. difficile* infection. Vancomycin (125 mg 4 times daily for 10-14 days) is an option for second episodes or if the infection is severe. An infection is defined as severe when there is a raised temperature or white cell count, rising creatinine or signs or symptoms of severe colitis. Vancomycin may also be used in infections caused by the type 027 strain. If infection recurs, vancomycin or fidaxomicin (200 mg twice daily for 10 days) may be used. In some severe cases, a person might have to have surgery to remove the infected part of the intestines.

Spores from *C. difficile* are passed in faeces and can be transmitted to food, surfaces and objects via unwashed hands. The spores can persist for weeks or months on surfaces and transmitted via contact with such surfaces.

Given the rise in antibiotic resistance and the potential mortality associated with *C. difficile* infection, control measures are of the highest importance. Current measures include healthcare providers such as nurses and doctors following protocols such as:

- Clean their hands with soap and water or an alcohol-based hand rub before and after caring for every patient to prevent *C. difficile* and other germs from being passed from one patient to another on their hands.
- Carefully clean hospital rooms and medical equipment that have been used for patients with *C. difficile* infection.
- Only give patients antibiotics when it is necessary.
- Use Contact Precautions to prevent *C. difficile* from spreading to other patients. Contact Precautions mean:
  - Whenever possible, patients with *C. difficile* will have a single room or share a room only with someone else who also has *C. difficile.*
  - Healthcare providers will put on gloves and wear a gown over their clothing while taking care of patients with *C. difficile.*
  - Visitors may also be asked to wear a gown and gloves.
  - When leaving the room, hospital providers and visitors remove their gown and gloves and clean their hands.
  - Patients on Contact Precautions are asked to stay in their hospital rooms as much as possible. They can go to other areas of the hospital for treatments and tests.

Despite these preventative measures, *C. difficile* remains a significant healthcare issue and therefore there is a need for rapid identification of the presence of *C. difficile* in an environment to enable It is an aim of some embodiments of the present disclosure to at least partially mitigate some of the problems identified in the prior art.

It is an aim of certain embodiments of the present disclosure to provide methods and products which have utility in the detection of *C. difficile.*

*Clostridioides difficile* (Formerly *Clostridium difficile*)

Aspects of the disclosure utilise aptamers which are capable of specifically binding to *Clostridioides difficile* (previously referred to as *Clostridium difficile*).

In some embodiments, the aptamer specifically binds to a target as defined herein. The term "target" as used herein is used to relate to a molecule selected from at least one of a *C. difficile* surface protein. In some embodiments, the target molecule is a target protein. In some embodiments, the term "target" as used herein is used to relate to a molecule selected from at least one of a *C. difficile* CotA protein, *C. difficile* CotE protein, *C. difficile* CdeC protein, *C. difficile* CdeM protein, *C. difficile* CotEC chitinase protein, and a *C. difficile* spore. As used herein, the terms "target protein" and "target peptide" are used interchangeably.

Certain embodiments of the present disclosure relate to aptamers which bind to a *C. difficile* spore. In some embodiments, the aptamer is selected against a whole *C. difficile* spore. Thus, in some embodiments, the aptamer selectively binds to a *C. difficile* spore.

Certain embodiments provide an aptamer which binds to a *C. difficile* spore coat protein. Embodiments of the present disclosure may utilise a plurality of aptamers, each aptamer being capable of binding to a unique site on the surface of a *C. difficile* spore. In some embodiments, the aptamer specifically binds to a surface protein of the exosporium layer of the *C. difficile* spore (e.g. CdeC, CdeM). In some embodiments, the aptamer specifically binds to a coat protein of the *C. difficile* spore (e.g. CotA, CotE, CotEC). In some embodiments the In certain embodiments, the aptamer specifically binds to a protein as listed in Table 3 below. In embodiments, the disclosure comprises the use of a plurality of aptamers, each aptamer being capable of specifically bind to a protein listed in Table 3.

TABLE 3

| | |
|---|---|
| CotA | SEQ. ID. No. 15 |
| Cot E | SEQ. ID. No. 16 |
| CotEC | SEQ. ID. No. 17 |
| CdeC | SEQ. ID. No. 18 |
| CdeM | SEQ. ID. No. 19 |

Target Proteins

*C. difficile* produces metabolically dormant spores. The spores comprise an outermost exosporium layer which may comprise a number of surface proteins. In embodiments, the exosporium layer comprises one or more proteins selected from BclA1, BclA2, BclA3, CdeA, CdeB, CdeC and CdeM.

CdeC Protein

In embodiments, the aptamer specifically binds to a *C. difficile* CdeC protein. The amino acid sequence of CdeC is published under UniProtKB—Q18AS2 (Q18AS2_PEPD6) version 1 and is as set forth in SEQ ID NO. 18.

In embodiments, the aptamer binds to an epitope of the CdeC protein which is conserved between *C. difficile* strains. Thus, in certain embodiments, the aptamer is used to detect a plurality of *C. difficile* strains in a sample.

CdeM Protein

In embodiments, the aptamer selectively binds to an amino acid sequence of a *C. difficile* surface-bound CdeM protein. CdeM is a cysteine rich protein which is understood to be required for the morphogenesis of the coat and exosporium layer of spores. An amino acid sequence of a *C. difficile* protein is published under UniProtKB —A0A3T1GTU1 (A0A3T1GTU1_CLODI) (version 1) and shown in SEQ ID NO: 19.

In embodiments, the aptamer binds to an epitope of the CdeM protein which is conserved between *C. difficile* strains. Thus, in certain embodiments, the aptamer is used to detect a plurality of *C. difficile* strains in a sample.

In embodiments, the spores comprise a spore coat. The spore coat may comprise a plurality of proteins including for example CotA and CotB.

CotA

In embodiments, the aptamer specifically binds to a protein encoded by a *C. difficile* CotA gene. The protein may be referred to herein as either CotA or "spore coat assembly protein".

An amino acid sequence of CotA is published under UniProtKB Accession No. Q186G8 (Q186G8_PEPD6) version 1 and shown in SEQ ID NO: 15.

CotE

In embodiments, the aptamer specifically binds to a *C. difficile* protein encoded by a CotE gene. An amino acid sequence of a CotE protein (also referred to as peroxiredoxin) is published under accession number UniProtKB-Q18BV5 (Q18BV5_PEPD6) and is shown in SEQ ID NO: 16.

CotEC Chitinase

In embodiments, the aptamer specifically binds to a recombinant *C. difficile* protein referred to as "CotEC" or "rCotE". The amino acid sequence of CotEC consists of amino acid residues N281-F712 (SEQ ID NO: 20). The recombinant protein comprises a chitinase domain and a sequence unique to CotE. In some embodiments, the aptamer specifically binds to a recombinant *C. difficile* protein referred to as "rCotEC" (also referred to as AB45). The amino acid sequence of rCotEC consists of amino acid residues N381-F712 (SEQ ID NO: 17).

In embodiments, the aptamers are selected against a His-tagged CotEC protein. In some embodiments, the aptamers are selected against a tagged rCotEC protein, including but not limited to His-tagged rCotEC protein.

TABLE 2

| Target Protein | SEQ. ID. No |
|---|---|
| CotA | 15 |
| Cot E | 16 |
| CotEC | 17 |
| CdeC | 18 |
| CdeM | 19 |
| rCotE (LS25) | 20 |

*C. difficile* Spores

In embodiments, the aptamer is selected against a whole *C. difficile* spore. Thus, in certain embodiments, the aptamer selectively binds to a *C. difficile* spore. The *C. difficile* spore may be from a strain selected SH11, PCR ribotype 027, PCR ribotype 010, PCR ribotype 014 and ATCC® 43598™. In embodiments, the *C. difficile* may be a strain of a Clade selected from Clade 1, 2, 3, 4 and 5. In certain embodiments, the strain is selected from SH7 (Clade 1), SH8 (Clade 2), R20291 (Clade 2), SH9 (Clade 3), SH10 (Clade 4), ATCC 43598 (Clade 4) and SH11 (Clade 5). In embodiments, the strain is selected from R20291, ATCC 43598 and SH11.

In embodiments, the method comprises facilitating the killing and/or inactivation of a *C. difficile* strain selected from:

| Clade | Strain Name | Ribotype | Toxin A & B | Toxinotype |
|---|---|---|---|---|
| 1 | SH7 | RT015 | A+ B+ | 0 |
| 2 | SH8 | RT176 | A+ B+ | III |
| 3 | SH9 | RT023 | A+ B+ | IV |
| 4 | SH10 | RT017 | A− B+ | VIII |
| | ATCC43598 | RT017 | A− B+ | VIII |
| 5 | SH11 | RT078 | A+ B+ | V |

In certain embodiments, there is provided an aptamer comprising a nucleic acid sequence selected from a nucleic acid sequence as set forth in Table 1 or Table 4.

TABLE 1

| Aptamer Sequences Sequence |
|---|
| CCAGTGTAGACTACTCAATGCTCTTACGATCCTCACCTGCTAGCACACCCATATCCCATGCGTACTATCCACAGGTCAACC (SEQ ID NO: 1) |
| CCAGTGTAGACTACTCAATGCGGGTTGCGACATGGTGGTAAGAGCTCAGCCCGTTCCCATAGTACTATCCACAGGTCAACC (SEQ ID NO: 2) |
| CCAGTGTAGACTACTCAATGCACGGCCTGTTCGTAAGACCCTTACAGACTAGTTTTTCCCTGTACTATCCACAGGTCAACC (SEQ ID NO: 3) |
| CCAGTGTAGACTACTCAATGCCCTATTAGCTGTATCGATCCGTTTAGTCGCTCCTCCGATAGTACTATCCACAGGTCAACC (SEQ ID NO: 4) |
| CCAGTGTAGACTACTCAATGCCTGGTAAATCGATGACCGCTGCCTCGCCTGAGTAATCATCGTACTATCCACAGGTCAACC (SEQ ID NO: 5) |
| CCAGTGTAGACTACTCAATGCCGTGGACTGGTCGGGTTTGGATTCGGCAGATGAATCAGTAGTACTATCCACAGGTCAACC (SEQ ID NO: 6) |
| CCAGTGTAGACTACTCAATGCCTTGTAAGAAGAACAATCGCCGCTTCGCCTGAATAGGTTCGTACTATCCACAGGTCAACC (SEQ ID NO: 7) |
| CCAGTGTAGACTACTCAATGCGGACCGTTGCCTCGCCCGAGTAATCCGCCATCGCCTTTCCGTACTATCCACAGGTCAACC (SEQ ID NO: 8) |
| CCAGTGTAGACTACTCAATGCTTAAGTTCTGGGGACACGTGATGAACGCATTTAATGGGGCGTACTATCCACAGGTCAACC (SEQ ID NO: 9) |
| CCAGTGTAGACTACTCAATGCCGTGGACTGGTCGGGTTTGGATTCGGCAGATGAATCACTAGTACTATCCACAGGTCAACC (SEQ ID NO: 10) |
| CCAGTGTAGACTACTCAATGCGGCTGTGTGACTTGACCTTTGGAATGGGTGGGAGGGATGGGTACTATCCACAGGTCAACC (SEQ ID NO: 11) |
| CCAGTGTAGACTACTCAATGCGGTGTGGTGACCTTGACCTATGGAACCTGGTTGTAGTACTATCCACAGGTCAACC (SEQ ID NO: 12) |
| CCAGTGTAGACTACTCAATGCTCGACATTTCCGCCCCGACGGCCCTCCTAGTGATGGGGAGAGTACTATCCACAGGTCAACC (SEQ ID NO: 13) |
| CCAGTGTAGACTACTCAATGCCTTCCATTCACCTACCGAGCTAAGCGTTCGACTTAGGTCTGTACTATCCACAGGTCAACC (SEQ ID NO: 14) |
| ATCGATGACCGCTGCCTCGCCTGAGTAATCATCGTA (SEQ ID NO: 23) |
| CCATACTCAATGCTCTTACGATCCTCATCAACC (SEQ ID NO: 24) |
| CCAGTGTAGACTACTCAATGCTCTTACGATCCTCATCAACC (SEQ ID NO: 25) |
| AGTGTAGACTACTCAATGCGGCTGGCCACAGGTCAACC (SEQ ID NO: 26) |
| CTTGACCTTTGGAATGGGTGGGAGGGATGGGTACTATCCACAGGTCAACC (SEQ ID NO: 27) |
| AATGGGTGGGAGGGATGGGTACTA (SEQ ID NO: 28) |
| CTTGACCTTTGGAATGGGTAGGGAGGGAGGGATACTATCCACAGGTCAACC (SEQ ID NO: 29) |
| CTTGACCTTTGGAATGGGTGGGAGGGAGGGTATCCACAGGTCAACC (SEQ ID NO: 30) |

TABLE 1-continued

| Aptamer Sequences Sequence |
|---|
| ACTACTCAATGCTCGACATTTCCGCCCCGACGGCCCTCCTAGTGAGGGGAGAGTAGA (SEQ ID NO: 31) |
| ACTACTCAATGCTCGACATTTCCGCCCCGACGGCCCTCCTAGTGATGGGGAGAGTAGA (SEQ ID NO: 32) |
| ACTCAAGGCCGTGGACTGGTCGGGTTTGGATTCGGCAGATGAATCACT (SEQ ID NO: 33) |
| ACTCAAGGCCGTGGACTGGTCGGGTTTGGAT (SEQ ID NO: 34) |
| ACCCGTGGGACTGGGTCGGGTCGGG (SEQ ID NO: 35) |
| AACTGCCTGGTAAATCGATGACCGCTGCCTCGCCTGAGTAATCATCGTACTATCCACAGGTC (SEQ ID NO: 36) |
| GTAAATCGATGACCGCTGCCTCGCCTGAGTAATCATCGTAC (SEQ ID NO: 37) |
| ACTACTCAAACCCGTGGACTGGTCGGGTTTGGATTCGGCAGATGAATCAGTAGAAA (SEQ ID NO: 38) |
| ACTACTCAATGCCGTGGACTGGTCGGGTTTGGAATCGGCAGATGAATCAGTAGTAAA (SEQ ID NO: 39) |
| CTCAATGCCTTCCATTCACCTACCGAGCTAAGCGTTCGACTTAGGTCTGTACT (SEQ ID NO: 42) |
| CCTACCGAGCTAAGCGTTCGACTTAGGTCTGTACT (SEQ ID NO: 43) |
| CTCACCTGCTAGCACACCCATATCCCATGGGTACAATCCACAGGTCAA (SEQ ID NO: 44) |
| CTCACCTGCTAGCACACCCACATCCCGTGCGTGCTATCCACAGGTGAA (SEQ ID NO: 45) |
| AGTGCAGACTACTCAATGCACGGCCGGTTCGGAAGACCCTTCCAGACTAGTTTTTCCCTGTACTAGTCCACCGGCTA (SEQ ID NO: 46) |
| AGTGCAGACTACTCAATGCACGGCCTGGTTCGTAAGACCCTTACCAGACT (SEQ ID NO: 47) |
| CGGTTGCGACATGGTGGTAAGAGCTCAGCCCGTTCCCATAGTACTATCCACAGGTCAACCT (SEQ ID NO: 48) |
| CGGTTGCGACATGGTGGTAAGAGCTCAGCCCGTTCCCATAGTACTATCCACAGGTCGCAACCT (SEQ ID NO: 49) |
| CCCGTGTAGACTACTCAATGCGGGCTGCGACATGGTGGTAAGAGCTCAGCCCGTTCCCATAGTACTATCCACGGGT (SEQ ID NO: 50) |
| CCCGTGTAGACTATTTTAGTACTATCCACGGG (SEQ ID NO: 51) |
| TGCGGGCTGCGACATGGTGGTAAGAGCTCAGCCCGTT (SEQ ID NO: 52) |
| ACCCAGGTGTAGGACGACTCAATGCCCTATTAGCTGTATCGATCCGTTTAGTCGCTCCTCCGATAGTACCCTATCCACCAGGGA (SEQ ID NO: 53) |
| ACCAGGTGGTAGACCTACTCACATGCCCTATTAGCGTGTATCGATCCGGTTTAGTCCGCTTCGATAGTAGUCCCACCAGGA (SEQ ID NO: 54) |
| CTCAATGCCTTCCATTCACCTACCGAGCTAAGCGTTCGACTTAGGTCTGTACT (SEQ ID NO: 55) |

TABLE 4

Primer regions are indicated in bold and italic

| ID | Sequence | Target |
|---|---|---|
| C.diff_F1 | ***CCAGTGTAGACTACTCAATGC***TCTTACGATCCTCACCTGCTAGCACACCCATATCCCATGC***GTACTATCCACAGGTCAACC*** (SEQ ID NO: 1) | C.diff spores |
| C.diff_G1 | ***CCAGTGTAGACTACTCAATGC***GGGTTGCGACATGGTGGTAAGAGCTCAGCCCGTTCCCATA***GTACTATCCACAGGTCAACC*** (SEQ ID NO: 2) | C.diff spores |
| C.diff_E2 | ***CCAGTGTAGACTACTCAATGC***ACGGCCTGTTCGTAAGACCCTTACAGACTAGTTTTTCCCT***GTACTATCCACAGGTCAACC*** (SEQ ID NO: 3) | C.diff spores |
| Chitinase_D10 | ***CCAGTGTAGACTACTCAATGC***CCTATTAGCTGTATCGATCCGTTTAGTCGCTCCTCCGATA***GTACTATCCACAGGTCAACC*** (SEQ ID NO: 4) | CotEC Chitinase |
| Chitinase_D11 | ***CCAGTGTAGACTACTCAATGC***CTGGTAAATCGATGACCGCTGCCTCGCCTGAGTAATCATC***GTACTATCCACAGGTCAACC*** (SEQ ID NO: 5) | CotEC Chitinase |
| CdeC.D1 | ***CCAGTGTAGACTACTCAATGC***CGTGGACTGGTCGGGTTTGGATTCGGCAGATGAATCAGTA***GTACTATCCACAGGTCAACC*** (SEQ ID NO: 6) | CdeC |
| Chitinase_H11 | ***CCAGTGTAGACTACTCAATGC***CTTGTAAGAAGAACAATCGCCGCTTCGCCTGAATAGGTTC***GTACTATCCACAGGTCAACC*** (SEQ ID NO: 7) | CotEC Chitinase |
| Chitinase_D7 | ***CCAGTGTAGACTACTCAATGC***GGACCGTTGCCTCGCCCGAGTAATCCGCCATCGCCTTTCC***GTACTATCCACAGGTCAACC*** (SEQ ID NO: 8) | CotEC Chitinase |
| CotA_B1 | ***CCAGTGTAGACTACTCAATGC***TTAAGTTCTGGGGACACGTGATGAACGCATTTAATGGGGC***GTACTATCCACAGGTCAACC*** (SEQ ID NO: 9) | CotA |
| CotA_C1 | ***CCAGTGTAGACTACTCAATGC***CGTGGACTGGTCGGGTTTGGATTCGGCAGATGAATCACTA***GTACTATCCACAGGTCAACC*** (SEQ ID NO: 10) | CotA |
| CotE_H2 | ***CCAGTGTAGACTACTCAATGC***GGCTGTGTGACTTGACCTTTGGAATGGGTGGGAGGGATGG***GTACTATCCACAGGTCAACC*** (SEQ ID NO: 11) | CotE |
| CotE_E2 | ***CCAGTGTAGACTACTCAATGC***GGTGTGGTGACCTTGACCTATGGAACCTGGTTGTA***GTACTATCCACAGGTCAACC*** (SEQ ID NO: 12) | CotE |
| CotE_D2 | ***CCAGTGTAGACTACTCAATGC***TCGACATTTCCGCCCCGACGGCCCTCCTAGTGATGGGGAGA***GTACTATCCACAGGTCAACC*** (SEQ ID NO: 13) | CotE |
| CdeM_E2 | ***CCAGTGTAGACTACTCAATGC***CTTCCATTCACCTACCGAGCTAAGCGTTCGACTTAGGTCT***GTACTATCCACAGGTCAACC*** (SEQ ID NO: 14) | CdeM |
| Chitinase_D11 | ATCGATGACCGCTGCCTCGCCTGAGTAATCATC***GTA*** (SEQ ID NO: 23) | CotEC Chitinase |
| C.diff_F1 | CCATACTCAATGCTCTTACGATCCTCATCAACC (SEQ ID NO: 24) | C.diff spores |
| C.diff_G1 | CCAGTGTAGACTACTCAATGCTCTTACGATCCTCATCAACC (SEQ ID NO: 25) | C.diff spores |
| CotE_H2 | AGTGTAGACTACTCAATGCGGCTGGCCACAGGTCAACC (SEQ ID NO: 26) | CotE |
| CotE_H2 | CTTGACCTTTGGAATGGGTGGGAGGGATGGGTACTATCCACAGGTCAACC (SEQ ID NO: 27) | CotE |
| CotE_H2 | AATGGGTGGGAGGGATGGGTACTA (SEQ ID NO: 28) | CotE |
| CotE_H2 | CTTGACCTTTGGAATGGGTAGGGAGGGAGGGATACTATCCACAGGTCAACC (SEQ ID NO: 29) | CotE |

TABLE 4-continued

| Primer regions are indicated in bold and italic | | |
|---|---|---|
| ID | Sequence | Target |
| CotE_H2 | CTTGACCTTTGGAATGGGTGGGAGGGAGGGTAT CCACAGGTCAACC (SEQ ID NO: 30) | CotE |
| CotE_D2 | ACTACTCAATGCTCGACATTTCCGCCCCGACGGC CCTCCTAGTGAGGGGAGAGTAGA (SEQ ID NO: 31) | CotE |
| CotE_D2 | ACTACTCAATGCTCGACATTTCCGCCCCGACGGC CCTCCTAGTGATGGGGAGAGTAGA (SEQ ID NO: 32) | CotE |
| CotA_C1 | ACTCAAGGCCGTGGACTGGTCGGGTTTGGATTC GGCAGATGAATCACT (SEQ ID NO: 33) | CotA |
| CotA_C1 | ACTCAAGGCCGTGGACTGGTCGGGTTTGGAT (SEQ ID NO: 34) | CotA |
| CotA_C1 | ACCCGTGGGACTGGGTCGGGTCGGG (SEQ ID NO: 35) | CotA |
| Chitinase_D11 | AACTGCCTGGTAAATCGATGACCGCTGCCTCGC CTGAGTAATCATCGTACTATCCACAGGTC (SEQ ID NO: 36) | CotEC Chitinase |
| Chitinase_D11 | GTAAATCGATGACCGCTGCCTCGCCTGAGTAATC ATOGTAC (SEQ ID NO: 37) | CotEC Chitinase |
| CdeC_D1 | ACTACTCAAACCCGTGGACTGGTCGGGTTTGGA TTCGGCAGATGAATCAGTAGAAA (SEQ ID NO: 38) | CdeC |
| CdeC_D1 | ACTACTCAATGCCGTGGACTGGTCGGGTTTGGA ATCGGCAGATGAATCAGTAGTAAA (SEQ ID NO: 39) | CdeC |
| CdeM_E2 | CCTACCGAGCTAAGCGTTCGACTTAGGTCTGTAC T (SEQ ID NO: 43) | CdeM |
| C.diff_F1 | CTCACCTGCTAGCACACCCATATCCCATGGGTAC AATCCACAGGTCAA (SEQ ID NO: 44) | C.diff spores |
| C.diff_F1 | CTCACCTGCTAGCACACCCACATCCCGTGCGTGC TATCCACAGGTGAA (SEQ ID NO: 45) | C.diff spores |
| C.diff_E2 | AGTGCAGACTACTCAATGCACGGCCGGTTCGGAA GACCCTTCCAGACTAGTTTTTCCCTGTACTAGT CCACCGGCTA (SEQ ID NO: 46) | C.diff spores |
| C.diff_E2 | AGTGCAGACTACTCAATGCACGGCCTGGTTCGT AAGACCCTTACCAGACT (SEQ ID NO: 47) | C.diff spores |
| C.diff_G1 | CGGTTGCGACATGGTGGTAAGAGCTCAGCCCGT TCCCATAGTACTATCCACAGGTCAACCT (SEQ ID NO: 48) | C.diff spores |
| C.diff_G1 | CGGTTGCGACATGGTGGTAAGAGCTCAGCCCGT TCCCATAGTACTATCCACAGGTCGCAACCT (SEQ ID NO: 49) | C.diff spores |
| C.diff_G1 | CCCGTGTAGACTACTCAATGCGGGCTGCGACAT GGTGGTAAGAGCTCAGCCCGTTCCCATAGTACT ATCCACGGGT (SEQ ID NO: 50) | C.diff spores |
| C.diff_G1 | CCCGTGTAGACTATTTTAGTACTATCCACGGG (SEQ ID NO: 51) | C.diff spores |
| C.diff_G1 | TGCGGGCTGCGACATGGTGGTAAGAGCTCAGCC CGTT (SEQ ID NO: 52) | C.diff spores |
| Chitinase_D10 | ACCCAGGTGTAGGACGACTCAATGCCCTATTAGC TGTATCGATCCGTTTAGTCGCTCCTCCGATAGTA CCCTATCCACCAGGGA (SEQ ID NO: 53) | CotEC Chitinase |

TABLE 4-continued

Primer regions are indicated in bold and italic

| ID | Sequence | Target |
|---|---|---|
| Chitinase_D10 | ACCAGGTGGTAGACCTACTCACATGCCCTATTAG CGTGTATCGATCCGGTTTAGTCCGCTTCGATAGT AGUCCCACCAGGA (SEQ ID NO: 54) | CotEC Chitinase |
| CdeM_E2 | CTCAATGCCTTCCATTCACCTACCGAGCTAAGCG TTCGACTTAGGTCTGTACT (SEQ ID NO: 55) | CdeM |

In an embodiment, the aptamer specifically binds to a target as defined herein. The term "target" as used herein is used to relate to molecule selected from a *C. difficile* CotA protein, *C. difficile* CotE protein, *C. difficile* CdeC protein, *C. difficile* CdeM protein, *C. difficile* CotEC chitinase protein and a *C. difficile* spore.

In an embodiment, the aptamer specifically binds to an epitope in a *C. difficile* CotA protein.

In an embodiment, the aptamer specifically binds to an epitope in a *C. difficile* CotE protein.

In an embodiment, the aptamer specifically binds to an epitope in a *C. difficile CdeC protein.*

In an embodiment, the aptamer specifically binds to an epitope in a *C. difficile* CdeM protein.

In an embodiment, the aptamer specifically binds to an epitope in a *C. difficile* CotEC chitinase protein.

In an embodiment, the aptamer specifically binds to an epitope on a surface of a *C. difficile* spore.

An aptamer binds "specifically" to a target as defined herein if the aptamer binds with preferential or high affinity to the target, but does not bind or binds with only low affinity to other structurally related molecules (e.g. *Bacillus subtilis* spores.) In some embodiments, the dissociation constant for the target protein is in the micro-molar range. In some embodiments, the dissociation constant for the target protein is in the nano-molar (nM) range. In some embodiments, the dissociation constant for the target protein is in the pico-molar (pM) range. In some embodiments, the dissociation constant is about 0.1 nM or less. In some embodiments, the dissociation constant is about 0.1 nM to about 1 nM. In some embodiments, the dissociation constant is about 1 nM to about 10 nM. In some embodiments, the dissociation constant is about 10 nM to about 100 nM. In some embodiments, the dissociation constant is about 100 nM to about 1000 nM. Lower affinity binding may refer to binding that occurs at less affinity than to a target protein. Lower affinity binding may refer to binding that occurs at less affinity than to a target. The lower affinity binding may be selected from the range of less than 1 fold to 2 fold, less than 2 fold to 5 fold, less than 5 fold to 10 fold, less than 10 fold to 50 fold, less than 100 fold to 1000 fold, less than 1000 fold to 10000 fold, or less than 10000 fold to 100000 fold of binding to the target.

Aptamers

The aptamers described herein are small artificial ligands, compromising DNA, RNA or modifications thereof, capable of specifically binding to a target as defined herein with high affinity and specificity.

As used herein, "aptamer", "nucleic acid molecule" or "oligonucleotide" are used interchangeably to refer to a non-naturally occurring nucleic acid molecule that has a desirable action on a target as defined herein.

The aptamers of the disclosure may be DNA aptamers. For example, the aptamers may be formed from single-stranded DNA (ssDNA). Alternatively, the aptamers of the disclosure may be RNA aptamers. For example, the aptamers can be formed from single-stranded RNA (ssRNA).

In certain embodiments, the aptamers are RNA aptamers and comprise a sequence in which of one or some or all of the deoxyribonucleotides in any of the sequences set forth in SEQ. ID NOs. 1 to 14, 23 to 39, 42 to 55 are substituted for their equivalent ribonucleotide residues AMP, GMP, UMP or CMP.

The aptamers of the disclosure may comprise modified nucleic acids as described herein.

In certain embodiments, the aptamers of the disclosure are prepared using principles of in vitro selection known in the art, that include iterative cycles of target binding, partitioning and preferential amplification of target binding sequences. Selection may be performed using immobilized target proteins. Immobilization may include, but is not limited to, immobilization to a solid surface. In a non-limiting example, the solid surface may be beads. In a non-limiting example, the solid surface may be magnetic beads.

Non-limiting examples of amplification methods include polymerase chain reaction (PCR), ligation amplification (or ligase chain reaction, LCR), strand displacement amplification, nucleic acid sequence-based amplification, and amplification methods based on the use of Q-beta replicase. In a non-limiting embodiment, at least one type of aptamer may be immobilized on a solid surface during amplification. Each of these exemplary methods is well known in the art.

In embodiments, the aptamers are selected from a nucleic acid molecule library such as a single-stranded DNA or RNA nucleic acid molecule library. Typically, the aptamers are selected from a "universal aptamer selection library" that is designed such that any selected aptamers need little to no adaptation to convert into any of the listed assay formats.

Once selected, the aptamer may be further modified before being used e.g. to remove one or both primer sequences and/or parts of the randomised not required for target binding.

Typically, aptamers for use in the disclosure comprise a first primer region (e.g. at the 5' end), a second primer region (e.g. at the 3' end), or both. The primer regions may serve as primer binding sites for PCR amplification of the library and selected aptamers.

The skilled person would understand different primer sequences can be selected depending, for example, on the starting library and/or aptamer selection protocol. In an embodiment, aptamers may comprise SEQ ID NO: 21 and/or 22. In other embodiments, any one of one to all of the nucleotides disclosed by SEQ ID NO: 21 or 22 may be modified. The primer region length may also be varied.

The first primer region and/or second region may comprise a detectable label as described herein. In an embodiment, the first and/or second primer region may be fluorescently labelled. Non-limiting examples of fluorescent labels include but are not limited to fluorescein, green fluorescent protein (GFP), yellow fluorescent protein, cyan fluorescent protein, and others. In an embodiment, a fluorescein label is used. In embodiments, other forms of detecting the primer may be used, including but not limited to phosphate ($PO_4$) labelling, isotope labelling, electrochemical sensors, colorimetric biosensors, and others.

In embodiments, the aptamers of the disclosure comprise or consist of a nucleic acid sequence selected from any one of SEQ ID NOs: 1 to 14, 23 to 39 or 43 to 55.

In certain embodiments, aptamers of the disclosure comprise or consist of a nucleic acid sequence having at least 85%, at least 90%, at least 95%, at least 96%, at least 97%, at least 98%, at least 99% or more sequence identity to the nucleotide sequence of any one of SEQ ID NOs: 1 to 14, 23 to 39 or 43 to 55.

As used herein, "sequence identity" refers to the percentage of nucleotides in a candidate sequence that are identical with the nucleotides in said sequences after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, CLUSTALW or Megalign (DNASTAR) software. For example, % nucleic acid sequence identity values can be generated using sequence comparison computer programs found on the European Bioinformatics Institute website (www.ebi.ac.uk).

As used herein, when describing the percent identity of a nucleic acid, such as an aptamer, the sequence of which is at least, for example, about 90% identical to a reference nucleotide sequence, it is intended that the nucleic acid sequence is identical to the reference sequence except that the nucleic acid sequence may include up to ten-point mutations (e.g. substitution, deletion, insertion) per each 100 nucleotides of the reference nucleic acid sequence. These mutations may occur at the 5' or 3' terminal positions of the reference nucleotide sequence or anywhere between those 5' or 3' terminal positions, interspersed either individually among nucleotides in the reference sequence or in one or more contiguous groups within the reference sequence.

In embodiments, aptamers comprise, consist essentially of, or consist of a minimal effective fragment of SEQ ID NOs: 1 to 14, 23 to 39 or 43 to 55. Herein, a "minimal effective fragment" is understood to mean a fragment (e.g. portion) of the full-length aptamer capable of binding to a target as defined herewith with the same or improved affinity as compared to the full-length aptamer. A minimal effective fragment may compete for binding to a target as defined herein with the full-length aptamer.

In embodiments, the aptamers of the disclosure comprise, consist essentially of, or consist of at least 10 contiguous nucleic acid residues of any of the sequences as set forth in any one of SEQ ID NOs: 1 to 14, 23 to 39 or 43 to 55 and show equivalent or improved binding to the target molecule. In embodiments, the aptamers of the disclosure comprise, consist essentially of, or consist of at least 10 contiguous nucleic acid residues of any of the sequences as set forth in any one of SEQ ID NOs: 1 to 14, 23 to 39 or 43 to 55 and show adequate binding to the target molecule. Adequate binding includes binding to target molecule that occurs with affinity and specificity as described herein, or an affinity and/or specificity of binding less than that of the full-length aptamer sequence above but still capable of delivering a report of the presence of its respective target.

In embodiments, the aptamers of the disclosure comprise, consist essentially of, or consist of at least 20 contiguous nucleic acid residues of any of the sequences as set forth in any one of SEQ ID NOs: 1 to 14, 23 to 39 or 43 to 55 and show equivalent or improved binding to the target molecule. In embodiments, the aptamers of the disclosure comprise, consist essentially of, or consist of at least 20 contiguous nucleic acid residues of any of the sequences as set forth in any one of SEQ ID NOs: 1 to 14, 23 to 39 or 43 to 55 and show adequate binding to the target molecule. Adequate binding includes binding to target molecule that occurs with affinity and specificity as described herein, or an affinity and/or specificity of binding less than that of the full-length aptamer sequence above but still capable of delivering a report of the presence of its respective target.

In embodiments, an aptamer of the disclosure comprise, consists essentially of, or consist of at least 24 contiguous nucleotides of any of the sequences as set forth in any one of SEQ ID NOs: 1 to 14, 23 to 39 or 43 to 55.

In some embodiments, an aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 1. The aptamer may comprise, consist essentially of, or consist of any span of contiguous nucleotides from SEQ ID NO: 1, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 2. The aptamer may comprise, consist essentially of, or consist of any span of contiguous nucleotides from SEQ ID NO: 2, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 3. The aptamer may comprise, consists essentially of, or consist of any span of contiguous nucleotides from SEQ ID NO: 3, where the span has a length chosen in one nucleotide increments from 25 nucleotides to full length. The aptamer may comprise, consists essentially of, or consist of any span of contiguous nucleotides from SEQ ID NO: 3, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 4. The aptamer may comprise, consists essentially of, or consist of any span of contiguous nucleotides from SEQ ID NO: 4, where the span has a length chosen in one nucleotide increments from 25 nucleotides to full length. The aptamer may comprise, consists essentially of, or consist of any span of contiguous nucleotides from SEQ ID NO: 4, where the span has a length chosen in one nucleotide increments from 25 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 5. The aptamer may comprise, consists essentially of, or consist of any span of contiguous nucleotides from SEQ ID NO: 5, where the span has a length chosen in one nucleotide increments from 25 nucleotides to full length. The aptamer may comprise, consists essentially of, or consist of any span of contiguous nucleotides from SEQ ID NO: 5, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO:. 6. The aptamer may comprise, consists essentially of, or consist of any span of contiguous nucleotides from SEQ ID NO: 6, where the span has a length chosen in one nucleotide increments from 25 nucleotides to full length. The aptamer may comprise, consists essentially of, or consist of any span of contiguous nucleotides from SEQ ID NO: 6, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleic acid molecules as comprised in the nucleic acid sequence of SEQ ID NO: 7. The aptamer may comprise, consists essentially of, or consist of any span of contiguous nucleotides from SEQ ID NO: 7, where the span has a length chosen in one nucleotide increments from 25 nucleotides to full length. The aptamer may comprise, consists essentially of, or consist of any span of contiguous nucleotides from SEQ ID NO: 7, where the span has a length chosen in one nucleotide increments from 10 nucleotides to full length.

In embodiments, the aptamer comprises, consists essentially of, or consists of 25, 26, 27, 28, 29 30, 31, 32, 33, 34, 35, 36, 37, 38, 39 or 40 contiguous nucleotides in the nucleic acid sequence of SEQ ID NO: 8. The aptamer may comprise, consists essentially of, or consist of any span of contiguous nucleotides from SEQ ID NO: 8, where the span has a length chosen in one nucleotide increments from 25 nucleotides to full length. The aptamer may comprise, consists essentially of, or consist of any span of contiguous nucleotides from SEQ ID NO: 8, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 9. The aptamer may comprise, consists essentially of, or consist of any span of contiguous nucleotides from SEQ ID NO: 9, where the span has a length chosen in one nucleotide increments from 25 nucleotides to full length. The aptamer may comprise, consists essentially of, or consist of any span of contiguous nucleotides from SEQ ID NO: 9, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 10. The aptamer may comprise, consists essentially of, or consist of any span of contiguous nucleotides from SEQ ID NO: 10, where the span has a length chosen in one nucleotide increments from 25 nucleotides to full length. The aptamer may comprise, consists essentially of, or consist of any span of contiguous nucleotides from SEQ ID NO: 10, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 11. The aptamer may comprise, consists essentially of, or consist of any span of contiguous nucleotides from SEQ ID NO: 11, where the span has a length chosen in one nucleotide increments from 25 nucleotides to full length. The aptamer may comprise, consists essentially of, or consist of any span of contiguous nucleotides from SEQ ID NO: 11, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or 76 contiguous nucleotides in the nucleic acid sequence of SEQ ID NO: 12. The aptamer may comprise, consists essentially of, or consist of any span of contiguous nucleotides from SEQ ID NO: 12, where the span has a length chosen in one nucleotide increments from 25 nucleotides to full length. The aptamer may comprise, consists essentially of, or consist of any span of contiguous nucleotides from SEQ ID NO: 12, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, or 82 nucleotides in the nucleic acid sequence of SEQ ID NO: 13. The aptamer may comprise, consists essentially of, or consist of any span of contiguous nucleotides from SEQ ID NO: 13, where the span has a length chosen in one nucleotide increments from 25 nucleotides to full length. The aptamer may comprise, consists essentially of, or consist of any span of contiguous nucleotides from SEQ ID NO: 13, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 14. The aptamer may comprise, consists essentially of, or consist of any span of contiguous nucleotides from SEQ ID NO: 14, where the span has a length chosen in one nucleotide increments from 14 nucleotides to full length. The aptamer may comprise, consists essentially of, or consist of any span of contiguous nucleotides from SEQ ID NO: 14, where the span has a length chosen in one nucleotide increments from 10 nucleotides to full length.

In embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, or 36 contiguous nucleotides in the nucleic acid sequence of SEQ ID NO: 23. The aptamer may comprise, consists essentially of, or consist of any span of contiguous nucleotides from SEQ ID NO: 23, where the span has a length chosen in one nucleotide increments from 25 nucleotides to full length. The aptamer may comprise, consists essentially of, or consist of any span of contiguous nucleotides from SEQ ID NO: 23, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32 or 33 contiguous nucleotides in the nucleic acid sequence of SEQ ID NO: 24. The aptamer may comprise, consists essentially of, or consist of any span of contiguous nucleotides from SEQ ID NO: 24, where the span has a length chosen in one nucleotide increments from 25 nucleotides to full length. The aptamer may comprise, consist essentially of, or consist of any span of contiguous nucleotides from SEQ ID NO: 24, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 contiguous nucleotides in the nucleic acid sequence of SEQ ID NO: 25. The aptamer may comprise, consists essentially of, or consist of any span of contiguous nucleotides from SEQ ID NO: 25, where the span has a length chosen in one nucleotide increments from 25 nucleotides to full length. The aptamer may comprise, consist essentially of, or consist of any span of contiguous nucleotides from SEQ ID NO: 25, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, or 38 contiguous nucleotides in the nucleic acid sequence of SEQ ID NO: 26. The aptamer may comprise, consists essentially of, or consist of any span of contiguous nucleotides from SEQ ID NO: 26, where the span has a length chosen in one nucleotide increments from 25 nucleotides to full length. The aptamer may comprise, consist essentially of, or consist of any span of contiguous nucleotides from SEQ ID NO: 26, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides in the nucleic acid sequence of SEQ ID NO: 27. The aptamer may comprise, consists essentially of, or consist of any span of contiguous nucleotides from SEQ ID NO: 27, where the span has a length chosen in one nucleotide increments from 25 nucleotides to full length. The aptamer may comprise, consist essentially of, or consist of any span of contiguous nucleotides from SEQ ID NO: 27, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, or 24 contiguous nucleotides in the nucleic acid sequence of SEQ ID NO: 28. The aptamer may comprise, consist essentially of, or consist of any span of contiguous nucleotides from SEQ ID NO: 28, where the span has a length chosen in one nucleotide increments from 15 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 contiguous nucleotides in the nucleic acid sequence of SEQ ID NO: 29. The aptamer may comprise, consists essentially of, or consist of any span of contiguous nucleotides from SEQ ID NO: 29, where the span has a length chosen in one nucleotide increments from 25 nucleotides to full length. The aptamer may comprise, consist essentially of, or consist of any span of contiguous nucleotides from SEQ ID NO: 29, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 contiguous nucleotides in the nucleic acid sequence of SEQ ID NO: 30. The aptamer may comprise, consists essentially of, or consist of any span of contiguous nucleotides from SEQ ID NO: 30, where the span has a length chosen in one nucleotide increments from 25 nucleotides to full length. The aptamer may comprise, consist essentially of, or consist of any span of contiguous nucleotides from SEQ ID NO: 30, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 contiguous nucleotides in the nucleic acid sequence of SEQ ID NO: 31. The aptamer may comprise, consists essentially of, or consist of any span of contiguous nucleotides from SEQ ID NO: 31, where the span has a length chosen in one nucleotide increments from 25 nucleotides to full length. The aptamer may comprise, consist essentially of, or consist of any span of contiguous nucleotides from SEQ ID NO: 31, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, or 58 contiguous nucleotides in the nucleic acid sequence of SEQ ID NO: 32. The aptamer may comprise, consists essentially of, or consist of any span of contiguous nucleotides from SEQ ID NO: 24, where the span has a length chosen in one nucleotide increments from 32 nucleotides to full length. The aptamer may comprise, consist essentially of, or consist of any span of contiguous nucleotides from SEQ ID NO: 32, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 contiguous nucleotides in the nucleic acid sequence of SEQ ID NO: 33. The aptamer may comprise, consists essentially of, or consist of any span of contiguous nucleotides from SEQ ID NO: 33, where the span has a length chosen in one nucleotide increments from 25 nucleotides to full length. The aptamer may comprise, consist essentially of, or consist of any span of contiguous nucleotides from SEQ ID NO: 33, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, or 31 contiguous nucleotides in the nucleic acid sequence of SEQ ID NO: 34. The aptamer may comprise, consists essentially of, or consist of any span of contiguous nucleotides from SEQ ID NO: 34, where the span has a length chosen in one nucleotide increments from 25 nucleotides to full length. The aptamer may comprise, consist essentially of, or consist of any span of contiguous nucleotides from SEQ ID NO: 34, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, or 25 contiguous nucleotides in the nucleic acid sequence of SEQ ID NO: 35. The aptamer may comprise, consist essentially of, or consist of any span of contiguous nucleotides from SEQ ID NO: 35, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 contiguous nucleotides in the nucleic acid sequence of SEQ ID NO: 36. The aptamer may comprise, consists essentially of, or consist of any span of contiguous nucleotides from SEQ ID NO: 36, where the span has a length chosen in one nucleotide increments from 25 nucleotides to full length. The aptamer may comprise, consist essentially of, or consist of any span of contiguous nucleotides from SEQ ID NO: 36, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 contiguous nucleotides in the nucleic acid sequence of SEQ ID NO: 37. The aptamer may comprise, consists essentially of, or consist of any span of contiguous nucleotides from SEQ ID NO: 37, where the span has a length chosen in one nucleotide increments from 25 nucleotides to full length. The aptamer may comprise, consist essentially of, or consist of any span of contiguous nucleotides from SEQ ID NO: 37, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 contiguous nucleotides in the nucleic acid sequence of SEQ ID NO: 38. The aptamer may comprise, consists essentially of, or consist of any span of contiguous nucleotides from SEQ ID NO: 38, where the span has a length chosen in one nucleotide increments from 25 nucleotides to full length. The aptamer may comprise, consist essentially of, or consist of any span of contiguous nucleotides from SEQ ID NO: 38, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, or 57 contiguous nucleotides in the nucleic acid sequence of SEQ ID NO: 39. The aptamer may comprise, consists essentially of, or consist of any span of contiguous nucleotides from SEQ ID NO: 39, where the span has a length chosen in one nucleotide increments from 25 nucleotides to full length. The aptamer may comprise, consist essentially of, or consist of any span of contiguous nucleotides from SEQ ID NO: 39, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, or 35 contiguous nucleotides in the nucleic acid sequence of SEQ ID NO: 43. The aptamer may comprise, consists essentially of, or consist of any span of contiguous nucleotides from SEQ ID NO: 43, where the span has a length chosen in one nucleotide increments from 25 nucleotides to full length. The aptamer may comprise, consist essentially of, or consist of any span of contiguous nucleotides from SEQ ID NO: 43, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 contiguous nucleotides in the nucleic acid sequence of SEQ ID NO: 44. The aptamer may comprise, consists essentially of, or consist of any span of contiguous nucleotides from SEQ ID NO: 44, where the span has a length chosen in one nucleotide increments from 25 nucleotides to full length. The aptamer may comprise, consist essentially of, or consist of any span of contiguous nucleotides from SEQ ID NO: 44, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 contiguous nucleotides in the nucleic acid sequence of SEQ ID NO: 45. The aptamer may comprise, consists essentially of, or consist of any span of contiguous nucleotides from SEQ ID NO: 45, where the span has a length chosen in one nucleotide increments from 25 nucleotides to full length. The aptamer may comprise, consist essentially of, or consist of any span of contiguous nucleotides from SEQ ID NO: 45, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, or 77 contiguous nucleotides in the nucleic acid sequence of SEQ ID NO: 46. The aptamer may comprise, consists essentially of, or consist of any span of contiguous nucleotides from SEQ ID NO: 46, where the span has a length chosen in one nucleotide increments from 25 nucleotides to full length. The aptamer may comprise, consist essentially of, or consist of any span of contiguous nucleotides from SEQ ID NO: 46, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 contiguous nucleotides in the nucleic acid sequence of SEQ ID NO: 47. The aptamer may comprise, consists essentially of, or consist of any span of contiguous nucleotides from SEQ ID NO: 47, where the span has a length chosen in one nucleotide increments from 25 nucleotides to full length. The aptamer may comprise, consist essentially of, or consist of any span of contiguous nucleotides from SEQ ID NO: 47, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 contiguous nucleotides in the nucleic acid sequence of SEQ ID NO: 48. The aptamer may comprise, consists essentially of, or consist of any span of contiguous nucleotides from SEQ ID NO: 48, where the span has a length chosen in one nucleotide increments from 25 nucleotides to full length. The aptamer may comprise, consist essentially of, or consist of any span of contiguous nucleotides from SEQ ID NO: 48, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 contiguous nucleotides in the nucleic acid sequence of SEQ ID NO: 49. The aptamer may comprise, consists essentially of, or consist of any span of contiguous nucleotides from SEQ ID NO: 49, where the span has a length chosen in one nucleotide increments from 25 nucleotides to full length. The aptamer may comprise, consist essentially of, or consist of any span of contiguous nucleotides from SEQ ID NO: 49, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or 76 contiguous nucleotides in the nucleic acid sequence of SEQ ID NO: 50. The aptamer may comprise, consists essentially of, or consist of any span of contiguous nucleotides from SEQ ID NO: 50, where the span has a length chosen in one nucleotide increments from 25 nucleotides to full length. The aptamer may comprise, consist essentially of, or consist of any span of contiguous nucleotides from SEQ ID NO: 50, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, or 32 contiguous nucleotides in the nucleic acid sequence of SEQ ID NO: 51. The aptamer may comprise, consists essentially of, or consist of any span of contiguous nucleotides from SEQ ID NO: 51, where the span has a length chosen in one nucleotide increments from 25 nucleotides to full length. The aptamer may comprise, consist essentially of, or consist of any span of contiguous nucleotides from SEQ ID NO: 51, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, or 37 contiguous nucleotides in the nucleic acid sequence of SEQ ID NO: 52. The aptamer may comprise, consists essentially of, or consist of any span of contiguous nucleotides from SEQ ID NO: 52, where the span has a length chosen in one nucleotide increments from 25 nucleotides to full length. The aptamer may comprise, consist essentially of, or consist of any span of contiguous nucleotides from SEQ ID NO: 52, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84 contiguous nucleotides in the nucleic acid sequence of SEQ ID NO: 53. The aptamer may comprise, consists essentially of, or consist of any span of contiguous nucleotides from SEQ ID NO: 53, where the span has a length chosen in one nucleotide increments from 25 nucleotides to full length. The aptamer may comprise, consist essentially of, or consist of any span of contiguous nucleotides from SEQ ID NO: 53, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 contiguous nucleotides in the nucleic acid sequence of SEQ ID NO: 54. The aptamer may comprise, consists essentially of, or consist of any span of contiguous nucleotides from SEQ ID NO: 54, where the span has a length chosen in one nucleotide increments from 25 nucleotides to full length. The aptamer may comprise, consist essentially of, or consist of any span of contiguous nucleotides from SEQ ID NO: 54, where the span has a length chosen in one nucleotide increments from 10 nucleotides to full length.

In some embodiments, the aptamer comprises, consists essentially of, or consists of 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, or 53 contiguous nucleotides in the nucleic acid sequence of SEQ ID NO: 55. The aptamer may comprise, consists essentially of, or consist of any span of contiguous nucleotides from SEQ ID NO: 55, where the span has a length chosen in one nucleotide increments from 25 nucleotides to full length. The aptamer may comprise, consist essentially of, or consist of any span of contiguous nucleotides from SEQ ID NO: 55, where the span has a length chosen in one nucleotide increments from 10 nucleotides to full length.

These sequences relate to aptamer fragments with equivalent, suitable, or improved binding to a target as described herein as compared to full-length aptamer.

In embodiments, aptamers comprise, consist essentially of, or consist of a nucleic acid sequence comprising at least about 10, 15, 20, 25, 30, 35, 40, 45, 50, 51, 52, 53, 54, 55, 60, 65, 70, 75, 80 or more consecutive nucleotides of a sequence having at least 85%, at least 90%, at least 95%, at least 96%, at least 97%, at least 98%, at least 99% or more identity with any of SEQ ID NOs: 1 to 11, 13 to 14, or 53 to 54. In embodiments, aptamers comprise, consist essentially of, or consist of a nucleic acid sequence comprising at least about 10, 15, 20, 25, 30, 35, 40, 45, 50, 51, 52, 53, 54, 55, 60, 65, 70, 75 or more consecutive nucleotides of a sequence having at least 85%, at least 90%, at least 95%, at least 96%, at least 97%, at least 98%, at least 99% or more identity with any of SEQ ID Nos: 12, 46 or 50. In embodiments, aptamers comprise, consist essentially of, or consist of a nucleic acid sequence comprising at least about 10, 15, 20, 25, 30, 35, 40, 45, 50, 51, 52, 53, 54, 55, 60, or more consecutive nucleotides of a sequence having at least 85%, at least 90%, at least 95%, at least 96%, at least 97%, at least 98%, at least 99% or more identity with any of SEQ ID Nos: 36, 48 or 49. In embodiments, aptamers comprise, consist essentially of, or consist of a nucleic acid sequence comprising at least about 10, 15, 20, 25, 30, 35, 40, 45, 50, 51, 52, 53, 54, 55, 60, or more consecutive nucleotides of a sequence having at least 85%, at least 90%, at least 95%, at least 96%, at least 97%, at least 98%, at least 99% or more identity with any of SEQ ID Nos: 29, 31, 32, 38, 39, 47 or 55. In embodiments, aptamers comprise, consist essentially of, or consist of a nucleic acid sequence comprising at least about 10, 15, 20, 25, 30, 35, 40, 45, 50, or more consecutive nucleotides of a sequence having at least 85%, at least 90%, at least 95%, at least 96%, at least 97%, at least 98%, at least 99% or more identity with any of SEQ ID Nos: 27, 29, 31, 32, 38, 39, 47, or 55. In embodiments, aptamers comprise, consist essentially of, or consist of a nucleic acid sequence comprising at least about 10, 15, 20, 25, 30, 35, 40 or more consecutive nucleotides of a sequence having at least 85%, at least 90%, at least 95%, at least 96%, at least 97%, at least 98%, at least 99% or more identity with any of SEQ ID Nos: 25, 30, 37, 44, or 45. In embodiments, aptamers comprise, consist essentially of, or consist of a nucleic acid sequence comprising at least about 10, 15, 20, 25, 30 or more consecutive nucleotides of a sequence having at least 85%, at least 90%, at least 95%, at least 96%, at least 97%, at least 98%, at least 99% or more identity with any of SEQ ID Nos: 23, 24, 26, 34, 43, 51, or 52. In embodiments, aptamers comprise, consist essentially of, or consist of a nucleic acid sequence comprising at least about 10, 15, 20 or more consecutive nucleotides of a sequence having at least 85%, at least 90%, at least 95%, at least 96%, at least 97%, at least 98%, at least 99% or more identity with any of SEQ ID Nos: 28 or 35. In this context the term "about" typically means the referenced nucleotide sequence length plus or minus 10% of that referenced length.

Aspects of the disclosure relate to a composition comprising two or more aptamers or combination comprising two or more aptamers. Embodiments relate to a composition or combination comprising two or more aptamers, wherein each of the two or more aptamers are independently selected from an aptamer which comprises or consists essentially of a nucleic acid sequence selected from the group consisting of: SEQ. ID. No: 1; SEQ. ID. No: 2; SEQ. ID. No: 3; SEQ. ID. No: 4; SEQ. ID. No: 5; SEQ. ID. No: 6; SEQ. ID. No: 7; SEQ. ID. No: 8; SEQ. ID. No: 9; SEQ. ID. No: 10; SEQ. ID. No: 11; SEQ. ID. No: 12; SEQ. ID. No: 13; SEQ. ID. No: 14; SEQ. ID. No: 23; SEQ. ID. No: 24; SEQ. ID. No: 25; SEQ. ID. No: 26; SEQ. ID. No: 27; SEQ. ID. No: 28; SEQ. ID. No: 29; SEQ. ID. No: 30; SEQ. ID. No: 31; SEQ. ID. No: 32; SEQ. ID. No: 33; SEQ. ID. No: 34; SEQ. ID. No: 35; SEQ. ID. No: 36; SEQ. ID. No: 37; SEQ. ID. No: 38; SEQ. ID. No: 39; SEQ. ID. No: 42; SEQ. ID. No: 43; SEQ. ID. No: 44; SEQ. ID. No: 45; SEQ. ID. No: 46; SEQ. ID. No: 47; SEQ. ID. No: 48; SEQ. ID. No: 49; SEQ. ID. No: 50; SEQ. ID. No: 51; SEQ. ID. No: 52; SEQ. ID. No: 53; SEQ. ID. No: 54; and SEQ. ID. No: 55; or an aptamer comprising or consisting essentially of a nucleic acid sequence which has at least 90%, e.g. 95%, 96%, 97%, 98%, 99% sequence identity with any of SEQ. ID. No. 1 to 14, 23 to 39 and 42 to 55.

Embodiments relate to a composition or combination comprising two or more aptamers wherein one of the two or more aptamers comprises or consists essentially of a nucleic acid sequence as set forth in SEQ. ID. No. 55 and the composition or combination further comprises one or more aptamers which comprise or consist essentially of a nucleic acid sequence as set forth in SEQ. ID. No. 1 to 14, 23 to 39 and 43 to 54.

Embodiments relate to a composition or combination comprising three or more aptamers, wherein each aptamer is independently selected from an aptamer which comprises or consists essentially of a nucleic acid sequence as set forth in SEQ. ID. No. 1 to 14 and 23 to 39 and 43 to 55.

Embodiments relate to a composition or combination which comprises or consists essentially of a nucleic acid sequence as set forth in SEQ. ID. No. 55 and which further comprises two or more aptamers which are independently selected from an aptamer which comprises or consists essentially of a nucleic acid sequence as set forth in SEQ. ID. No. 1 to 14, 23 to 39 and 43 to 54.

Embodiments relate to a composition or combination of three or more aptamers, wherein each aptamer comprises or consists essentially of a nucleic acid sequence as set forth in 1 to 14, 23 to 39 and 43 to 55 or an aptamer comprising or consisting essentially of a nucleic acid sequence which has at least 90%, e.g. 95%, 96%, 97%, 98%, 99% sequence identity with any of SEQ. ID. No. 1 to 14, 23 to 39 and 43 to 55.

Embodiments relate to a composition or combination comprising two or more aptamers wherein one of the two or more aptamers comprises or consist essentially of a nucleic acid sequence as set forth in SEQ. ID. No. 1 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 2 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 3 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 4 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 5 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 6 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 7 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 8 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 9 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 10 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 11 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 12 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 13 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 14 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 23 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 24 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 25 and optionally wherein a second of the two or more aptamers comprises or consist essentially of a nucleic acid sequence as set forth in SEQ. ID. No.

55.

Embodiments relate to a composition or combination comprising two or more aptamers wherein one of the two or more aptamers comprises or consist essentially of a nucleic acid sequence as set forth in SEQ. ID. No. 26 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 27 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 28 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 29 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 30 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 31 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 32 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 33 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 34 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 35 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 36 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 37 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 38 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 39 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 43 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 44 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 45 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 46 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 47 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 48 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 49 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 50 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 51 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 52 and optionally wherein a second of the two or more aptamers comprises or consist essentially of a nucleic acid sequence as set forth in SEQ. ID. No. 55. Embodiments relate to a composition or combination comprising two or more aptamers wherein one of the two or more aptamers comprises or consist essentially of a nucleic acid sequence as set forth in SEQ. ID. No. 53 and optionally wherein a second of the two or more aptamers comprises or consist essentially of a nucleic acid sequence as set forth in SEQ. ID. No. 55.

Embodiments relate to a composition or combination comprising two or more aptamers wherein one of the two or more aptamers comprises or consist essentially of a nucleic acid sequence as set forth in SEQ. ID. No. 54 and optionally wherein a second of the two or more aptamers comprises or consist essentially of a nucleic acid sequence as set forth in SEQ. ID. No. 55.

Embodiments relate to a composition or combination which comprise the following aptamers: CotE H2.1.2 (SEQ ID NO: 30); CotE D2.1 (SEQ ID NO: 31); CotA C1.1 (SEQ ID NO: 33); and CotEC Chitinase (SEQ ID NO: 36). The aptamers may comprise natural or non-natural nucleotides and/or base derivatives (or combinations thereof). In embodiments, the aptamers comprise one or more modifications such that they comprise a chemical structure other than deoxyribose, ribose, phosphate, adenine (A), guanine (G), cytosine (C), thymine (T), or uracil (U). The aptamers may be modified at the nucleobase, at the sugar or at the phosphate backbone.

In embodiments, the aptamers comprise one or more modified nucleotides. Exemplary modifications include for example nucleotides comprising an alkylation, arylation or acetylation, alkoxylation, halogenation, amino group, or another functional group. Examples of modified nucleotides include, but are not limited to, 2'-fluoro ribonucleotides, 2'-NH 2-, 2'-OCH 3- and 2'-O-methoxyethyl ribonucleotides, which are used for RNA aptamers.

The aptamers may be wholly or partly phosphorothioate or DNA, phosphorodithioate or DNA, phosphoroselenoate or DNA, phosphorodiselenoate or DNA, locked nucleic acid (LNA), peptide nucleic acid (PNA), N3'-P5'phosphoramidate RNA/DNA, cyclohexene nucleic acid (CeNA), tricyclo DNA (tcDNA) or spiegelmer, or the phosphoramidate morpholine (PMO) components or any other modification known to those skilled in the art (see also Chan et al., Clinical and Experimental Pharmacology and Physiology (2006) 33, 533-540).

Some of the modifications may allow the aptamers to be stabilized against nucleic acid-cleaving enzymes. In the stabilization of the aptamers, a distinction can generally be made between the subsequent modification of the aptamers and the selection with already modified RNA/DNA. The stabilization may not affect the affinity of the modified RNA/DNA aptamers but may prevent the rapid decomposition of the aptamers in an organism, biological solutions, or solutions, by RNases/DNases. An aptamer is referred to as stabilized if the half-life of the aptamer in the sample (e.g. biological medium, organism, solution) is greater than one minute, greater than one hour, or greater than one day. The aptamers may be modified with reporter molecules, which may enable detection of the labelled aptamers. Reporter molecules may also contribute to increased stability of the aptamers.

Aptamers form a three-dimensional structure that depends on their nucleic acid sequence. The three-dimensional structure of an aptamer may arise due to Watson and Crick intramolecular base pairing, Hoogsteen base pairing (quadruplex), wobble-pair formation, or other non-canonical base interactions. This structure enables aptamers, analogous to antigen-antibody binding, to bind target structures accurately. A nucleic acid sequence of an aptamer may, under defined conditions, have a three-dimensional structure that is specific to a defined target structure.

Embodiments comprise competitive aptamers that compete for binding to a target as defined herein with aptamers as described herein. Embodiments comprise competitive aptamers that compete for binding to a target as defined herein with the aptamers set forth in any one of SEQ ID NOs: 1 to 14, 23 to 39, or 43 to 55, or with aptamers having a nucleic acid sequence having at least 85%, at least 90%, at least 95%, at least 96%, at least 97%, at least 98%, at least 99% sequence identity to the nucleotide sequence of any one of SEQ ID NOs: 1 to 14, 23 to 39, or 43 to 55. Embodiments comprise competitive one or more aptamers that compete for binding to a target as defined herein with one or more of the aptamers described above. In embodiments, competition assays may be used identify a competitive aptamer that competes for binding to a target as defined herein. In an exemplary, non-limiting, competition assay, an immobilized target as defined herein is incubated in a solution comprising a first labelled aptamer that binds to a target as defined herein and a second unlabelled aptamer that is being tested for its ability to compete with the first aptamer for binding to a target as defined herein. As a control, an immobilized target as defined herein may be incubated in a solution comprising the first labelled aptamer but not the second unlabelled aptamer. After incubation under conditions permissive for binding of the first aptamer to a target as defined herein excess unbound aptamer may be removed, and the amount of label associated with immobilized target as defined herein measured. If the amount of label associated with immobilized target as defined herein is substantially reduced in the test sample relative to the control sample, then that indicates that the second aptamer is competing with the first aptamer for binding to a target as defined herein.

Methods

Embodiments of the present disclosure relate to a method for killing or inactivating *C. difficile* spores, comprising contacting the spores with a sporicidal solution and an aptamer.

In embodiments, the method is for enhancing the sporicidal effect of the sporicidal solution and comprises contacting *C. difficile* spores with an aptamer as described herein, prior to, simultaneously with or subsequent to the sporicidal solution. Embodiments of the present disclosure relate to a method which comprises a first step of determining whether *C. difficile* is located at a location e.g. on a surface.

In the context of the present disclosure the term "killing or inactivating spores" is intended to mean that at least 85%, e.g. 86, 87, 88, 89, 90, 91, 92, 93, 94, 95, 96, 97, 98 or at least 99% of the spores are not capable of transforming (germinating) into vegetative cells.

In some embodiments, 99.9% of the spores are not capable of transforming into vegetative cells. In an embodiment, 99.99% or 99.999% of the spores are not capable of transforming into vegetative cells. In some embodiments, at least 85% of the spores are not capable of transforming into vegetative cells.

The *C. difficile* colonization may be comprised of a single strain or may be a mixture of strains. For example, the *C. difficile* may be a strain of a Clade selected from Clade 1, 2, 3, 4 and 5. In certain embodiments, the strain is selected from SH7 (Clade 1), SH8 (Clade 2), R20291 (Clade 2), SH9 (Clade 3), SH10 (Clade 4), ATCC 43598 (Clade 4) and SH11 (Clade 5). In certain embodiments, the strain is selected from R20291, ATCC 43598 and SH11.

The spores may be contacted at a temperature between 0° C. and 90° C., e.g. between 5° C. and 80° C., e.g. between 10° C. and 70° C., between 15° C. and 60° C., between 18° C. and 50° C., or between 20° C. and 40° C., e.g. 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C.

In embodiments, the method is performed at a temperature of between about 5° C. to about 90° C. e.g. 5° C., 10° C., 15° C., 20° C., 25° C., 30° C., 35° C., 40° C., 45° C., 50° C., 55° C., 60° C., 65° C., 70° C., 75° C., 80° C. or 90° C. In embodiments, the method may be performed at a temperature in the range of about 5° C. to about 90° C. In embodiments, the method may be performed at a temperature in the range of about 5° C. to 10° C., 10° C. to 15° C., 15° C. to 20° C., 20° C. to 25° C., 25° C. to 30° C., 30° C. to 35° C., 35° C. to 40° C., 40 to 45° C., 45° C. to 50° C., 50° C. to 55° C., 55° C. to 60° C., 60° C. to 65° C., 65° C. to 70° C., 70° C. to 75° C., 75° C. to 80° C., 80° C. to 85° C., 85° C. to 90° C., or any interval between any of these temperature ranges. In an embodiment, the heating temperatures are selected from 1° C. increments selected from the range of 5° C. to 90° C.

Certain embodiments of the disclosure provide methods and kits which are suitable for killing or inactivating spores in a variety of environments. Certain embodiments of the disclosure provide methods and kits which are suitable for enhancing the sporicidal effect against *C. difficile* spores of a sporicidal solution in a variety of environments. The methods and products of certain embodiments may be used in any environment to reduce spore contamination, such as the health-care industry (e.g. animal hospitals, human hospitals, animal clinics, human clinics, nursing homes, day-care facilities for children or senior citizens, etc.), the food industry (e.g. restaurants, food-processing plants, food-storage plants, grocery stores, etc.), the hospitality industry (e.g. hotels, motels, resorts, cruise ships, etc.), the education industry (e.g. schools and universities), etc.

The composition of the disclosure may desirably be used in any environment to reduce spore contamination, such as general-premise surfaces (e.g. floors, walls, ceilings, exterior of furniture, etc.), specific-equipment surfaces (e.g. hard surfaces, manufacturing equipment, processing equipment, etc.), textiles (e.g. cottons, wools, silks, synthetic fabrics such as polyesters, polyolefins, and acrylics, fiber blends such as cotton polyester, etc.), wood and cellulose-based systems (e.g. paper), soil, animal carcasses (e.g. hide, meat, hair, feathers, etc.), foodstuffs (e.g. fruits, vegetables, nuts, meats, etc.), and water.

In one embodiment, the method of the disclosure is directed to sporicidal treatment of textiles. Non-limiting examples of textiles that can be treated with the composition of the disclosure include, but are not limited to, personal items (e.g. shirts, pants, stockings, undergarments, etc.), institutional items (e.g. towels, lab coats, gowns, aprons, etc.), hospitality items (e.g. towels, napkins, tablecloths, etc.).

The surface may be an inanimate surface. The surface may be for example a surface located in a healthcare setting e.g. a hospital, a pharmacy, a doctor's surgery and/or care home facility. The aptamers may be for use in killing and/or inactivating (and optionally first detecting) *C. difficile* spores located on a surface of an object in an environment selected from the group consisting of a school, a prison, a hostel, a dormitory, a train, a bus and an airplane.

The surface may be located on an object in a location such as a hospital or other healthcare setting. For example, the object may be selected from the group consisting of an operating table, a hospital bed, a surgical instrument, a table, operating scrubs, a refuse container, eating utensils, a chair, a door handle and a doorknob. Alternatively, or in addition, the surface may be located in a location such as walls, ceilings and/or floors in e.g. hospital wards, operating theatres, care home rooms and the like.

In embodiments, the surface may be a surface of an object in a community setting for example a shop, a bar and/or a restaurant. In non-limiting examples, the surface may be located on a wall, a floor, an item of furniture, cutlery, packaging, drinking vessels and the like.

In embodiments, the surface is located in a household environment.

In embodiments, the surface is located in a food production facility.

In certain embodiments, the surface is composed of stainless steel. In certain embodiments, the surface is composed of cardboard. In an embodiment, the surface is composed of plastic.

In certain embodiments, the method comprises contacting a composition comprising an aptamer according to the present disclosure with a surface directly. That is to say, in certain embodiments, the method comprising applying a composition comprising the aptamer to the surface. In embodiments, the method comprises contacting a composition comprising an aptamer according to the present disclosure with a surface indirectly.

In embodiments in which the aptamer is contacted with the surface directly, the method may comprise providing the aptamer in a composition which is capable of being dispersed across the surface. In certain embodiments, immediate contact with the surface dispersed the composition uniformly for maximum surface area coverage and wettability facilitates the accessibility of aptamer to target molecules on the *C. difficile* spore.

Most environmental surface areas are neutral (uncharged) or have negative electrostatic energy. In certain embodiments, the aptamer is applied to a target surface area using electrostatic force of attraction. It is considered that electrostatically applied liquids have a wrapping effect, so that complex objects and areas hidden from the line of sight get coated with the liquid.

Based on Coulomb's law, an electrostatic application system applies aptamer/buffer solutions more evenly to all surfaces. Coulomb's law states that the magnitude of the electrostatic force of interaction between two-point charges is directly proportional to the scalar multiplication of the square of the distance between them. The force is along the straight line joining them. Charged spray droplets are attracted to surfaces and are considered to have an enveloping effect around the object to insure all sides are covered.

Using Coulomb's law, these systems place a positive or negative charge on the chemical solution as it leaves the spray nozzle. Because most surface areas are neutral or negative, a positively charged electrostatic spray application system optimizes adhesion and attraction. The dispersed droplets may spread out more evenly and seek out the negative (−) or neutrally charged surface. Thus in certain embodiments, the composition comprising the aptamers as described herein is more targeted and provides more consistent coverage with less waste.

In embodiments, the method comprises applying a composition comprising an aptamer to a surface by a spray gun modified with an electrode. The electrode charges liquid droplets comprising the aptamer which are then guided to the surface, which is typically oppositely charged to the aptamer.

In embodiments, the method comprises producing a composition comprising the aptamer. In embodiments, the aptamers of the presently claimed disclosure are provided in a dried form and are dissolved completely to a desired stock concentration with a buffer solution or dH2O. This may be achieved by, for example, shaking the composition for a predetermined period of time e.g. 20 minutes, 25 minutes, 30 minutes or more e.g. 35 minutes, 40 minutes, 45 minutes or greater. The composition may comprise an organic solvent e.g. DMSO, ethanol and/or methanol. Additionally, the composition may comprise a salt such as for example a sodium ion.

In embodiments, the method comprises dissolving the aptamer in a buffer solution. The buffer solution may be selected from, for example PBS, HEPES, Tris etc. Typically, aptamers are stable at neutral pH range (7.0-8.0). A heating and a cooling step may be performed for the proper folding of aptamer structure in a buffer solution (for example heating at 95° C. for 5 min followed by slow cooling to room temperature). In certain embodiments, the method comprises providing a 2+ ion such as magnesium in the buffer solution. Divalent ions such as magnesium may be advantageous in certain embodiments to maintain a proper structure of the aptamer.

Nucleic acid aptamer in the binding buffer condition (pH 7.4) is negatively charged and through electrostatic interactions the aptamer could favor binding to positively charged areas. To avoid this interaction with aptamer/buffer and container the use of anti-static treated materials (e.g., plastic and glass vessels) are important. Typically, the sprayer will be made of plastics.

In embodiments, the method comprises applying a composition comprising the aptamer to the surface by spraying the surface.

In embodiments, the aptamers may be freeze-dried prior to being sprayed onto the surface. Thus, in certain embodiments the method comprises a step of contacting the surface with a freeze-dried composition comprising the aptamer as described herein.

During the spray freezing step, the aptamer dissolved or suspended in liquid is atomized into fine droplets which are frozen instantaneously by a cryogenic fluid, usually liquid nitrogen. Subsequently, the frozen particles are subjected to freeze drying, in which the solvents are sublimed at low temperature and pressure, leading to the formation of dried porous particles. Porous particles with large physical size and low density exhibit small aerodynamic size, which can promote high flowability. The small contact surface area to volume ratio leads to low cohesion force between particles, thereby facilitates dispersibility in air. In addition, porous particles have high specific surface area, thereby enhancing dissolution rate.

In embodiments, the method comprises dissolving freeze-dried aptamers in a solution prior to contacting the surface with a liquid solution.

In embodiments, the method of killing and/or inactivating *C. difficile* at a location, e.g. a surface, may comprise applying one or more of the aptamers of the disclosure to a location suspected of comprising *C. difficile* spores. Following a predetermined period of time sufficient to permit the aptamer binding to *C. difficile* spores, the surface may be washed one or more times to remove any unbound aptamer. In embodiments, e.g. when a FRET pair is used or beacon as described herein, the washing step is not required.

In certain embodiments, for use on environmental surfaces such as stainless steel, polystyrene and other surfaces the aptamers are designed to attach to the target, i.e. a *C. difficile* spores, and fluoresce. The aptamers will not fluoresce by attaching to the inorganic surface alone.

Sporicidal Agent

Embodiments of the disclosure comprise the use of sporicidal agents e.g. sporicidal solutions. Bacterial spores are considered to be highly resistant to chemical and physical agents. Embodiments of the present disclosure aim to increase the sensitivity of the spore to sporicidal agents.

As used herein, the term "sporicidal agent" refers to an agent which is capable of killing *C. difficile* spores. In certain embodiments, the methods described herein may replace a sporicidal agent with a sporostatic agent, i.e. an agent which is inhibitory to spore germination or outgrowth or both. Certain agents may be sporostatic at certain concentrations and/or temperatures and sporicidal at higher concentrations and/or temperatures.

Exemplary sporicidal agents include but are not limited to glutaraldehyde, sodium hypochlorite, iodine, iodophors, hydrogen peroxide and peracetic acid.

The sporicidal solution for use in embodiments of the present disclosure may be an alkylating agent, and oxidizing agent and/or a chlorine-releasing agent.

In embodiments, the sporicidal agent is a solution. In embodiments, the sporicidal agent comprises an agent which, on addition of water, generates peracetic acid. In embodiments, the sporicidal agent is a solution comprising peracetic acid. The solution may be formed by wetting dry wipes (such as wipes marketed under the Clinell trade name) and squeezing solution from the wetted wipe.

In certain embodiments, the sporicidal agent is formed from a wipe comprising Sodium Percarbonate at a concentration of ≤50 (% wt) (Cas No. 239-707-6 15630-89-4) and Citric Acid (concentration≤20 (% wt) (Cas No. 77-92-9 201-069-1). The wipe may also comprise tetra acetyl ethylene diamine (concentration≤25% wt.)

In embodiments, the sporicidal agent is a solution comprising peracetic acid. In embodiments, the sporicidal agent comprises an agent which is capable of generating peracetic acid. In embodiments, the sporicidal agent comprises sodium percarbonate.

In embodiments, the sporicidal agent may be a wipe sold under Mikrozid® brand name.

In embodiments, the sporicidal agent comprises peracetic acid (e.g. at a concentration of about 0.05-0.10% in a 100 g agent solution) and hydrogen peroxide. The sporicidal agent may further comprise acetic acid. In certain embodiments, the agent comprises around 0.06% peracetic acid.

In embodiments, the sporicidal solution comprises sodium hypochlorite. The solution may comprise sodium hypochlorite in a concentration of between about 0.3 to about 0.7% v.v. The solution may be pre-diluted to form the sporicidal solution for use in the methods of embodiments of the disclosure.

In embodiments, the sporicidal solution may comprise hydrogen peroxide e.g. about 1.5% (Aseptix Sterimax Sporicide wipes). In embodiments, the solution comprises a silver-stabilised hydrogen peroxide e.g. a solution sold under the trademark EndoSan®.

In embodiments, the sporicidal solution comprises chlorhexidine digluconate. Aptly, the sporicidal solution is a solution available under the brand name Chemgene™.

In embodiments, the sporicidal solution comprises glucoprotamin 1.5% (Incidin plus wipes); a mixture of ethanol, propane and N-alkyl amino propyl glycine (Bacillol 30 tissues); and finally, a mixture of didecyldimonium chloride, benzalkonium chloride, polyaminopropyl, biguanide and dimenthicone as active ingredients (Formula 429 spray).

Detectable Labels

In embodiments, the aptamers of the disclosure are used to detect and/or quantify the amount of *C. difficile* at a location. In embodiments, the methods comprise a step of determining the presence, absence and/or concentration of *C. difficile* at a surface prior to contacting the location with a sporicidal agent (i.e. kill the spore) and/or sporistatic agent (e.g. agent that inhibits spore germination or outgrowth). The step of determining the presence, absence and/or concentration comprises contacting the location with one or more aptamers as defined herein for a period of time to enable an aptamer-spore complex to form.

In embodiments, the aptamer comprises a detection molecule. Any label capable of facilitating detection and/or quantification of the aptamers may be used herein.

In embodiments, the detectable label is a fluorescent moiety, e.g. a fluorescent/quencher compound. Fluorescent/quencher compounds are known in the art. See, for example, Mary Katherine Johansson, Methods in Molecular Biol. 335: Fluorescent Energy Transfer Nucleic Acid Probes: Designs and Protocols, 2006, Didenko, ed., Humana Press, Totowa, NJ, and Marras et al., 2002, Nucl. Acids Res. 30, el22 (incorporated by reference herein).

In embodiments, the detectable label is FAM. In certain embodiments, the FAM-label is situated at the first and/or second primer region of the aptamer. The person skilled in the art would understand that the label could be located at any suitable position within the aptamer.

Moieties that result in an increase in detectable signal when in proximity of each other may also be used herein, for example, as a result of fluorescence resonance energy transfer ("FRET"); suitable pairs include but are not limited to fluoroscein and tetramethylrhodamine; rhodamine 6G and malachite green, and FITC and thiosemicarbazole, to name a few.

In embodiments, the detectable label is selected from at least one of the following non-limiting examples: a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, and a liposome.

In embodiments, the detectable label is a fluorescent protein such as Green Fluorescent Protein (GFP) or any other fluorescent protein known to those skilled in the art.

In embodiments, the nature of the detection will be dependent on the detectable label used. For example, the label may be detectable by virtue of its color, e.g. gold nanoparticles. A color can be detected quantitatively by an optical reader or camera e.g. a camera with imaging software.

In embodiments, the detectable label is a fluorescent label, e.g. a quantum dot. In such embodiments, the detection means may comprise a fluorescent plate reader, strip reader or similar, which is configured to record fluorescence intensity.

In embodiments in which the detectable label is an enzyme label, the detection means may, for example, be colorimetric, chemiluminescence and/or electrochemical (for example, using an electrochemical detector). Electrochemical sensing is through conjugation of a redox reporter (including but not limited to methylene blue or ferrocene) to one end of the aptamer and a sensor surface to the other end. Typically, a change in aptamer conformation upon target binding changes the distance between the reporter and sensor to provide a readout.

In embodiments, the detectable label may further comprise enzymes such as horseradish peroxidase (HRP), Alkaline phosphatase (APP) or similar, to catalytically turnover a substrate to give an amplified signal.

In embodiments, the disclosure provides a complex (e.g. conjugate) comprising aptamers of the disclosure and a detectable molecule. Typically, the aptamers of the disclosure are covalently or physically conjugated to a detectable molecule.

In embodiments, the detectable molecule is a visual, optical, photonic, electronic, acoustic, opto-acoustic, mass, electrochemical, electro-optical, spectrometric, enzymatic, or otherwise physically, chemically or biochemically detectable label.

In embodiments, the detectable molecule is detected by luminescence, UV/VIS spectroscopy, enzymatically, electrochemically or radioactively. Luminescence refers to the emission of light. For example, photoluminescence, chemiluminescence and bioluminescence are used for detection of the label. In photoluminescence or fluorescence, excitation occurs by absorption of photons. Exemplary fluorophores include, without limitation, bisbenzimidazole, fluorescein, acridine orange, Cy5, Cy3 or propidium iodide, which can be covalently coupled to aptamers, tetramethyl-6-carboxyhodamine (TAMRA), Texas Red (TR), rhodamine, Alexa Fluor dyes (et al. Fluorescent dyes of different wavelengths from different companies).

In certain embodiments, the detectable molecule is one of a FRET pair. In certain embodiments, the aptamer may comprise a FRET pair as detectable molecules. Binding of the aptamer to the *C. difficile* spore may result in a loss of quenching which is detectable.

In embodiments, the detectable molecule is a colloidal metallic particle, e.g. gold nanoparticle, colloidal non-metallic particle, quantum dot, organic polymer, latex particle, nanofiber (e.g. carbon nanofiber), nanotube (e.g. carbon nanotube), dendrimer, protein or liposome with signal-generating substances. Colloidal particles can be detected colorimetrically.

In embodiments, the detectable molecule is an enzyme. In certain embodiments, the enzyme may convert substrates to coloured products, e.g. peroxidase, luciferase, β-galactosidase or alkaline phosphatase. For example, the colorless substrate X-gal is converted by the activity of β-galactosidase to a blue product whose color is visually detected.

In embodiments, the detection molecule is a radioactive isotope. The detection can also be carried out by means of radioactive isotopes with which the aptamer is labelled, including but not limited to 3H, 14C, 32P, 33P, 35S or 125I, more preferably 32P, 33P or 125I. In the scintillation counting, the radioactive radiation emitted by the radioactively labelled aptamer target complex is measured indirectly. A scintillator substance is excited by the isotope's radioactive emissions. During the transition of the scintillation material, back to the ground state, the excitation energy is released again as flashes of light, which are amplified and counted by a photomultiplier.

In embodiments, the detectable molecule is selected from digoxigenin and biotin. Thus, the aptamers may also be labelled with digoxigenin or biotin, which are bound for example by antibodies or streptavidin, which may in turn carry a label, such as an enzyme conjugate. The prior covalent linkage (conjugation) of an aptamer with an enzyme can be accomplished in several known ways. Detection of aptamer binding may also be achieved through labelling of the aptamer with a radioisotope in an RIA (radioactive immunoassay). In an embodiment, the radioisotope is 125I. Detection of aptamer binding may also be achieved through labelling of the aptamer by fluorescence in a FIA (fluoroimmunoassay) with fluorophores. In an embodiment, the fluorophore is fluorescein or FITC.

In some embodiments, antisense oligonucleotides can be designed to hybridize that are complementary to the 5' end, the 3' end, the 5' end and the 3' end of or any relevant sequence of the aptamer (e.g. H2.1.2-as SEQ ID NOs: 40-41) In some embodiments, the antisense oligonucleotides comprises a fluorophore.

Embodiments comprise methods for detecting the presence, absence or amount of a target as defined herein at a location e.g. a surface. In the methods, the surface may be interacted (i.e. contacted) with an aptamer as described herein. For example, the surface and aptamers as described herein may be incubated under conditions sufficient for at least a portion of the aptamer to bind to a target as defined herein in the sample.

A person skilled in the art will understand that the conditions required for binding to occur between the aptamers described herein and a target as defined herein. In embodiments the sample e.g. a target surface at a location suspected of including *C. difficile* spores, and aptamer may be incubated at temperatures between about 4° C. and about 40° C. In embodiments the sample and aptamer may be incubated at temperatures between about 20° C. and about 37° C. In embodiments the sample and aptamer may be incubated at 22° C. The incubation temperature may be selected from the range of 4° C. to less than 20° C., 20° C. to less than 22° C., 22° C. to less than 24° C., 24° C. to less than 26° C., 26° C. to less than 28° C., 28° C. to less than 30° C., 30° C. to less than 32° C., 32° C. to less than 34° C., 34° C. to less than 36° C., 36° C. to less than 37° C. and 37° C. to less than 40° C. In embodiments, the sample and aptamer may be diluted to different concentrations (e.g. at least about 1%, 5%, 10%, 20%, 25%, 30%, 40%, 50%, 60%, 70% 80% v/v or more) with a buffer (exemplary buffers include but are not limited to PBS). The diluted concentrations may be selected from the range of 1% to less than 5%, 5% to less than 10%, 10% to less than 20%, 20% to less than 30%, 30% to less than 40%, 40% to less than 50%, 50% to less than 60%, 60% to less than 70%, 70% to less than 80%, or 80% to less than 90% v/v. In embodiments, the aptamer concentration before dilution may be from 100 nM to 50 μM. In embodiments, the aptamer concentration before dilution may be selected from the range of 100 nM to 500 nM, 500 nM to 1 μM, 1 μM to 2 μM, 2 μM to 5 μM, 5 μM to 10 μM, 10 μM to 15 μM, 15 μM to 20 μM, 20 μM to 30 μM, 30 μM to 40 μM, 40 μM to 50 μM, 50 μM to 60 μM, 60 μM to 70 μM, 70 μM to 80 μM, 80 μM to 90 μM, 90 μM to 100 μM. In embodiments, the aptamer concentration before dilution may be a concentration selected from the ranges described herein. The selected value may be selected from 0.1 μM increment concentrations in a range herein. In embodiments, the aptamer concentration before dilution may be 2 μM. In embodiments, the aptamer concentration used for binding may be selected from the range of 10 μM to 40 μM, In embodiments, the aptamer concentration used for binding may be selected from the range of 10 μM to 15 μM, 15 μM to 20 μM, 20 μM to 25 μM, 25 μM to 30 μM, 30 μM to 35 μM, 35 μM to 40 μM, or any concentration between any of these concentration ranges selected from 1 μM increments selected from the range of 10 μM to 40 μM. In an embodiment, the aptamer concentration used for binding may be 20 μM. In an embodiment, the aptamer concentration used for binding may be 25 μM. In an embodiment, the aptamer concentration used for binding may be 30 μM. In embodiments, the sample and aptamer may be incubated whilst shaking and/or mixing. In certain embodiments, the sample and aptamer are incubated for at least 1 minute, at least 5 minutes, at least 15 minutes, at least 1 hour or more. The sample and aptamer may be incubated for 1 minute to less than 5 minutes, 5 minutes to less than 15 minutes, 15 minutes to less than one hour, one hour to less than 24 hours, 24 hours to less than 48 hours.

In embodiments, binding of the aptamer and a target as defined leads to formation of an aptamer-target complex. The binding or binding event may be detected, for example, visually, optically, photonically, electronically, acoustically, opto-acoustically, by mass, electrochemically, electro-optically, spectrometrically, enzymatically or otherwise chemically, biochemically or physically as described herein.

The binding of aptamer and the target may be detected using any suitable technique. As discussed above, for example, binding of the aptamer and the target may be detected using a biosensor. In embodiments, binding of the aptamer and the target is detected using SPR, RIfS, BLI, LFD or ELONA as described herein.

In embodiments, the method comprises a step of determining the binding of the aptamer to a *C. difficile* spore and subsequently a step of determining killing and/or inactivation of *C. difficile* spores. In embodiments, the method comprises visualising the killing and/or inactivation of *C. difficile* spores. Such visualization may be in the form of a loss of a detectable signal, e.g. the reduction or loss of a visual, optical, photonic, electronic, acoustic, opto-acoustic, mass, electrochemical, electro-optical, spectrometric or enzymatic signal.

In embodiments, the method comprises the use of a light source, such as a laser; focusable optics, such as a lens; filters or monochromators to effect changes in the spectrum of excitation or fluorescence emission; and a CCD camera or a single photon count detector to measure fluorescence to visualise the binding of aptamer to *C. difficile* spores and/or the killing and/or inactivation of *C. difficile* spores.

The method may comprise a set of conditions for illuminating the location using a light source. In an embodiment, the light source may be in the form of a forensic light source. In an embodiment, the light source may be in the form of a Polilight® Flare.

In embodiments, the light source may be capable of switching between different wavelengths, each wavelength being suited to a specific interchangeable filter. The forensic light source may be in the form of a LED, laser, Polilight® or the like. In embodiments, the light source is a handheld light source. In an embodiment, the handheld light source may be a Polilight Flare+2, which is a battery operated, handheld LED light source, available from e.g. Rofin Forensic.

In embodiments, each Polilight Flare "torch" may produce light within a specified wavelength range. For example, in embodiments, the light source may produce light at a wavelength of between about 360 nm-385 nm (UV light). In embodiments, the light source may produce light at a wavelength of between about 405 nm-420 nm. In embodiments, the light source may produce light at a wavelength of between about 435 nm-465 nm. In embodiments, the light source may produce light at a wavelength of between about 485 nm-515 nm. In embodiments, the light source may produce light at a wavelength of between about 510 nm-545 nm. In embodiments, the light source may produce light at a wavelength of between about 530 nm-560 nm. In embodiments, the light source may produce light at a wavelength of between about 585 nm-605 nm. In embodiments, the light source may produce light at a wavelength of between about 615 nm-635 nm. In embodiments, the light source may produce light at a wavelength of between about 400 nm-700 nm. In embodiments, the light source may produce light at a wavelength of between about 835 nm-865 nm. In embodiments, the light source may produce light at a wavelength of between about 935 nm-965 nm.

In embodiments, the light source used may be compatible with a detectable molecule conjugated to the aptamer. In embodiments, the aptamer will be conjugated to a detection molecule. In embodiments, the detection molecule may be a fluorophore which emits in a spectral range which corresponds to the output of the light source. In embodiments, the aptamer may be conjugated to a fluorophore which emits at a wavelength of about 505 nm. In embodiments, the light source produces light having a wavelength of about 505 nm.

In embodiments, the method may comprise the use of a bandpass filter in combination with the light source. The bandpass filter may be configured to transmit light of a certain wavelength band and reject stray light outside the predetermined wavelength band. In embodiments, the light source is configured to produce narrow bands of light having centre wavelengths of 365 nm, 415 nm, 450 nm, 505 nm, 530 nm, 545 nm, 620 nm, and 850 nm. In embodiments, the light source is configured to produce narrow bands of light having a center wavelength of 505 nm, in addition to white light wavelengths. In embodiments, the bandpass filter is a 590 nm bandpass filter.

In embodiments, the method may further comprise visualising the location of the surface with viewing goggles, glasses, or the like. In embodiments, the viewing goggles are of a colour which corresponds to the colour of light produced by the light source and emitted by the detection molecule conjugated to the aptamer. In embodiments, the goggles are orange and thus are suitable for use in combination with a light source which produces light having a wavelength of between about 485 nm-515 nm, e.g. 505 nm, and an aptamer which comprises a detection molecule that emits at a wavelength of approximately 505 nm.

Compositions

In certain aspects of the disclosure, there is provided a combination of one or more aptamers as described herein and a sporicidal and/or sporistatic agent as defined herein. The combination may be for use in methods of killing and/or inactivating *C. difficile* e.g. *C. difficile* spores at a location such as a surface. The combination may also be for use in the enhancement of sporicidal activity of the sporicidal agent. The combination may also be for use in the detection of *C. difficile* spores prior to killing or inactivation.

The aptamers as defined herein and the sporicidal agent may be provided in a single composition. The composition may further comprise other components such as but not limited to a buffer solution, stabilizing agents, colourants and the like.

Alternatively, the aptamer and the sporicidal agent may be provided in separate compositions. In embodiments, the aptamer and the sporicidal agent may be for sequential application to the location.

The disclosure also provides a kit for killing and/or inactivation of *C. difficile*, wherein the kit comprises one or more aptamers as described herein. In embodiments, the kit also comprises a sporicidal agent. In embodiments, the sporicidal agent is a solution as described herein. In embodiments, the kit also comprises a detectable molecule as described herein.

In some embodiments, the kit further comprises instructions for use in accordance with any of the methods described herein.

Typically, the kit comprises further components for the reaction intended by the kit or the method to be carried out, for example components for an intended detection of enrichment, separation and/or isolation procedures. Examples are buffer solutions, substrates for a color reaction, dyes or enzymatic substrates. In the kit, the aptamer may be provided in a variety of forms, for example pre-immobilised onto a support (e.g. solid support), freeze-dried or in a liquid medium.

The kit of the disclosure may be used for carrying out any method described herein. It will be appreciated that the parts of the kit may be packaged individually in vials or in combination in containers or multi-container units. Typically, manufacture of the kit follows standard procedures which are known to the person skilled in the art.

EXAMPLES

In the following, the disclosure will be explained in more detail by means of non-limiting examples of specific embodiments. In the example experiments, standard reagents and buffers free from contamination are used.

Example 1

Demonstration of sporicidal activity of three sporicidal products at five concentrations in the presence and absence of the CotE_H2 aptamer using *Clostridioides difficile* (previously *Clostridium difficile*) SH11 spores.

Demonstration of sporicidal activity of three sporicidal products at five concentrations in the presence and absence of three aptamers using two strains of *C. difficile* spores.

Materials and Methods

Test Microorganisms

The *Clostridium difficile* spore suspensions used in this study are listed in Table 5.

*C. difficile* SH11 suspensions were provided by Spore-Gen® and stored at 4° C. upon arrival. *Clostridioides difficile* R20291 suspension was provided by Sporegen® and stored at 4° C. upon arrival.

TABLE 5

Details of *Clostridium difficile* spore suspensions used in this study.

| Ribotype | Description | In-test Concentration |
|---|---|---|
| RT027 (R20291) | Purified spore suspension | $1 \times 10^8 \pm 5 \times 10^7$ |
| RT078 (SH11) | Purified spore suspension | $1 \times 10^8 \pm 5 \times 10^7$ |
| ATCC ® 43598 ™ | Internal strain spore suspension | $1 \times 10^8 \pm 5 \times 10^7$ |

Test Agents

Test agents used are listed in Table 6 and 7. Aptamers and buffers were provided by Aptamer Group Limited.

The sporicidal agents can be obtained as follows: Chemgene™ (a high level laboratory surface disinfectant that combines active ingredient molecules with micelle cleaning technology, biodegradable, non-corrosive-see www.starlabgroup.com/GB-en/gloves-safety/laboratory-disinfectant_WebPSub-159946/chemgene-hld4h-rtu-spray-blue-*eucalyptus*-1:20-750ml_SLXTM302-C) Endosan® (hard surface silver stabilised hydrogen peroxide see www.clinipathequipment.com/product/endosan-3-trigger-spray Clinell® (Peracetic acid generating wipes comprising sodium percabonate (≤50% wt, citric acid≤20 wt % and tetra acetyl ethylene diamine≤25 wt %-see gamahealthcare.com/products/sporicidal-wipes)

TABLE 6

| Test Agent | Buffer | Concentration provided (μM) | In-test concentration (μM) |
|---|---|---|---|
| CotE_H2 aptamer | TbKst | 100 | 20 |
| CDec_D1 aptamer | TbKat | 100 | 20 |
| CDem_D2 aptamer | TbKat | 100 | 20 |

TABLE 7

Liquid sporicidal test agents and control solutions used throughout the study. PBS = phosphate buffered saline, RCM = reinforced clostridial medium.

| Test Agent | Product Type | Lot Number | In-test concentrations (%) |
|---|---|---|---|
| Clinell ® sporicidal solution | Liquid sporicidal | SA613818 | 50, 25, 12.5, 6.25, 3.125, 1.5625 |
| EndoSan ® | Liquid sporicidal | 170117HS0300 | 50, 25, 12.5, 6.25, 3.125, 1.5625 |
| Chemgene ™ | Liquid sporicidal | 190592 | 50, 25, 12.5, 6.25, 3.125, 1.5625 |
| Negative control | PBS + 1% RCM | PBS191018/ RCM191018 | N/A |
| Positive control | Bleach-based solution | 9 161 2696 | N/A |

Equipment and Media

- UKAS calibrated pipettes (0.5-1000 μL range), Proline® Plus—Sartorius UK
- UKAS calibrated multichannel pipettes (P300-P20)—Gilson UK
- Eppendorf 5452 minispin centrifuge—Eppendorf, DE
- Calibrated balance, Ohaus NV212—Scientific Laboratories Supplies (SLS) UK
- Anaerobic cabinet, Whitley MG500-Don Whitley Scientific Limited, UK
- Digital dry bath—SLS, UK
- Sterile universal tubes—SLS, UK
- 96-well plates, SLS, UK Media

- Nuclease free water—Aptamer Group
- TbKat buffer—Aptamer Group
- TbKst buffer—Aptamer Group
- Brain heart infusion agar supplemented with horse blood and yeast (BHI-YHT).
- For components see Table 8
- Reinforced clostridial medium (RCM) Acumedia®—SLS, UK
- Phosphate buffered saline (PBS)—SLS, UK
- GH neutraliser (for components see Table 9)

TABLE 8

| Preparation of BHIY-HT | |
|---|---|
| Chemical Name | Quantity |
| BHIA | 26 g |
| Yeast Extract | 2.5 g |
| Sodium Taurocholate Hydrate | 0.5 g |
| Horse Blood | 35 mL |
| Distilled Water | 500 mL |

TABLE 9

| Preparation of GH neutraliser | |
|---|---|
| Compound | Quantity |
| Saponin | 20 g |
| Sodium thiosulphate | 10 g |
| Sodium dodecyl sulfate | 5 g |
| Lecithin | 1 g |
| L-histidine | 1 g |
| Tween 80 | 20 g |
| Distilled water | 1 L |

Method

Prior to testing, the CotE_H2 aptamer was diluted in nuclease free water to a 4× stock concentration of 80 μM. The aptamers were folded by heating to 95° C. in a digital dry bath for 5 minutes and then immediately placed in ice and cooled to 2° C. The CotE_H2 was stored at 2-4° C. while in use. A *Clostridium difficile* SH11 bacterial spore inoculum was prepared to $1\times10^8\pm5\times10^7$ $CFUmL^{-1}$ according to internal procedures. The inoculum was confirmed by serial dilution and plating out the resultant suspensions onto brain heart infusion agar supplemented with horse blood and yeast (BHI-YHT). Each 4× stock concentration of CotE-H2 (80 μM) was diluted in TbKst buffer to obtain a 2× in-test concentration (40 μM). Ten microlitres of *C. difficile* spores were added to 10 μL of 2× in-test concentration of CotE-H2. The spore suspension was pipette mixed and incubated with CotE-H2 at room temperature for one hour. The spores were then washed three times by centrifuging at 13,400 RPM for 10 minutes. In each wash the supernatant was removed, and the pellet was resuspended in 100 μL of "TbKst" buffer. Following the third wash, the spores were resuspended in 100 μL of "TbKst" buffer and vortexed to obtain a homogenous solution.

A total of five 2× in-test concentrations (1:2 dilutions) of each sporicidal test agent were prepared from the stock (100%, 50%, 25%, 12.5%, 6.25%, 3.125%). The Clinell solutions were prepared by adding 100 mL water to the wipes and then squeezing the solution out of them.

Negative and positive control solutions were also prepared. Twenty-five microliter aliquots of each sporicidal test agent concentration or control solution were added to the wells of a 96-well plate. A 25 μL aliquot of the aptamer-spore suspension was added to each test agent or control solution and pipette mixed. The final in-test concentrations of each sporicidal test agent were 50%, 25%, 12.5%, 6.25%, 3.125%, 1.5625%. The plates were then incubated for 15 minutes at 37° C.±2° C. in an anaerobic environment. Following incubation, 50 μL of GH neutraliser was added to each well and pipette mixed. A 10 μL aliquot of neutralised suspension was taken from each well and transferred to an agar plate and incubated for 48 hours at 37° C.±2° C. in an anaerobic environment. Growth was recorded as "+" and no growth as "–". The minimum sporicidal concentration (MSC) for each concentration was identified as the lowest concentration with no growth for all replicates. If no growth was observed at the lowest concentration it was displayed as "<". If growth was observed at the highest concentration it was displayed as ">". The test was then repeated without the aptamers being present. Testing was performed in triplicate.

Example 2

The Assessment of the Minimum Sporicidal Concentration of Three Sporicidal Products at Five Concentrations in the Presence and Absence of Three Aptamers Using Two Strains of *Clostridium difficile* Spores.

The methodology outlined in Example 1 was repeated with CDec_D1 and CDem_D2 aptamers for *C. difficile* SH11 spores and with CotE_H2, CDec_D1 and CDem_D2 aptamers for *C. difficile* ATCC® 43598™ spores.

Results

The assessment of the minimum sporicidal concentration of three sporicidal products at five concentrations in the presence and absence of the CotE_H2 aptamer using *Clostridium difficile* SH11 spores.

When the test agents were assessed against *C. difficile* SH11 spores without the presence of the CotE_H2 aptamer, the lowest MSC (25%) was reported for Clinell® sporicidal solution (Table 10 and Table 11). A greater than 50% concentration was reported for the MSC of EndoSan® and Chemgene™. When *C. difficile* SH11 spores were tested in the presence of the CotE_H2 aptamer, a greater than two-fold increase in the MSC was reported for Clinell® sporicidal solution. The other two test products remained unchanged. Particularly, the results indicate that the MSC of the EndoSan® and Chemgene™ products had not been identified. As such, the results indicate that it was not possible to determine whether the presence of aptamers had an effect on the *C. difficile* spores.

Sporicidal Concentrations of Sporicidal Solutions in the Presence and Absence of Three Aptamers Using *Clostridium difficile*.

TABLE 10

Growth observed after recovering viable *Clostridium difficile* SH11 spores following treatment for 15 minutes with neat and diluted sporicidal solutions in the absence of CotE_H2 aptamers. "+" = growth present, "–" = no growth (n = 3).

| In-test concentration (%) | Aptamers absent | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | – | – | – | – | – | – | + | + | + | + | + | + | + | + | + | + | + | + |
| 25 | – | – | – | – | – | – | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

Sporicidal Concentrations of Sporicidal Solutions in the Presence and Absence of Three Aptamers Using *Clostridium difficile* ATCCR 43598™ Spores.

TABLE 11

Growth observed after recovering viable *Clostridium difficile* ATCC ® 43598 ™ spores following treatment for 15 minutes with neat and diluted sporicidal solutions in the absence of aptamers. "+" = growth present, "−" = no growth (n = 3).

| In-test concentration (%) | Aptamers absent | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | + | + | − | + | + | + | + | + | + | + | + | + | + | + | + | + | + | + |
| 25 | + | + | + | + | + | + | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

TABLE 12

Growth observed after recovering viable *Clostridium difficile* ATCC ® 43598 ™ spores following treatment for 15 minutes with neat and diluted sporicidal solutions in the presence of CotE_H2 aptamers. "+" = growth present, "−" = no growth (n = 3).

| In-test concentration (%) | CotE_H2 present | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | − | − | − | − | − | − | + | + | + | + | + | + | + | + | + | + | + | + |
| 25 | + | + | + | + | + | + | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

TABLE 13

Growth observed after recovering viable *Clostridium difficile* ATCC ® 43598 ™ spores following treatment for 15 minutes with neat and diluted sporicidal solutions in the presence of CDec_D1 aptamers. "+" = growth present, "−" = no growth (n = 3).

| In-test concentration (%) | CDec_D1 present | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | − | − | − | − | − | − | + | + | + | + | + | + | + | + | + | + | + | + |
| 25 | + | + | − | − | + | − | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

TABLE 14

Growth observed after recovering viable *Clostridium difficile* ATCC ® 43598 ™ spores following treatment for 15 minutes with neat and diluted sporicidal solutions in the presence of CDem_D2 aptamers. "+" = growth present, "−" = no growth (n = 3).

| In-test concen-tration (%) | CDem_D2 present | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | − | − | − | − | − | − | + | + | + | + | + | + | + | + | + | + | + | + |
| 25 | − | − | − | − | − | − | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

Sporicidal Concentrations of Sporicidal Solutions in the Presence of Two Aptamers Using *Clostridium difficile* SH11 Spores.

TABLE 15

Growth observed after recovering viable *Clostridium difficile* SH11 spores following treatment for 15 minutes with neat and diluted sporicidal solutions in the presence of CDec_D1 aptamers. "+" = growth present, "−" = no growth (N = 3).

| In-test concen-tration (%) | CDec_D1 present | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | − | − | − | − | − | − | − | + | + | + | + | + | + | + | + | + | + | + |
| 25 | − | − | − | − | − | − | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

TABLE 16

Growth observed after recovering viable *Clostridium difficile* SH11 spores following treatment for 15 minutes with neat and diluted sporicidal solutions in the presence of CDem_D2 aptamers. "+" = growth present, "−" = no growth (N = 3).

| In-test concen-tration (%) | CDem_D2 present | | | | | | | | | | | | | | | | | |
|---|---|---|---|---|---|---|---|---|---|---|---|---|---|---|---|---|---|---|
| | Clinell ® sporicidal solution | | | | | | EndoSan ® | | | | | | Chemgene ™ | | | | | |
| | N = 1 | | N = 2 | | N = 3 | | N = 1 | | N = 2 | | N = 3 | | N = 1 | | N = 2 | | N = 3 | |
| | 1.1 | 1.2 | 2.1 | 2.2 | 3.1 | 3.2 | 1.1 | 1.2 | 2.1 | 2.2 | 3.1 | 3.2 | 1.1 | 1.2 | 2.1 | 2.2 | 3.1 | 3.2 |
| 50 | + | + | + | + | + | + | + | + | + | + | + | + | + | + | + | + | + | + |
| 25 | + | + | + | + | + | + | + | + | + | + | + | + | + | + | + | + | + | + |
| 12.5 | + | + | + | + | + | + | + | + | + | + | + | + | + | + | + | + | + | + |
| 6.25 | + | + | + | + | + | + | + | + | + | + | + | + | + | + | + | + | + | + |
| 3.125 | + | + | + | + | + | + | + | + | + | + | + | + | + | + | + | + | + | + |
| 1.5625 | + | + | + | + | + | + | + | + | + | + | + | + | + | + | + | + | + | + |

TABLE 17 minimal sporicidal concentration (MSC) of Clinell ® sporicidal solution, EndoSan ® and Chemgene ™ against *Clostridium difficile* SH11 spores, in the presence and absence of CotE_H2 aptamer.

| Test Details | Clinell ® sporicidal solution | MSC (%) EndoSan ® | Chemgene ™ |
|---|---|---|---|
| CotE_H2 absent | 25 | >50 | >50 |
| CotE-H2 present | >50 | >50 | >50 |

TABLE 18

Minimal sporicidal concentration (MSC) of Clinell ® sporicidal solution, EndoSan ® and Chemgene ™ against *Clostridium difficile* ATCC ® 43598 ™ spores, in the presence and absence of CotE_H2, CDec_D1 and CDem_D2 aptamers. * = no recovery on some replicates.

| Test Details | Clinell ® sporicidal solution | MSC % EndoSan ® | Chemgene ™ |
|---|---|---|---|
| Aptamers absent | >50* | >50 | >50 |
| CotE_H2 present | 50 | >50 | >50 |
| CDec_D1 present | 50 | >50 | >50 |
| CDem_D2 present | 25 | >50 | >50 |

Discussion

When the test agents were assessed against *C. difficile* ATCC® 43598™ spores without the presence of the aptamers, a greater than 50% concentration was reported for all the test items. When *C. difficile* ATCCR 43598™ spores were tested in the presence of the Cote_H2 and CDec_D1 aptamers, the MSC for Clinell® sporicidal solution decreased. When *C. difficile* ATCCR 43598™ spores were tested in the presence of the CDem_D2 aptamer, a greater than two-fold decrease in the MSC was observed for Clinell® sporicidal solution. No change in the MSC was observed for EndoSan® and Chemgene™ in the presence of any aptamers.

When the test agents were assessed against *C. difficile* SH11 spores without the presence of aptamers, the lowest MSC (25%) was observed for Clinell® sporicidal solution. A greater than 50% concentration was observed for the MSC of EndoSan® and Chemgene™. When *C. difficile* SH11 spores were tested in the presence of the CDec_D1 aptamer, no change in the MSC was observed for any of the test items. When *C. difficile* SH11 spores were tested in the presence of the CDem_D2 aptamer, a greater than two-fold increase in the MSC was reported for Clinell® sporicidal solution (Table 19). No change in the MSC was observed for EndoSan® and Chemgene™.

TABLE 19

Minimal sporicidal concentration (MSC) of Clinell ® sporicidal solution, EndoSan ® and Chemgene ™ against *Clostridium difficile* SH11 spores, in the presence and absence of CotE_H2, CDec_D1 and Cdem_D2 aptamers.

| Test Details | Clinell ® sporicidal solution | MSC (%) EndoSan ® | Chemgene ™ |
|---|---|---|---|
| Aptamers absent | 25 | >50 | >50 |
| CDec_D1 present | 25 | >50 | >50 |
| CDem_D2 present | >50 | >50 | >50 |

Discussion

*Clostridium difficile* is a spore-forming, Gram-positive obligative anaerobic bacterium. *C. difficile* infections are considered a leading cause of infections world-wide with increased rates of associated mortality and morbidity. The spores formed by *C. difficile* on surfaces continue to be viable for several weeks, facilitating the spread and occurrence of *C. difficile* infections. Sporicidal solutions have been designed to eradicate resilient spores and are regularly used to decontaminate surfaces in clinical settings. Aptamers are short, artificial single-stranded oligonucleotides comprising DNA and/or RNA which bind to their targets with high selectivity and sensitivity.

Following treatment for 15 minutes in the absence of aptamers, none of the test solutions demonstrated sporicidal activity against *C. difficile* ATCC® 43598™ spores at concentrations of ≤50%, whereas a concentration of 25% Clinell® sporicidal solution demonstrated sporicidal activity against *C. difficile* SH11 spores. In the presence of aptamers, the MSC of the Clinell® sporicidal solution decreased against *C. difficile* ATCCR 43598™ spores. However, the MSC of the Clinell® sporicidal solution increased more than two-fold against *C. difficile* SH11 spores. No change in the sporicidal solution of the EndoSan® and Chemgene™ solutions were observed against either strain of *C. difficile* spores. The results suggest that the aptamers may have different binding affinities for different strains of *C. difficile* spores.

Example 3

The *Clostridioides difficile* (formerly *Clostridium difficile*) spore suspensions used in this study are listed in Table 20 below. *Clostridioides difficile* R20291 suspension was provided by SporeGen® on 23 Jan. 2020 and stored at 4° C. upon arrival. *Clostridioides difficile* SH11 suspension was provided by SporeGen® on 17 Feb. 2020 and stored at 4° C. upon arrival.

TABLE 20

| Ribotype | Description | In-test Concentration |
|---|---|---|
| RT027 (R20291) | Purified spore suspension | $1 \times 10^8 \pm 5 \times 10^7$ |
| RT078 (SH11) | Purified spore suspension | $1 \times 10^8 \pm 5 \times 10^7$ |
| ATCC ® 43598 ™ | Internal strain spore suspension | $1 \times 10^8 \pm 5 \times 10^7$ |

Test Agents

Test agents used in this study are listed in Table 21 and Table 22 below. Aptamers and buffers were provided by Aptamer Group Limited.

TABLE 21

| Test Agent Name | Buffer | Concentration Provided (μM) | In-test concentration (μM) |
|---|---|---|---|
| CDiff_F1 aptamer | BB+ Mg2+ | 100 | 20, 10, 5, 2.5 |

TABLE 22

| Test Agent Name | Product Type | Lot Number | In-test concentration (µM) |
|---|---|---|---|
| Clinell sporicidal solution | Liquid sporicidal | SA613818 | 50, 25, 12.5, 6.25, 3.125, 1.5625 |
| Negative control | PBS + 1% RCM | PBS200109/ RCM200109 | Not applicable |
| Positive Control | Bleach based solution | 9 302 2696 | Not applicable |

Equipment
- UKAS calibrated pipettes (0.5-1000 µL range), Proline® Plus—Sartorius, UK
- UKAS calibrated multichannel pipettes (P300 and P20)—Gilson®, UK
- Eppendorf 5452 minispin centrifuge—Eppendorf, DE
- Calibrated balance, Ohaus NV212—Scientific Laboratory Supplies Ltd (SLS), UK
- Anaerobic cabinet, Whitley MG500-Don Whitley Scientific Limited, UK
- Digital dry bath—SLS, UK
- Sterile universal tubes—SLS, UK
- 96—well plates—SLS, UK Media
- Nuclease free water—Aptamer Group, UK
- BB+Mg2+ buffer—Aptamer Group, UK
- Brain heart infusion agar—SLS, UK
- Sodium taurocholate—Sigma-Aldrich, UK
- Yeast extract—Sigma-Aldrich, UK
- Horse blood—TCS Biosciences, UK
- Reinforced clostridial medium (RCM), Acumedia®—SLS, UK
- Phosphate buffered saline (PBS)—SLS, UK
- Saponin—Sigma-Aldrich, UK
- Sodium thiosulfate—Sigma-Aldrich, UK
- Sodium dodecyl sulphate—Sigma-Aldrich, UK
- Lecithin—Sigma-Aldrich, UK
- L-histidine—Sigma-Aldrich, UK
- Tween 80—Sigma-Aldrich, UK Preparation of brain heart infusion agar supplemented with horse blood and yeast (BHI-YHT).

| Compound | Quantity |
|---|---|
| Brain heart infusion agar | 52 g |
| Yeast extract | 5 g |
| Sodium taurocholate hydrate | 1 g |
| Defibrinated horse blood | 70 mL |
| Distilled water | 1 L |

Method

The Evaluation of the Sporicidal Enhancement Capabilities of the CDiff_F1 Aptamer in Combination with Clinell® Sporicidal Solution Against *Clostridioides difficile* Spores.

Prior to testing, the CDiff_F1 aptamers were diluted in nuclease free water to a concentration of 80 µM. The aptamers were folded by heating to 95° C. in a digital dry bath for 5 minutes and then immediately placed on ice and cooled to 2° C. The aptamers were stored at 2-4° C. while in use. A *C. difficile* SH11 bacterial spore inoculum was prepared to 1×108±5×107 CFUmL−1 according to internal procedures. The inoculum was confirmed by serial dilution and plating out the resultant suspensions onto brain heart infusion agar supplemented with horse blood and yeast (BHI-YHT). The CDiff_F1 aptamers were further diluted in "BB+Mg2+" buffer to obtain two times in-test concentrations (40, 20, 10 and 5 M). Ten microlitres of *C. difficile* spores were added to 10 µL of each two times in-test concentration of CDiff_F1 aptamer. The spore suspension was pipette mixed and incubated with CDiff_F1 aptamer at room temperature for one hour. The spores were then washed three times by centrifuging at 13,400 RPM for 10 minutes. In each wash the supernatant was removed, and the pellet was resuspended in 100 µL of "BB+Mg2+" buffer. Following the third wash, the spores were resuspended in 100 µL of "BB+Mg2+" buffer and vortexed to obtain a homogenous solution.

A total of six, two times in-test concentrations of each sporicidal test agent were prepared from the stock (100%, 50%, 25%, 12.5%, 6.25%, 3.125%). Negative and positive control solutions were also prepared. Ten microliter aliquots of each sporicidal test agent concentration or control solution were added to the wells of a 96-well plate. A 10 µL aliquot of the aptamer-spore suspension was added to each test agent or control solution and pipette mixed. The final in-test concentrations of each sporicidal test agent were 50%, 25%, 12.5%, 6.25%, 3.125%, 1.5625%. The plates were then incubated for 15 minutes at 37° C.±2° C. in an anaerobic environment. Following incubation, 50 µL of GH neutraliser was added to each well and pipette mixed. A 10 µL aliquot of neutralised suspension was taken from each well and transferred to an agar plate and incubated for 48 hours at 37° C.±2° C. in an anaerobic environment. Growth was recorded as "+" and no growth as "−". The minimum sporicidal concentration (MSC) for each concentration was identified as the lowest concentration with no growth for all replicates. If growth was observed at the highest concentration it was displayed as ">". The test was repeated without the presence of the aptamers and without the presence of the Clinell® sporicidal solution. Testing was also repeated using *C. difficile* ATCC® 43598™ and *C. difficile* R20291 spores. Testing was performed in triplicate.

Results

The evaluation of the sporicidal enhancement capabilities of the CDiff_F1 aptamer in combination with Clinell® sporicidal solution against *Clostridioides difficile* spores 3.1.1 *Clostridioides difficile* SH11 Spores The growth of *C. difficile* SH11 spores was unaffected by the presence of any concentration of CDiff_F1 aptamers without the presence of Clinell® sporicidal solution. When the six concentrations of Clinell® sporicidal solution were assessed against *C. difficile* SH11 spores without the presence of the CDiff_F1 aptamer, the MSC was >50%. In the presence of and 2.5 µM, 5 µM and 10 µM CDiff_F1 aptamers, the MSC of Clinell® sporicidal solution was 25%. This was a >2-fold decrease in the MSC of Clinell® sporicidal solution. In the presence of 20 µM CDiff_F1 aptamers, the MSC of Clinell® sporicidal solution was 12.5%. This was a >4-fold decrease in the MSC of Clinell® sporicidal solution.

TABLE 23

Minimal sporicidal concentration (MSC) of CDiff_F1 aptamers and Clinell sporicidal solution against *C. difficile* SH11 spores in the presence and absence of various concentrations of CDiff_F1 aptamers.

| Concentration of CDiff_F1 (μM) | MSC of CDiff_F1 (μM) | MSC of Clinell No. CDiff_F1 | Sporicidal solution (%) with CDiff_F1 |
|---|---|---|---|
| 2.5 | >20 | >50 | 25 |
| 5 | >20 | >50 | 25 |
| 10 | >20 | >50 | 25 |
| 20 | >20 | >50 | 12.5 |

The growth of *C. difficile* ATCCR 43598™ spores was unaffected by the presence of any concentration of CDiff_F1 aptamers without the presence of Clinell® sporicidal solution (Table 24). When the six concentrations of Clinell® sporicidal solution were assessed against *C. difficile* ATCCR 43598™ spores without the presence of the CDiff_F1 aptamers, the MSC was >50%. In the presence of all the concentrations of CDiff_F1 aptamers, the MSC of Clinell® sporicidal solution was 25%. This was a >2-fold decrease in the MSC of Clinell® sporicidal solution.

TABLE 24

Minimal sporicidal concentration (MSC) of CDiff_F1 aptamers and Clinell sporicidal solution against *C. difficile* ATCC 43598 spores in the presence and absence of various concentrations of CDiff_F1 aptamers.

| Concentration of CDiff_F1 (μM) | MSC of CDiff_F1 (μM) | MSC of Clinell No. CDiff_F1 | Sporicidal solution (%) with CDiff_F1 |
|---|---|---|---|
| 2.5 | >20 | >50* | 25 |
| 5 | >20 | >50* | 25 |
| 10 | >20 | >50* | 25 |
| 20 | >20 | >50* | 25 |

*= No growth observed for one replicate showing that 50% Clinell sporicidal solution was enough to kill all spores for one replicate, however, 50% cannot be considered the MSC as growth was observed for the other two replicates.

TABLE 25

Minimal sporicidal concentration (MSC) of CDiff_F1 aptamers and Clinell sporicidal solution against *C. difficile* R20291 spores in the presence and absence of various concentrations of CDiff_F1 aptamers.

| Concentration of CDiff_F1 (μM) | MSC of CDiff_F1 (μM) | MSC of Clinell No. CDiff_F1 | Sporicidal solution (%) with CDiff_F1 |
|---|---|---|---|
| 2.5 | >20 | >50 | >50 |
| 5 | >20 | >50 | >50 |
| 10 | >20 | >50 | >50 |
| 20 | >20 | >50 | 50 |

TABLE 26

Sporicidal concentrations of Clinell ® sporicidal solution in the presence and absence of four concentrations of CDiff_F1 aptamers using *C. difficile* SH11 spores. Growth observed after recovering viable *C. difficile* SH11 spores following treatment for 15 minutes with six concentrations of Clinell sporicidal solution in the absence of CDiff_F1 aptamers "+" = growth present, "–" = no growth (n = 3).

| Concentration of Clinell ® sporicidal solution (%) | Aptamers absent | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | + | + | + | + | + | + |
| 25 | + | + | + | + | + | + |
| 12.5 | + | + | + | + | + | + |
| 6.25 | + | + | + | + | + | + |
| 3.125 | + | + | + | + | + | + |
| 1.5625 | + | + | + | + | + | + |

TABLE 27

Growth observed after recovering viable *C. difficile* SH11 spores following treatment for 15 minutes with six concentrations of Clinell ® sporicidal solution in the presence of CDiff_F1 aptamers at 20 μM "+" = growth present, "–" = no growth (n = 3).

| Concentration of Clinell ® sporicidal solution (%) | CDiff_F1 (20 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | – | – | – | – |
| 25 | – | – | – | – | – | – |
| 12.5 | – | – | – | – | – | – |
| 6.25 | + | + | + | + | + | + |
| 3.125 | + | + | + | + | + | + |
| 1.5625 | + | + | + | + | + | + |

TABLE 28

Growth observed after recovering viable *C. difficile* SH11 spores following treatment for 15 minutes with six concentrations of Clinell ® sporicidal solution in the presence of CDiff_F1 aptamers at 10 μM "+" = growth present, "–" = no growth (n = 3).

| Concentration of Clinell ® sporicidal solution (%) | CDiff_F1 (10 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | – | – | – | – |
| 25 | – | – | – | – | – | – |
| 12.5 | – | – | – | – | + | + |
| 6.25 | + | + | + | + | + | + |
| 3.125 | + | + | + | + | + | + |
| 1.5625 | + | + | + | + | + | + |

TABLE 29

Growth observed after recovering viable *C. difficile* SH11 spores following treatment for 15 minutes with six concentrations of Clinell ® sporicidal solution in the presence of CDiff_F1 aptamers at 5 μM "+" = growth present, "–" = no growth (n = 3).

| Concentration of Clinell ® sporicidal solution (%) | CDiff_F1 (5 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | – | – | – | – |
| 25 | – | – | – | – | – | – |
| 12.5 | – | – | + | + | + | + |
| 6.25 | + | + | + | + | + | + |
| 3.125 | + | + | + | + | + | + |
| 1.5625 | + | + | + | + | + | + |

TABLE 30

Growth observed after recovering viable *C. difficile* SH11 spores following treatment for 15 minutes with six concentrations of Clinell ® sporicidal solution in the presence of CDiff_F1 aptamers at 2.5 μM "+" = growth present, "–" = no growth (n = 3).

| Concentration of Clinell ® sporicidal solution (%) | CDiff_F1 (2.5 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | – | – | – | – |
| 25 | – | – | – | – | – | – |
| 12.5 | + | + | + | + | + | + |
| 6.25 | + | + | + | + | + | + |
| 3.125 | + | + | + | + | + | + |
| 1.5625 | + | + | + | + | + | + |

TABLE 31

Growth observed after recovering viable *C. difficile* SH11 spores following treatment for 15 minutes with four concentrations of aptamer "+" = growth present, "–" = no growth (n = 3).

| Concentration of CDiff_F1 aptamer (μM) | Aptamers only | | | | | |
|---|---|---|---|---|---|---|
| | N = 1 | | N = 2 | | N = 3 | |
| | 1.1 | 1.2 | 2.1 | 2.2 | 3.1 | 3.2 |
| 20 | + | + | + | + | + | + |
| 10 | + | + | + | + | + | + |
| 5 | + | + | + | + | + | + |
| 2.5 | + | + | + | + | + | + |

TABLE 32

Sporicidal concentrations of Clinell ® sporicidal solution in the absence of CDiff_F1 aptamers using *C. difficile* ATCC 43598 spores. Growth observed after recovering viable *C. difficile* 43598 spores following treatment for 15 minutes with six concentrations of Clinell sporicidal solution in the absence of CDiff_F1 aptamers "+" = growth present, "–" = no growth (n = 3).

| Concentration of Clinell ® sporicidal solution (%) | Aptamers Absent | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | + | + | + | + |
| 25 | + | + | + | + | + | + |
| 12.5 | + | + | + | + | + | + |
| 6.25 | + | + | + | + | + | + |
| 3.125 | + | + | + | + | + | + |
| 1.5625 | + | + | + | + | + | + |

TABLE 33

Sporicidal concentrations of Clinell ® sporicidal solution in the presence and absence of four concentrations of CDiff_F1 aptamers using *C. difficile* ATCC 43598 spores. Growth observed after recovering viable *C. difficile* 43598 spores following treatment for 15 minutes with six concentrations of Clinell sporicidal solution in the presence of CDiff_F1 aptamers at 20 μM "+" = growth present, "–" = no growth (n = 3).

| Concentration of Clinell ® sporicidal solution (%) | CDiff_F1 (20 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | – | – | – | – |
| 25 | – | – | – | – | – | – |
| 12.5 | + | + | + | + | + | + |
| 6.25 | + | + | + | + | + | + |
| 3.125 | + | + | + | + | + | + |
| 1.5625 | + | + | + | + | + | + |

TABLE 34

Sporicidal concentrations of Clinell ® sporicidal solution in the presence and absence of four concentrations of CDiff_F1 aptamers using *C. difficile* ATCC 43598 spores. Growth observed after recovering viable *C. difficile* 43598 spores following treatment for 15 minutes with six concentrations of Clinell ® sporicidal solution in the presence of CDiff_F1 aptamers at 10 μM + = growth present, – = no growth (n = 3).

| Concentration of Clinell ® sporicidal solution (%) | CDiff_F1 (10 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | – | – | – | – | – | – |
| 25 | – | – | – | – | – | – |
| 12.5 | + | + | + | + | + | + |
| 6.25 | + | + | + | + | + | + |
| 3.125 | + | + | + | + | + | + |
| 1.5625 | + | + | + | + | + | + |

TABLE 35

Sporicidal concentrations of Clinell ® sporicidal solution in the presence and absence of four concentrations of CDiff_F1 aptamers using *C. difficile* ATCC 43598 spores. Growth observed after recovering viable *C. difficile* 43598 spores following treatment for 15 minutes with six concentrations of Clinell ® sporicidal solution in the presence of CDiff_F1 aptamers at 5 μM + = growth present, − = no growth (n = 3).

| Concentration of Clinell ® sporicidal solution (%) | CDiff_F1 (5 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | − | − | − | − | − | − |
| 25 | − | − | − | − | − | − |
| 12.5 | + | + | + | + | + | + |
| 6.25 | + | + | + | + | + | + |
| 3.125 | + | + | + | + | + | + |
| 1.5625 | + | + | + | + | + | + |

TABLE 36

Sporicidal concentrations of Clinell ® sporicidal solution in the presence and absence of four concentrations of CDiff_F1 aptamers using *C. difficile* ATCC 43598 spores. Growth observed after recovering viable *C. difficile* 43598 spores following treatment for 15 minutes with six concentrations of Clinell ® sporicidal solution in the presence of CDiff_F1 aptamers at 2.5 μM + = growth present, − = no growth (n = 3).

| Concentration of Clinell ® sporicidal solution (%) | CDiff_F1 (2.5 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | − | − | − | − | − | − |
| 25 | − | − | − | − | − | − |
| 12.5 | + | + | + | + | + | + |
| 6.25 | + | + | + | + | + | + |
| 3.125 | + | + | + | + | + | + |
| 1.5625 | + | + | + | + | + | + |

TABLE 37

Growth observed after recovering viable *C. difficile* ATCC 43598 spores following treatment for 15 minutes with four concentrations of aptamer "+" = growth present, "−" = no growth (n = 3).

| Concentration of CDiff_F1 aptamer (μM) | Aptamers only | | | | | |
|---|---|---|---|---|---|---|
| | N = 1 | | N = 2 | | N = 3 | |
| | 1.1 | 1.2 | 2.1 | 2.2 | 3.1 | 3.2 |
| 20 | + | + | + | + | + | + |
| 10 | + | + | + | + | + | + |
| 5 | + | + | + | + | + | + |
| 2.5 | + | + | + | + | + | + |

TABLE 38

Sporicidal concentrations of Clinell ® sporicidal solution in the presence and absence of four concentrations of CDiff_F1 aptamers using *C. difficile* R20291 spores. Growth observed after recovering viable *C. difficile* R20291 spores following treatment for 15 minutes with six concentrations of Clinell sporicidal solution in the absence of CDiff_F1 aptamers "+" = growth present, "−" = no growth (n = 3).

| Concentration of Clinell ® sporicidal solution (%) | Aptamers Absent | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | + | + | + | + | + | + |
| 25 | + | + | + | + | + | + |
| 12.5 | + | + | + | + | + | + |
| 6.25 | + | + | + | + | + | + |
| 3.125 | + | + | + | + | + | + |
| 1.5625 | + | + | + | + | + | + |

TABLE 39

Sporicidal concentrations of Clinell ® sporicidal solution in the presence and absence of four concentrations of CDiff_F1 aptamers using *C. difficile* R20291 spores. Growth observed after recovering viable *C. difficile* R20291 spores following treatment for 15 minutes with six concentrations of Clinell ® sporicidal solution in the presence of CDiff_F1 aptamers at 20 μM "+" = growth present, "−" = no growth (n = 3).

| Concentration of Clinell ® sporicidal solution (%) | CDiff_F1 (20 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | − | − | − | − | − | − |
| 25 | − | + | + | + | − | − |
| 12.5 | + | + | + | + | + | + |
| 6.25 | + | + | + | + | + | + |
| 3.125 | + | + | + | + | + | + |
| 1.5625 | + | + | + | + | + | + |

TABLE 40

Sporicidal concentrations of Clinell ® sporicidal solution in the presence and absence of four concentrations of CDiff_F1 aptamers using *C. difficile* R20291 spores. Growth observed after recovering viable *C. difficile* R20291 spores following treatment for 15 minutes with six concentrations of Clinell ® sporicidal solution in the presence of CDiff_F1 aptamers at 10 μM "+" = growth present, "−" = no growth (n = 3).

| Concentration of Clinell ® solution (%) sporicidal | CDiff_F1 (10 μM) | | | | | |
|---|---|---|---|---|---|---|
| | N = 1 | | N = 2 | | N = 3 | |
| | 1.1 | 1.2 | 2.1 | 2.2 | 3.1 | 3.2 |
| 50 | − | + | + | + | − | − |
| 25 | + | + | + | + | + | + |
| 12.5 | + | + | + | + | + | + |
| 6.25 | + | + | + | + | + | + |
| 3.125 | + | + | + | + | + | + |
| 1.5625 | + | + | + | + | + | + |

TABLE 41

Sporicidal concentrations of Clinell ® sporicidal solution in the presence and absence of four concentrations of CDiff_F1 aptamers using *C. difficile* R20291 spores. Growth observed after recovering viable *C. difficile* R20291 spores following treatment for 15 minutes with six concentrations of Clinell ® sporicidal solution in the presence of CDiff_F1 aptamers at 5 μM "+" = growth present, "−" = no growth (n = 3).

| Concentration | CDiff_F1 (5 μM) | | | | | |
|---|---|---|---|---|---|---|
| of Clinell ® sporicidal | N = 1 | | N = 2 | | N = 3 | |
| solution (%) | 1.1 | 1.2 | 2.1 | 2.2 | 3.1 | 3.2 |
| 50 | + | + | + | + | + | + |
| 25 | + | + | + | + | + | + |
| 12.5 | + | + | + | + | + | + |
| 6.25 | + | + | + | + | + | + |
| 3.125 | + | + | + | + | + | + |
| 1.5625 | + | + | + | + | + | + |

TABLE 42

Sporicidal concentrations of Clinell ® sporicidal solution in the presence and absence of four concentrations of CDiff_F1 aptamers using *C. difficile* R20291 spores. Growth observed after recovering viable *C. difficile* R20291 spores following treatment for 15 minutes with six concentrations of Clinell ® sporicidal solution in the presence of CDiff_F1 aptamers at 5 μM "+" = growth present, "−" = no growth (n = 3).

| Concentration | CDiff_F1 (2.5 μM) | | | | | |
|---|---|---|---|---|---|---|
| of Clinell ® | N = 1 | | N = 2 | | N = 3 | |
| sporicidal solution (%) | 1.1 | 1.2 | 2.1 | 2.2 | 3.1 | 3.2 |
| 50 | + | + | + | + | + | + |
| 25 | + | + | + | + | + | + |
| 12.5 | + | + | + | + | + | + |
| 6.25 | + | + | + | + | + | + |
| 3.125 | + | + | + | + | + | + |
| 1.5625 | + | + | + | + | + | + |

TABLE 43

Growth observed after recovering viable *C. difficile* R20291 spores following treatment for 15 minutes with four concentrations of aptamer "+" = growth present, "−" = no growth (n = 3).

| Concentration | Aptamers only | | | | | |
|---|---|---|---|---|---|---|
| of CDiff_F1 | N = 1 | | N = 2 | | N = 3 | |
| aptamer (μM) | 1.1 | 1.2 | 2.1 | 2.2 | 3.1 | 3.2 |
| 20 | + | + | + | + | + | + |
| 10 | + | + | + | + | + | + |
| 5 | + | + | + | + | + | + |
| 2.5 | + | + | + | + | + | + |

Discussion

*C. difficile* is an anaerobic spore-forming bacterium recognised for causing nosocomial infections worldwide. *C. difficile* spores exist in a wide range of environments due to their resilience to cleaning regimes. Sporicidal solutions have been designed to eradicate resilient spores and are regularly used to decontaminate surfaces in clinical settings. The addition of CDiff_F1 aptamers enhanced the sporicidal capabilities of the Clinell® sporicidal solution against all three strains of *C. difficile* spores. The sporicidal enhancement of the Clinell® sporicidal solution varied between the three strains, with the greatest reduction in the MSC in the Clinell® sporicidal solution observed from *C. difficile* SH11 spores in combination with 20 μM CDiff_F1 aptamers. The addition of only CDiff_F1 aptamers did not affect the growth of any strain of *C. difficile* spores which may suggest an interaction between the aptamers and the Clinell® sporicidal solution once bound to the spores. The results suggest that CDiff_F1 aptamer may have the greatest binding affinity for *C. difficile* SH11 spores.

Example 4

Test Microorganisms

The *Clostridioides difficile* (formerly *Clostridium difficile*) spore suspensions used in this study are listed in Table 1. *Clostridioides difficile* R20291 suspension was provided by SporeGen® on 23 Jan. 2020 and stored at 4° C. upon arrival. *Clostridioides difficile* SH11 suspension was provided by SporeGen® on 17 Feb. 2020 and stored at 4° C. upon arrival.

TABLE 44

*C. difficile* strains

| Organism | Ribotype | Description | In-test concentration (CFUmL-1) |
|---|---|---|---|
| *C. difficile* | RT027 (R20291) | Purified spore suspension | $1 \times 10^7 \pm 5 \times 10^6$ |
| *C. difficile* | RT078 (SHU) | Purified spore suspension | $1 \times 10^7 \pm 5 \times 10^6$ |
| *C. difficile* | ATCC ® 43598 ™ | Internal strain spore suspension | $1 \times 10^7 \pm 5 \times 10^6$ |

TABLE 45

Test Agents Used

| Test agent name | Product type | Lot number | In-test concentrations (%) |
|---|---|---|---|
| Clinell ® sporicidal solution | Liquid sporicidal | SA613818 | 50, 25, 12.5, 6.25, 3.125, 1.5625 |
| Negative control | PBS + 1% RCM | PBS200122/ RCM200109 | N/A |
| Positive control | Bleach-based solution | 9 302 2696 | N/A |

PBS = phosphate buffered saline,
RCM = reinforced clostridial medium.

Equipment and Media

Media

Nuclease free water—provided by Aptamer Group, UK

"TbKst" buffer—provided by Aptamer group, UK "TbKat" buffer-provided by

Aptamer group, UK Sodium taurocholate—Sigma-Aldrich, UK

Yeast extract—Sigma-Aldrich, UK Horse blood—TCS Biosciences Ltd, UK

Reinforced clostridial medium (RCM), Acumedia®—SLS, UK Phosphate buffered saline (PBS)—SLS, UK Saponin—Sigma-Aldrich, UK Sodium thiosulfate—Sigma-Aldrich, UK Sodium dodecyl sulphate—Sigma-Aldrich, UK Lecithin—Sigma-Aldrich, UK L-histidine—Sigma-Aldrich, UK Tween 80—Sigma-Aldrich, UK Method Evaluation of the Sporicidal Enhancement Capabilities of CotE_H2 and CDec_D1 Aptamers in Combination with Clinell® Sporicidal Solution Against *Clostridioides difficile* Spores.

Prior to testing, CotE_H2 aptamers were diluted in nuclease free water to a concentration of 80 μM. The aptamers were folded by heating to 95° C. in a digital dry bath for 5 minutes and then immediately placed on ice and cooled to 2° C. The aptamers were stored at 2-4° C. while in use. A *Clostridioides difficile* SH11 bacterial spore inoculum was prepared to $1\times10^{7}\pm5\times10^{6}$ $CFUmL^{-1}$ according to internal procedures. The inoculum was confirmed by serial dilution and plating out the resultant suspensions onto brain heart infusion agar supplemented with horse blood and yeast (BHI-YHT). CotE_H2 aptamers were further diluted in "TbKst" buffer to obtain 2× in-test concentrations (40, 20, 10 and 5 μM). Ten microlitres of *C. difficile* spores were added to 10 μL of each 2× in-test concentration of CotE_H2 aptamer. The spore suspension was pipette mixed and incubated with CotE_H2 aptamer at room temperature for one hour. The spores were then washed three times by centrifuging at 13,400 RPM for 10 minutes. In each wash the supernatant was removed, and the pellet was resuspended in 100 μL of "TbKst" buffer. Following the third wash, the spores were resuspended in 100 μL of "TbKst" buffer and vortexed to obtain a homogenous solution.

A total of six 2× in-test concentrations (1:2 dilutions) of the sporicidal test agent were prepared from the stock (100%, 50%, 25%, 12.5%, 6.25%, 3.125%). Negative and positive control solutions were also prepared. Ten microliter aliquots of each sporicidal test agent concentration or control solution were added to the wells of a 96-well plate. A 10 μL aliquot of the aptamer-spore suspension was added to each test agent or control solution and pipette mixed. The final in-test concentrations of the sporicidal test agent were 50%, 25%, 12.5%, 6.25%, 3.125%, 1.5625%. The plates were then incubated for 15 minutes at 37° C.±2° C. in an anaerobic environment. Following incubation, 50 μL of GH neutraliser was added to each well and pipette mixed. A 10 μL aliquot of neutralised suspension was taken from each well and transferred to an agar plate and incubated for 48 hours at 37° C.±2° C. in an anaerobic environment. Growth was recorded as "+" and no growth as "−". The minimum sporicidal concentration (MSC) for each spore and aptamer concentration was identified as the lowest concentration with no growth for all replicates. If growth was observed at the highest concentration it was displayed as ">". The test was repeated without the presence of the aptamers and without the presence of the Clinell® sporicidal solution. Testing was also repeated using *C. difficile* ATCCR 43598™ and *C. difficile* R20291 spores. Testing was performed in triplicate. The method was repeated with CDec_D1 aptamers for all three strains of *C. difficile* spores.

Results

Evaluation of the Sporicidal Enhancement Capabilities of the CotE_H2 Aptamer in Combination with Clinell® Sporicidal Solution Against *Clostridioides difficile* Spores.

*Clostridioides difficile* SH11 Spores

The growth of *C. difficile* SH11 spores was unaffected by the presence of any concentration of CotE_H2 aptamers without the presence of the Clinell® sporicidal solution. When the six concentrations of Clinell® sporicidal solution were assessed against *C. difficile* SH11 spores without the presence of the CotE_H2 aptamer, the MSC was 25%. In the presence of 20 μM, 10 μM, 5 μM and 2.5 μM CotE_H2 aptamers, the MSC of Clinell® sporicidal solution was 12.5%. This was a two-fold decrease in the MSC of Clinell® sporicidal solution.

TABLE 46

Minimal sporicidal concentration (MSC) of CotE_H2 aptamers and Clinell ® sporicidal solution against *Clostridioides difficile* SH11 spores, in the presence and absence of various concentrations of CotE_H2 aptamers.

| Concentration of CotE_H2 (μM) | MSC of CotE_H2 (μM) | MSC of Clinell ® sporicidal solution (%) | |
|---|---|---|---|
| | | No CotE_H2 | With CotE_H2 |
| 2.5 | >20 | 25 | 12.5 |
| 5 | >20 | 25 | 12.5 |
| 10 | >20 | 25 | 12.5 |
| 20 | >20 | 25 | 12.5 |

*Clostridioides difficile* ATCC® 43598™ Spores

The growth of *C. difficile* ATCCR 43598™ spores was unaffected by the presence of any concentration of CotE_H2 aptamers without the presence of the Clinell® sporicidal solution. When the six concentrations of Clinell® sporicidal solution were assessed against *C. difficile* ATCC® 43598™ spores without the presence of the CotE_H2 aptamers, the MSC was 12.5%. The presence of 20 μM, 10 μM, 5 μM and 2.5 μM CotE_H2 aptamers did not affect the MSC of Clinell® sporicidal solution.

TABLE 47

Minimal sporicidal concentration (MSC) of CotE_H2 aptamers and Clinell ® sporicidal solution against *Clostridioides difficile* ATCC ® 43598 ™ spores, in the presence and absence of various concentrations of CotE_H2 aptamers.

| Concentration of CotE_H2 (μM) | MSC of CotE_H2 (μM) | MSC of Clinell ® sporicidal solution (%) | |
|---|---|---|---|
| | | No CotE_H2 | With CotE_H2 |
| 2.5 | >20 | 12.5 | 12.5 |
| 5 | >20 | 12.5 | 12.5 |
| 10 | >20 | 12.5 | 12.5 |
| 20 | >20 | 12.5 | 12.5 |

*Clostridioides difficile* R20291 Spores

The growth of *C. difficile* R20291 spores was unaffected by the presence of any concentration of CotE_H2 aptamers without the presence of the Clinell® sporicidal solution. When the six concentrations of Clinell® sporicidal solution were assessed against *C. difficile* R20291 spores without the presence of the CotE_H2 aptamers, the MSC was 25%. In the presence of 20 μM CotE_H2 aptamers, the MSC of Clinell® sporicidal solution was 12.5%. This was a two-fold decrease in the MSC of Clinell® sporicidal solution. The presence of 10 μM, 5 μM and 2.5 μM CotE_H2 aptamers did not affect the MSC of Clinell® sporicidal solution when assessed against *C. difficile* R20291 spores.

TABLE 48

Minimal sporicidal concentration (MSC) of Clinell ® sporicidal solution against *Clostridioides difficile* R20291 spores, in the presence and absence of various concentrations of CotE_H2 aptamers.

| Concentration of CotE_H2 (μM) | MSC of CotE_H2 (μM) | MSC of Clinell® sporicidal solution | |
|---|---|---|---|
| | | No CotE_H2 | With CotE_H2 |
| 2.5 | >20 | 25 | 25 |
| 5 | >20 | 25 | 25 |
| 10 | >20 | 25 | 25 |
| 20 | >20 | 25 | 12.5 |

Example 6

Evaluation of the sporicidal enhancement capabilities of the CDec_D1 aptamer in combination with Clinell® sporicidal solution against *Clostridioides difficile* spores

*Clostridioides difficile* SH11 Spores

The growth of *C. difficile* SH11 spores was unaffected by the presence of any concentration of CDec_D1 aptamers without the presence of the Clinell® sporicidal solution. When the six concentrations of Clinell® sporicidal solution were assessed against *C. difficile* SH11 spores without the presence of the CDec_D1 aptamer, the MSC was 50%. In the presence of 20 μM, 10 μM and 5 μM CDec_D1 aptamers, the MSC of Clinell® sporicidal solution was 25%. This was a 2-fold decrease in the MSC of Clinell® sporicidal solution. The presence of 2.5 μM CDec_D1 aptamers did not affect the MSC of Clinell® sporicidal solution.

TABLE 49

Minimal sporicidal concentration (MSC) of Clinell ® sporicidal solution against *Clostridioides difficile* SH11 spores, in the presence and absence of various concentrations of CDec_D1 aptamers.

| Concentration of CDec_D1 (μM) | MSC of CDec_D1 (μM) | MSC of Clinell ® sporicidal solution (%) | |
|---|---|---|---|
| | | No CDec_D1 | With CDec_D1 |
| 2.5 | >20 | 50 | 50 |
| 5 | >20 | 50 | 25 |
| 10 | >20 | 50 | 25 |
| 20 | >20 | 50 | 25 |

*Clostridioides difficile* ATCC® 43598™ Spores

The growth of *C. difficile* ATCCR 43598™ spores was unaffected by the presence of any concentration of CDec_D1 aptamers without the presence of the Clinell® sporicidal solution. When the six concentrations of Clinell® sporicidal solution were assessed against *C. difficile* ATCCR 43598™ spores without the presence of the CDec_D1 aptamers, the MSC was 25%. In the presence of 20 μM, μM and 5 μM CDec_D1 aptamers, the MSC of Clinell® sporicidal solution was 12.5%. This was a two-fold decrease in the MSC of Clinell® sporicidal solution. The presence of 2.5 μM CDec_D1 aptamers did not affect the MSC of Clinell® sporicidal solution.

TABLE 50

Minimal sporicidal concentration (MSC) of Clinell ® sporicidal solution against *Clostridioides difficile* ATCC ® 43598 ™ spores, in the presence and absence of various concentrations of CDec_D1 aptamers.

| Concentration of CDec_D1 (μM) | MSC of CDec_D1 (μM) | MSC of Clinell ® sporicidal solution (%) | |
|---|---|---|---|
| | | No CDec_D1 | With CDec_D1 |
| 2.5 | >20 | 25 | 25 |
| 5 | >20 | 25 | 12.5 |
| 10 | >20 | 25 | 12.5 |
| 20 | >20 | 25 | 12.5 |

*Clostridioides difficile* R20291 Spores

The growth of *C. difficile* R20291 spores was unaffected by the presence of any concentration of CDec_D1 aptamers without the presence of the Clinell® sporicidal solution. When the six concentrations of Clinell® sporicidal solution were assessed against *C. difficile* R20291 spores without the presence of the CDec_D1 aptamers, the MSC was 50%. In the presence of 20 μM and 10 μM CDec_D1 aptamers, the MSC of Clinell® sporicidal solution was 12.5%. This was a 4-fold decrease in the MSC of Clinell® sporicidal solution. The presence of 5 μM and 2.5 μM CDec_D1 aptamers did not affect the MSC of Clinell® sporicidal solution when assessed against C. *Difficile* R20291 spores.

TABLE 51

Minimal sporicidal concentration (MSC) of Clinell ® sporicidal solution against *Clostridioides difficile* R20291 spores, in the presence and absence of various concentrations of CDec_D1 aptamers.

| Concentration of CDec_D1 (μM) | MSC of CDec_D1 (μM) | MSC of Clinell ® sporicidal solution (%) | |
|---|---|---|---|
| | | No CDec_D1 | With CDec_D1 |
| 2.5 | >20 | 50 | 50 |
| 5 | >20 | 50 | 50 |
| 10 | >20 | 50 | 12.5 |
| 20 | >20 | 50 | 12.5 |

Discussion

*Clostridioides difficile* is an anaerobic spore-forming bacterium, recognised for causing nosocomial infections worldwide. *Clostridioides difficile* spores exist in a wide range of environments due to their resilience to cleaning regimes. Sporicidal solutions have been designed to eradicate resilient spores and are regularly used to decontaminate surfaces in clinical settings. The presence of an exosporium layer makes *C. difficile* spores more resistant to sporicidal products in comparison to other spore strains, as the sporicidal agents may struggle to penetrate this layer. Aptamers are short, artificial, single-stranded DNA or RNA oligonucleotides which bind to their targets with high selectivity and sensitivity.

The addition of CotE_H2 aptamers enhanced the sporicidal capabilities of the Clinell® sporicidal solution against *C. difficile* SH11 and R20291 spores. The addition of all concentrations of CotE_H2 aptamers reduced the MSC of the Clinell® sporicidal solution against *C. difficile* SH11 spores, whereas only the addition of 20 μM CotE_H2 aptamers reduced the MSC of the Clinell® sporicidal solution against *C. difficile* R20291 spores.

The addition of CDec_D1 aptamers enhanced the sporicidal capabilities of the Clinell® sporicidal solution against all three strains of *C. difficile* spores. The sporicidal enhancement varied between the three strains, with the greatest fold reduction observed in the MSC of the Clinell® sporicidal against *C. difficile* R20291 spores in combination with 10 μM and 20 μM CDec_D1 aptamers. Aptamers may affect the biochemical or biophysical properties of the exosporium layer of *C. difficile* spores during binding, which may increase their susceptibility to sporicidal products.

The results suggest that the CotE_H2 aptamers have the greatest affinity for the *C. difficile* SH11 spores, whereas the CDec_D1 aptamers have the greatest affinity for the *C. difficile* R20291 spores. The results also suggest that the sporicidal enhancement is dependent on the concentration of aptamers present as the addition of 2.5 μM CDec_D1 aptamers did not affect the MSC of the Clinell® sporicidal solution against all three strains of *C. difficile* spores.

Discussion

Aptamers described herein may have utility in enhancing the sporicidal activity of a sporicidal agent such as peracetic acid. Different aptamers (raised to different targets of the *C. difficile* spore) may have different effects on the sporicidal activity of peracetic acid against different spore strains. For example, 20 μM of the CDiff_F1 aptamer may result in an up to 4-fold reduction in the concentration of peracetic acid required for sporicidal activity against spores of the SH11 strain. Furthermore, CDiff_F1 aptamer may result in an up to 2-fold reduction in the concentration of peracetic acid required for sporicidal activity against spores of the ATCC 43598 strain after 15 minutes. Aptamer Chitinase_D11 and Aptamer CdeC_D1 may each result in an up to 4-fold reduction in the concentration of peracetic acid required for sporicidal activity against spores of the R20291 strain.

The references cited throughout this application, are incorporated herein in their entireties for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this disclosure is not limited to the particular embodiments disclosed but is intended to cover all modifications which are within the spirit and scope of the disclosure as defined by the appended claims and/or the above description.

The invention claimed is:

1. A method for killing or inactivating *Clostridioides difficile* (*C. difficile*) spores, comprising contacting the spores with an agent selected from the group consisting of a sporicidal agent and a sporostatic agent; and an aptamer capable of specifically binding to *C. difficile*, wherein the aptamer includes a nucleic acid sequence having at least 95% sequence identity with any one of the nucleic acid sequences as set forth in any of SEQ ID NOs: 1 to 14, 23 to 39, or 43 to 55.

2. A method for enhancing a sporicidal effect against *C. difficile* of a sporicidal agent, the method comprising contacting *C. difficile* spores with an aptamer capable of specifically binding to *C. difficile* spores and an agent selected from the group consisting of a sporicidal agent and a sporostatic agent, wherein the aptamer includes a nucleic acid sequence having at least 95% sequence identity with any one of the nucleic acid sequences as set forth in any of SEQ ID NOs: 1 to 14, 23 to 39, or 43 to 55.

3. The method according to claim 1 or claim 2, wherein the agent is a sporicidal agent.

4. The method according to claim 1 or claim 2, comprising locating the aptamer and the sporicidal agent at a location suspected of comprising *C. difficile* spores.

5. The method according to claim 4, wherein the location comprises a surface and the method comprises contacting the surface with the sporicidal agent prior to, at essentially the same time, or subsequent to contacting the surface with the aptamer.

6. The method according to claim 5, which comprises:
- contacting the surface with the aptamers for a predetermined period of time configured to enable the aptamer to bind to the *C. difficile* spore to form aptamer-spore complex, and
- contacting the surface comprising the aptamer-spore complex with the sporicidal agent.

7. The method according to claim 5, further comprising contacting the surface with a GH neutralizer.

8. The method according to claim 5, comprising submerging the *C. difficile* spores with a composition comprising the aptamer and/or submerging the spores in the sporicidal agent.

9. The method according to claim 5, wherein the method comprises spraying the *C. difficile* spores with a composition comprising the aptamer and/or spraying the *C. difficile* spores with the sporicidal agent.

10. The method according to claim 5 wherein the method comprises applying a composition comprising the aptamer by means of a cloth and/or applying the sporicidal agent by means of a cloth and/or a wipe.

11. The method according to claim 1 or claim 2, wherein the method is performed at a temperature of about 5° C., 10° C., 15° C., 20° C., 25° C., 30° C., 35° C., 40° C., 45° C., 50° C., 55° C., 60° C., 65° C., 70° C., 75° C., 80° C. or 90° C.

12. The method according to claim 1 or claim 2, wherein a *C. difficile* spore comprises a coat surface protein or an exosporium layer protein.

13. The method according to claim 12, wherein the *C. difficile* protein comprises CdeC, CdeM, CotA, CotE or CotE Chitinase.

14. The method according to claim 13, wherein the *C. difficile* protein is a CdeC protein having an amino acid sequence as set forth in SEQ. ID. NO. 18.

15. The method according to claim 13, wherein the *C. difficile* protein is a CdeM protein having an amino acid sequence as set forth in SEQ. ID. NO. 19.

16. The method according to claim 13, wherein the *C. difficile* protein is a CotA protein having an amino acid sequence as set forth in SEQ. ID. NO. 15.

17. The method according to claim 13, wherein the *C. difficile* protein is a CotE protein having an amino acid sequence as set forth in SEQ. ID. NO. 16.

18. The method according to claim 13, wherein the *C. difficile* protein is a CotE Chitinase protein having an amino acid sequence as set forth in SEQ. ID. NO. 17.

19. The method according to claim 1, wherein the aptamer comprises or consists of:
- (a) a nucleic acid sequence selected from any one of the nucleic acid sequences as set forth in any of SEQ ID NOs: 1 to 14, 23 to 39, or 43 to 55; or
- (b) a nucleic acid sequence having at least 95%, sequence identity with SEQ ID NO: 1, 5 and 6.

20. The method according to claim 12, wherein the aptamer is a single stranded DNA aptamer.

21. The method according to claim 12, wherein the aptamer is selected from:
a) an aptamer which specifically binds to a CdeC;
b) an aptamer which specifically binds to CdeM,
c) an aptamer which specifically binds to CotA,
d) an aptamer which specifically binds to CotE;
e) an aptamer which specifically binds to CotE Chitinase; and
f) a combination of any of (a) to (e).

22. The method according to claim 4, comprising contacting the location with a plurality of aptamers, wherein each aptamer is capable of specifically binding to a *C. difficile* spore, wherein the plurality of aptamers comprises at least two aptamers capable of specifically binding to the same epitope of a *C. difficile* spore and/or at least two aptamers each aptamer capable of specifically binding to a different epitope of a *C. difficile* spore.

23. The method according to claim 22, wherein the plurality of aptamers comprises at least two aptamers selected from the group consisting of an aptamer comprising, consisting essentially of, or consisting of:
(a) a nucleic acid sequence selected from any one of the nucleic acid sequences as set forth in any of SEQ ID NOs: 1 to 14, 23 to 39, or 43 to 55;
(b) a nucleic acid sequence having at least 95% sequence identity with any one of the nucleic acid sequences as set forth in any of SEQ ID NOs: 1 to 14, 23 to 39, or 43 to 55;
or
(c) a combination of (a) to (b).

24. The method according to claim 22, wherein the plurality of aptamers comprises at least two aptamers selected from the group consisting of:
a) an aptamer which specifically binds to a CdeC;
b) an aptamer which specifically binds to CdeM,
c) an aptamer which specifically binds to CotA,
d) an aptamer which specifically binds to CotE;
e) an aptamer which specifically binds to CotE Chitinase; and
f) a combination of any of (a) to (e).

25. The method according to claim 22, wherein the plurality of aptamers comprises:
an aptamer comprising, consisting essentially of, or consisting of a nucleic acid sequence as set forth in SEQ. ID. NO. 1;
an aptamer comprising, consisting essentially of, or consisting of a nucleic acid sequence as set forth in SEQ. ID. NO. 5; and
an aptamer comprising, consisting essentially of, or consisting of a nucleic acid sequence as set forth in SEQ. ID. NO. 6.

26. The method according to claim 1 or claim 2, wherein the method comprises determining the presence, absence and/or concentration of *C. difficile* at a location prior to contacting the location with the sporicidal agent and/or sporostatic agent, wherein the step of determining comprises contacting the location with an aptamer and a detection molecule for a time sufficient for an aptamer-spore complex to form.

27. The method according to claim 26, wherein the aptamer comprises a detectable label.

28. The method according to claim 27, wherein the detectable label is selected from a fluorophore, a nanoparticle, a quantum dot, an enzyme, a radioactive isotope a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, and a liposome.

29. The method according to claim 1 or claim 2, wherein the agent is a sporicidal solution comprising chlorhexidine gluconate and optionally isopropyl alcohol.

30. The method according to claim 1 or claim 2, wherein the agent is a sporicidal agent which comprises peracetic acid and/or peracetic acid generating agent.

31. The method according to claim 30, wherein the sporicidal agent is a peracetic acid generating agent, and wherein the method further comprises wetting a wipe comprising sodium percarbonate with an aqueous solution prior to contacting a location suspected of comprising *C. difficile* spores.

32. The method according to claim 1 or claim 2, wherein the agent is a sporicidal solution comprising hydrogen peroxide and optionally a silver stabilised hydrogen peroxide.

33. The method according to claim 1 or claim 2, wherein the agent is a sporicidal solution comprising chlorhexidine gluconate and 70% isopropyl alcohol complex.

34. The method according to claim 1 or claim 2, comprising locating a combination of sporicidal and/or sporostatic agents.

35. The method according to claim 34, wherein the combination comprises peracetic acid and hydrogen peroxide.

* * * * *